United States Patent
Sun et al.

(10) Patent No.: US 10,906,679 B1
(45) Date of Patent: Feb. 2, 2021

(54) METHOD FOR PREPARING COLLAGEN-BASED MATERIALS

(71) Applicant: LifeCell Corporation, Madison, NJ (US)

(72) Inventors: Wendell Sun, Warrington, PA (US); Jerome Connor, Westminster, CO (US); Qing-Qing Qiu, Branchburg, NJ (US); Rick T. Owens, Stewartsville, NJ (US)

(73) Assignee: LifeCell Corporation, Madison, NJ (US)

( * ) Notice: Subject to any disclaimer, the term of this patent is extended or adjusted under 35 U.S.C. 154(b) by 72 days.

(21) Appl. No.: 16/410,319

(22) Filed: May 13, 2019

Related U.S. Application Data

(63) Continuation of application No. 14/836,508, filed on Aug. 26, 2015, now Pat. No. 10,322,835, which is a continuation of application No. 12/650,902, filed on Dec. 31, 2009, now Pat. No. 9,150,318.

(60) Provisional application No. 61/142,308, filed on Jan. 2, 2009.

(51) Int. Cl.
| | |
|---|---|
| *B65B 55/02* | (2006.01) |
| *B65B 55/22* | (2006.01) |
| *B65B 31/02* | (2006.01) |
| *B65B 55/08* | (2006.01) |
| *A61L 27/36* | (2006.01) |
| *A61L 2/00* | (2006.01) |
| *B65B 55/16* | (2006.01) |

(52) U.S. Cl.
CPC .............. *B65B 55/02* (2013.01); *A61L 2/007* (2013.01); *A61L 2/0035* (2013.01); *A61L 2/0088* (2013.01); *A61L 27/3683* (2013.01); *A61L 27/3687* (2013.01); *A61L 27/3691* (2013.01); *B65B 31/02* (2013.01); *B65B 55/08* (2013.01); *B65B 55/16* (2013.01); *B65B 55/22* (2013.01); *A61L 2430/40* (2013.01)

(58) Field of Classification Search
CPC ......... B65B 55/02; B65B 55/08; B65B 55/16; B65B 55/22; A61L 2/0029; A61L 2/0035; A61L 2/007; A61L 2430/40; A61L 2/0088; A61L 27/3683; A61L 27/3687
USPC ........... 53/425, 431; 422/21, 22, 28; 435/1.1
See application file for complete search history.

(56) References Cited

U.S. PATENT DOCUMENTS

| | | |
|---|---|---|
| 2,908,615 A | 10/1959 | Keil |
| 4,043,996 A | 8/1977 | Donnelly et al. |
| 4,098,571 A | 7/1978 | Miyata et al. |

(Continued)

FOREIGN PATENT DOCUMENTS

| | | |
|---|---|---|
| WO | WO-89/01790 A1 | 3/1989 |
| WO | WO-95/24837 A1 | 9/1995 |

(Continued)

OTHER PUBLICATIONS

American Association of Tissue Banks: Standards for Tissue Banking, 63 pages (1998).

(Continued)

*Primary Examiner* — Stephen F. Gerrity
(74) *Attorney, Agent, or Firm* — McCarter & English, LLP

(57) ABSTRACT

The present disclosure provides a variety of methods and compositions useful for making, sterilizing, and preserving tissues. The disclosure also features the acellular tissue matrices made by the methods.

34 Claims, 16 Drawing Sheets

(56) References Cited

U.S. PATENT DOCUMENTS

| | | | |
|---|---|---|---|
| 4,357,274 A | 11/1982 | Werner | |
| 4,412,947 A | 11/1983 | Cioca | |
| 4,776,853 A | 10/1988 | Klement et al. | |
| 4,801,299 A | 1/1989 | Brendel et al. | |
| 5,149,295 A | 9/1992 | Bowling et al. | |
| 5,290,558 A | 3/1994 | O'Leary et al. | |
| 5,298,254 A | 3/1994 | Prewett et al. | |
| 5,336,616 A | 8/1994 | Livesey et al. | |
| 5,364,756 A | 11/1994 | Livesey et al. | |
| 5,374,539 A | 12/1994 | Nimni et al. | |
| 5,460,962 A | 10/1995 | Kemp | |
| 5,507,810 A | 4/1996 | Prewett et al. | |
| 5,514,536 A | 5/1996 | Taylor | |
| 5,558,875 A | 9/1996 | Wang | |
| 5,613,982 A | 3/1997 | Goldstein | |
| 5,622,867 A | 4/1997 | Livesey et al. | |
| 5,669,916 A | 9/1997 | Anderson | |
| 5,780,295 A | 7/1998 | Livesey et al. | |
| 5,782,915 A | 7/1998 | Stone | |
| 5,843,182 A | 12/1998 | Goldstein | |
| 5,919,614 A | 7/1999 | Livesey et al. | |
| 5,944,755 A | 8/1999 | Stone | |
| 6,110,206 A | 8/2000 | Stone | |
| 6,114,107 A | 9/2000 | Wiggins et al. | |
| 6,152,142 A | 11/2000 | Tseng | |
| 6,194,136 B1 | 2/2001 | Livesey et al. | |
| 6,206,931 B1 | 3/2001 | Cook et al. | |
| 6,221,669 B1 | 4/2001 | Livesey et al. | |
| 6,241,981 B1 | 6/2001 | Cobb et al. | |
| 6,293,970 B1 | 9/2001 | Wolfinbarger, Jr. et al. | |
| 6,352,708 B1 | 3/2002 | Duran et al. | |
| 6,368,656 B1 | 4/2002 | Lefebvre et al. | |
| 6,376,244 B1 | 4/2002 | Atala | |
| 6,381,026 B1 | 4/2002 | Schiff et al. | |
| 6,432,712 B1 | 8/2002 | Wolfinbarger, Jr. | |
| 6,448,076 B2 | 9/2002 | Dennis et al. | |
| 6,478,493 B1 | 11/2002 | Cepeda et al. | |
| 6,478,494 B1 | 11/2002 | Eckl et al. | |
| 6,478,496 B1 | 11/2002 | Yoshii et al. | |
| 6,478,497 B2 | 11/2002 | Villahoz | |
| 6,478,498 B1 | 11/2002 | Miyasaka et al. | |
| 6,569,200 B2 | 5/2003 | Wolfinbarger, Jr. et al. | |
| 6,630,001 B2 | 10/2003 | Duran et al. | |
| 6,734,018 B2 | 5/2004 | Wolfinbarger, Jr. et al. | |
| 6,743,574 B1 | 6/2004 | Wolfinbarger, Jr. et al. | |
| 6,793,939 B2 | 9/2004 | Badylak | |
| 6,866,686 B2 | 3/2005 | Ollerenshaw et al. | |
| 6,919,172 B2 | 7/2005 | DePablo et al. | |
| 6,933,326 B1 | 8/2005 | Griffey et al. | |
| 7,008,763 B2 | 3/2006 | Cheung | |
| 7,060,103 B2 | 6/2006 | Carr, Jr. et al. | |
| 7,063,726 B2 | 6/2006 | Crouch et al. | |
| 7,169,606 B2 | 1/2007 | DePablo et al. | |
| 7,498,412 B2 | 3/2009 | Huang et al. | |
| 7,585,461 B2 | 9/2009 | Shimp et al. | |
| 8,563,232 B2 | 10/2013 | Wolfinbarger, Jr. et al. | |
| 8,735,054 B1 | 5/2014 | Sun et al. | |
| 8,828,448 B2 * | 9/2014 | Korossis | A61L 27/3687 424/558 |
| 9,150,318 B1 | 10/2015 | Sun et al. | |
| 10,322,835 B1 | 6/2019 | Sun et al. | |
| 2001/0000804 A1 | 5/2001 | Goldstein et al. | |
| 2001/0004715 A1 | 6/2001 | Duran et al. | |
| 2001/0014579 A1 | 8/2001 | Potter et al. | |
| 2001/0049138 A1 | 12/2001 | Dennis et al. | |
| 2002/0031994 A1 | 3/2002 | Potter et al. | |
| 2002/0128724 A1 | 9/2002 | Ollerenshaw et al. | |
| 2002/0173260 A1 | 11/2002 | Potter et al. | |
| 2003/0027125 A1 | 2/2003 | Mills et al. | |
| 2003/0035843 A1 | 2/2003 | Livesey et al. | |
| 2003/0054022 A1 | 3/2003 | Spievack | |
| 2003/0073399 A1 | 4/2003 | Potter et al. | |
| 2003/0087428 A1 | 5/2003 | Wolfinbarger et al. | |
| 2003/0135284 A1 | 7/2003 | Crouch et al. | |
| 2003/0143207 A1 | 7/2003 | Livesey et al. | |
| 2003/0185702 A1 | 10/2003 | Burgess et al. | |
| 2003/0206860 A1 | 11/2003 | Bleyer et al. | |
| 2004/0037735 A1 | 2/2004 | DePaula et al. | |
| 2004/0057936 A1 | 3/2004 | Cheung | |
| 2004/0067582 A1 | 4/2004 | Wolfinbarger et al. | |
| 2004/0076657 A1 | 4/2004 | Wolfinbarger et al. | |
| 2004/0209235 A1 | 10/2004 | Goldstein et al. | |
| 2004/0219058 A1 | 11/2004 | Shimp et al. | |
| 2005/0028228 A1 | 2/2005 | McQuillan et al. | |
| 2005/0045614 A1 | 3/2005 | Hayzlett et al. | |
| 2005/0160701 A1 | 7/2005 | Stevens | |
| 2005/0260176 A1 | 11/2005 | Ayares et al. | |
| 2005/0260612 A1 | 11/2005 | Padmini et al. | |
| 2006/0073592 A1 | 4/2006 | Sun et al. | |
| 2006/0127375 A1 | 6/2006 | Livesey et al. | |
| 2006/0127495 A1 | 6/2006 | Cheung | |
| 2006/0210960 A1 | 9/2006 | Livesey et al. | |
| 2007/0014773 A1 | 1/2007 | Matheny et al. | |
| 2007/0208354 A1 | 9/2007 | Barraclough et al. | |
| 2007/0225733 A1 | 9/2007 | Barraclough et al. | |
| 2007/0248575 A1 | 10/2007 | Connor et al. | |
| 2008/0004657 A1 | 1/2008 | Obermiller et al. | |
| 2008/0188945 A1 | 8/2008 | Boyce et al. | |
| 2009/0180965 A1 | 7/2009 | Freyman et al. | |
| 2009/0311298 A1 | 12/2009 | Nixon et al. | |
| 2014/0154663 A1 | 6/2014 | Wolfinbarger et al. | |
| 2015/0050247 A1 | 2/2015 | Machluf et al. | |

FOREIGN PATENT DOCUMENTS

| | | |
|---|---|---|
| WO | WO-96/14738 A2 | 5/1996 |
| WO | WO-2004/052098 A1 | 6/2004 |
| WO | WO-2004/093541 A1 | 11/2004 |
| WO | WO-2007/110634 A2 | 10/2007 |

OTHER PUBLICATIONS

American Association of Tissue Banks: Standards for Tissue Banking. 130 pages, (1996).

American Association of Tissue Banks: Technical Manual for Skin Banking, 26 pages (1992).

American Association of Tissue Banks: Technical Manual Musculoskeletal Tissues, 4 pages (1992).

Basile, A comparative study of glycerinized and lyophilized porcine skin in dressings for third-degree burns. Plast Reconstr Surg. Jun. 1982;69(6):969-74.

Beard, More ways devised for skin replacement. The Houston Chronicle. 5 pages, Mar. 21, 1994.

Ben-Bassat, Performance and safety of skin allografts. Clin Dermatol. Jul.-Aug. 2005;23(4):365-75.

Billingham et al., The Freezing, Drying and Storage of Mammalian Skin. Journal of Experimental Biology. 1952;29:454-468.

Bourroul et al., Sterilization of skin allografts by ionizing radiation. Cell Mol Biol (Noisy-le-grand). Nov. 2002;48(7):803-7.

Brans et al., Long-term results of treatment of scalds in children with glycerol-preserved allografts. Burns. 1994;20 Suppl 1:S10-3.

Clark et al., Decellularized dermal grafting in cleft palate repair. Arch Facial Plast Surg. Jan.-Feb. 2003;5(1):40-4.

Conklin et al., Development and evaluation of a novel decellularized vascular xenograft. Med Eng Phys. Apr. 2002;24(3):173-83.

Courtman et al., Biomechanical and ultrastructural comparison of cryopreservation and a novel cellular extraction of porcine aortic valve leaflets. J Biomed Mater Res. Dec. 1995;29(12):1507-16.

Courtman et al., Development of a pericardial acellular matrix biomaterial: biochemical and mechanical effects of cell extraction. J Biomed Mater Res. Jun. 1994;28(6):655-66.

Courtman et al., The Acellular Matrix Vascular Prosthesis: Investigation of its Potential as a Xenograft for Clinical Application. Biomaterial Tissues Interfaces. pp. 241-246. (1992).

Courts, Structural changes in collagen. 2. Enhanced solubility of bovine collagen: reactions with hydrogen peroxide and some properties of soluble eucollagen. Biochem J. Nov. 1961;81:356-65.

De Backere, Euro Skin Bank: large scale skin-banking in Europe based on glycerol-preservation of donor skin. Burns. 1994;20 Suppl 1:S4-9.

(56) References Cited

OTHER PUBLICATIONS

Elkins et al., Decellularized Human Valve Allografts. Ann Thorac Surg. 2001;71:S428-32.
Freytes Do et al. "Effect of storage upon material properties of lyophilized porcine extracellular matrix derived from the urinary bladder." J Biomed Mater Res B Appl Biomater. Aug. 2006;78(2):327-33.
Freytes Do et al. "Uniaxial and biaxial properties of terminally sterilized porcine urinary bladder matrix scaffolds." J Biomed Mater Res B Appl Biomater. Feb. 2008;84(2):408-14.
Ge et al., Skin Graft Preservation. Skin Grafts—Indications, Applications and Current Research. Marcia Spear (Ed.), InTech. Chapter 13, pp. 159-174.
Gilbert et al., Decellularization of tissues and organs. Biomaterials. Jul. 2006;27(19):3675-83.
Grieb et al., Effective use of optimized, high-dose (50 kGy) gamma irradiation for pathogen inactivation of human bone allografts. Biomaterials. May 2005;26(14):2033-42.
Grieb et al., High-dose gamma irradiation for soft tissue allografts: High margin of safety with biomechanical integrity. J Orthop Res. May 2006;24(5):1011-8.
Hermans, Clinical experience with glycerol-preserved donor skin treatment in partial thickness burns. Burns Incl Therm Inj. Feb. 1989;15(1):57-9.
Hettich et al., The immunogenicity of glycerol-preserved donor skin. Burns. 1994;20 Suppl 1:S71-5; discussion S75-6.
Hoekstra et al., History of the Euro Skin Bank: the innovation of preservation technologies. Burns. 1994;20 Suppl 1:S43-7.
Huang et al., Banking of non-viable skin allografts using high concentrations of glycerol or propylene glycol. Cell Tissue Bank. 2004;5(1):3-21.
Huang et al., Use of peracetic acid to sterilize human donor skin for production of acellular dermal matrices for clinical use. Wound Repair Regen. May-Jun. 2004;12(3):276-87.
King, The Use of Preserved Ocular Tissues for Transplantation. Transactions of the American Ophthalmologial Society. American Ophthalmological Society by University of Toronto Press, Toronto. pp. 203-216, (1959).
Knobloch et al., Retinal Detachment Surgery with Preserved Human Sclera. Am J Ophthalmol. Aug. 1985;60:191-204.
Kreis et al., Historical appraisal of the use of skin allografts in the treatment of extensive full skin thickness burns at the Red Cross Hospital Burns Centre, Beverwijk, The Netherlands. Burns. 1992;18 Suppl 2:S19-22.
Kreis et al., The use of non-viable glycerol-preserved cadaver skin combined with widely expanded autografts in the treatment of extensive third-degree burns. J Trauma. Jan. 1989;29(1):51-4.
Krejci NC et al. "In vitro reconstitution of skin: fibroblasts facilitate keratinocyte growth and differentiation on acellular reticular dermis." J. Invest Dermatol. Nov. 1991;97(5):843-8.
Leigh et al., Skin Equivalents and Cultued Skin: From the Petri Dish to the Patient. Wounds: A Compendium of Clinical Research and Practice. Jul./Aug. 1991;3(4):141-148.
Lins et al., Trehalose-protein interaction in aqueous solution. Proteins. Apr. 1, 2004;55(1):177-86.
Livesey et al., Transplanted acellular allograft dermal matrix. Potential as a template for the reconstruction of viable dermis. Transplantation. Jul. 15, 1995;60(1):1-9.
Mackie, The Euro Skin Bank: development and application of glycerol-preserved allografts. J Burn Care Rehabil. Jan.-Feb. 1997;18(1 Pt 2):S7-9.
Maral et al., Effectiveness of human amnion preserved long-term in glycerol as a temporary biological dressing. Burns. Nov. 1997;25(7):625-35.
May et al., Reduced bacteria on transplantable allograft skin after preparation with chlorhexidine gluconate. povidone-iodine, and isopropanol. J Burn Care Rehabil. May-Jun. 1991;12(3):224-8.

Mckay et al., Reconstruction of human skin from glycerol-preserved allodermis and cultured keratinocyte sheets. Burns. 1994;20 Suppl 1:S19-22.
Na, Interaction of calf skin collagen with glycerol: linked function analysis. Biochemistry. Mar. 11, 1986;25(5):967-73.
Ninnemann et al., Clinical skin banking: a simplified system for processing, storage, and retrieval of human allografts. J Trauma. Oct. 1978;18(10):723-5.
Okamoto et al., Autogenous transplantation of rib cartilage preserved in glycerol, after removal of the perichondrium, to the malar process of rats—a histological study (Part I). J. Nihon Univ Sch Dent. Jun. 1990;32(2):116-26.
Oliver et al., Histological studies of subcutaneous and intraperitoneal implants of trypsin-prepared dermal collagen allografts in the rat. Clin Orthop Relat Res. Mar.-Apr. 1976;(115):291-302.
Parker et al., Storage of heart valve allografts in glycerol with subsequent antibiotic sterilisation. Thorax. Oct. 1978;33(5):638-45.
Penkova et al., Stablizing Effect of Glycerol on Collagen Type I Isolated from Different Species. Food Chemistry. 1999;66:483-487.
Puig et al., Four years experience with dura mater cardiac valves. J Cardiovasc Surg (Torino). May-Jun. 1977;18(3):247-55.
Ravishanker et al., "Amnion Bank"—the use of long term glycerol preserved amniotic membranes in the management of superficial and superficial partial thickness burns. Burns. Jun. 2003;29(4):369-74.
Richters et al., Immunogenicity of glycerol-preserved human cadaver skin in vitro. J Burn Care Rehabil. May-Jun. 1997;18(3):228-33.
Richters et al., Morphology of glycerol-preserved human cadaver skin. Burns. Mar. 1996;22(2):1 13-6.
Rieder et al., Decellularization protocols of porcine heart valves differ importantly in efficiency of cell removal and susceptibility of the matrix to recellularization with human vascular cells. J Thorac Cardiovasc Surg. Feb. 2004;127(2):399-405.
Rooney et al., Sterilisation of skin allograft with gamma irradiation. Burns. Aug. 2008;34(5):664-73.
Sabates et al., Experimental and clinical studies of glycerin preserved scleral homografts. (A preliminary report). Eye Ear Nose Throat Mon. Sep. 1967;46(9):1162-6.
Schwade, Implants, Soft Tissue. AlloDerm. Retrieved online at: emedicine.com. 11 pages. Jun. 20, 2002.
Sun, Effects of Glycerol, Sucrose and Trehalose on Cryopreserved Human Dermis Against Gamma Irradiation Damage. Cryobiology. 2008;57:330. Abstract No. 74.
Van Baare et al., Microbiological evaluation of glycerolized cadaveric donor skin. Transplantation. Apr. 15, 1998;65(7):966-70.
Van Baare et al., Virucidal effect of glycerol as used in donor skin preservation. Burns. 1994;20 Suppl 1:S77-80.
Wainwright et al., Clinical evaluation of an acellular allograft dermal matrix in full-thickness burns. J Burn Care Rehabil. Mar.-Apr. 1996;17(2):124-36.
Wilson et al., Acellular matrix allograft small caliber vascular prostheses. ASAIO Trans. Jul.-Sep. 1990;36(3):M340-3.
Wilson et al., Acellular matrix: a biomaterials approach for coronary artery bypass and heart valve replacement. Ann Thorac Surg. Aug. 1995;60(2 Suppl):S353-8.
Yoshinaga et al., Protection by trehalose of DNA from radiation damage. Biosci Biotechnol Biochem. Jan. 1997;61(1):160-1.
Appeal Brief Under Board Rule § 41.37 dated Jul. 26, 2010, in U.S. Appl. No. 10/959,780, filed Oct. 6, 2004.
Decision on Appeal mailed Jan. 23, 2012, in U.S. Appl. No. 10/959,780, filed Oct. 6, 2004.
Examiner's Answer dated Oct. 28, 2010, in U.S. Appl. No. 10/959,780, filed Oct. 6, 2004.
Office Action dated Aug. 17, 2012, in U.S. Appl. No. 12/348,188, filed Jan. 2, 2009.
Reply Brief Under 37 C.F.R. § 41.41 dated Dec. 28, 2010, in U.S. Appl. No. 10/959,780, filed Oct. 6, 2004.
Response to Notification of Non-Compliant Appeal Brief dated Aug. 13, 2010, in U.S. Appl. No. 10/959,780, filed Oct. 6, 2004.

* cited by examiner

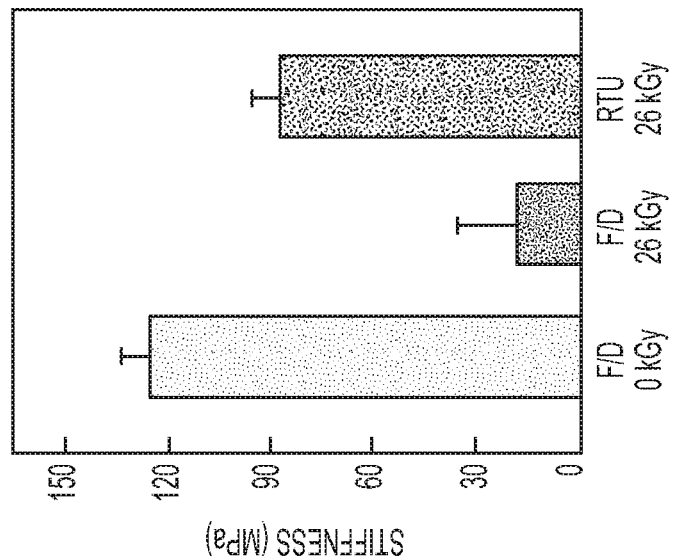
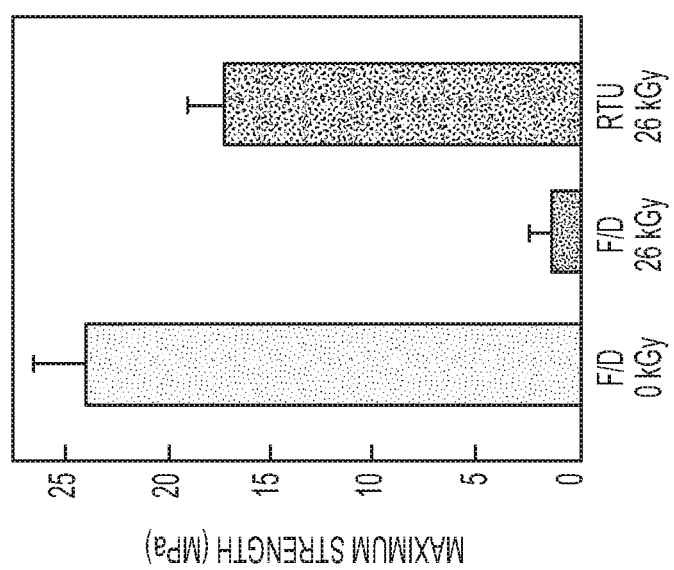

METHOD FOR PREPARING COLLAGEN-BASED MATERIALS

This application is a continuation of U.S. patent application Ser. No. 14/836,508 which was on filed Aug. 26, 2015, which is a continuation of U.S. patent application Ser. No. 12/650,902, which was filed on Dec. 31, 2009, now U.S. Pat. No. 9,150,318, which was granted on Oct. 6, 2015, which claims priority to U.S. Provisional Patent Application No. 61/142,308, which was filed on Jan. 2, 2009, all of which are herein incorporated by reference in their entirety.

The present disclosure pertains generally to acellular tissue matrices, and to methods for preparing acellular tissue matrices.

Tissue matrices derived from various collagen-based tissues can be used to treat a variety of conditions. Such tissues, when implanted in humans or other animals, must be sterilized to prevent disease transmission through bacteria, viruses, or other pathogens. In addition, such tissues must maintain desired biologic properties and sterility during and after processing and sterilization. The present disclosure provides methods for processing, sterilizing, and/or storing tissue matrices, as well as various compositions for use with such methods.

SUMMARY

In certain embodiments, a method for sterilizing a tissue matrix is provided. The method comprises contacting an acellular collagen-based tissue matrix from a mammal with a first solution comprising peracetic acid (PAA). The method further comprises contacting the tissue matrix with a protective solution effective to stabilize the tissue matrix during and after exposure to irradiation and packaging the tissue matrix in a sealed pouch. The tissue matrix may be exposed to an irradiation dose to sterilize the tissue matrix.

In certain embodiments, a method for preparing an acellular tissue matrix (ATM) is provided. The method comprises removing substantially all of the cells from a tissue sample of a mammal resulting in a decellularized tissue matrix and contacting the decellularized tissue matrix with a DNA nuclease that removes substantially all of the DNA from the decellularized tissue matrix. The method further comprises contacting the decellularized tissue matrix with a solution comprising peracetic acid (PAA) and contacting the decellularized tissue matrix with a protective solution effective to stabilize the tissue matrix during and after exposure to irradiation. The decellularized tissue matrix is exposed to an irradiation dose effective to sterilize the tissue matrix.

In certain embodiments, a solution is provided. The solution comprises: a biocompatible buffer; a salt at a concentration of up to about 150 mM (milliMolar) in the solution; a surfactant in an amount of about 0.2% or less of the solution; a transition-metal chelator at a concentration of between about 1 mM to about 10 mM; a tissue stabilizer in an amount of up to about 10% (w/v) (weight/volume) of the solution; and a biocompatible co-solute in an amount of up to about 20% (w/v) of the solution, wherein the solution has a pH of between about 5.2 to about 6.9 and the solution has a water activity of between about 0.930 to about 0.995.

BRIEF DESCRIPTION OF THE DRAWINGS

FIGS. 6A and 6B are a pair of bar graphs depicting the tensile strength and stiffness of Yucatan porcine tissue matrix after gamma irradiation, according to certain embodiments.

DETAILED DESCRIPTION

Figure 1A:
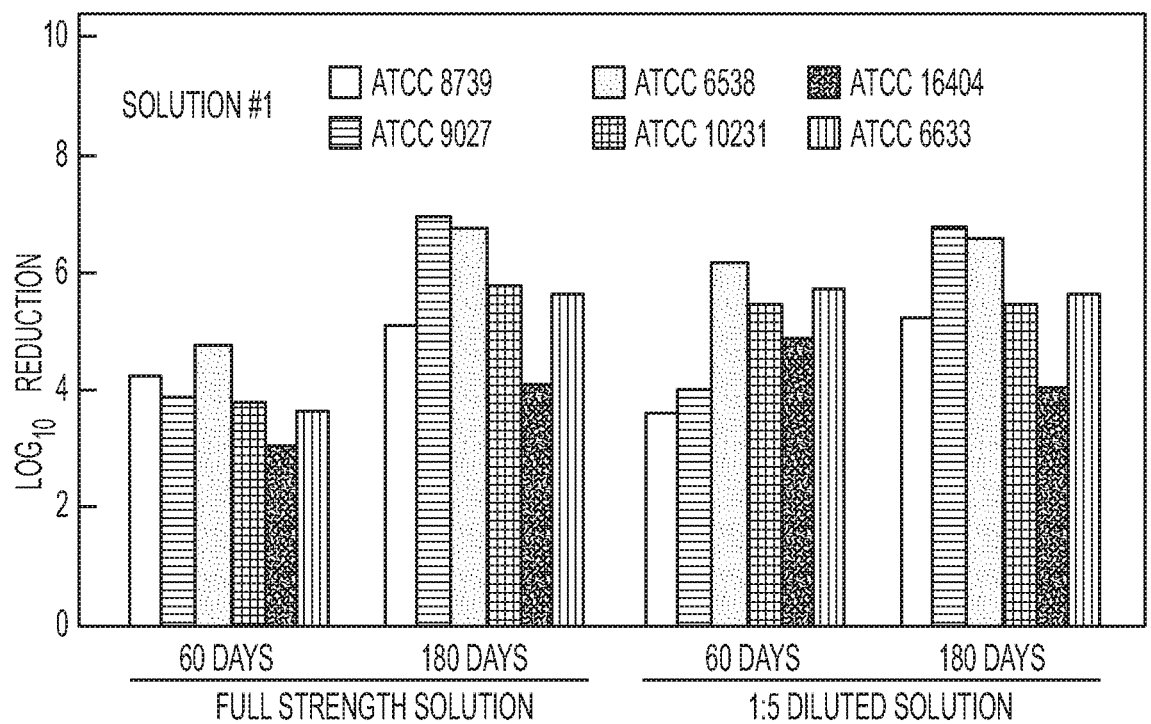
FIGS. 1A and 1B are a pair of bar graphs depicting the antimicrobial activity of two exemplary preservation solution formulations, according to certain embodiments.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Any range described herein will be understood to include the endpoints and all values between the endpoints. All documents, or portions of documents, cited in this application, including but not limited to patents, patent applications, articles, books, and treatises, are hereby expressly incorporated by reference in their entirety for any purpose.

The present disclosure provides methods and compositions useful for producing, sterilizing, and packaging acellular tissue matrices. In some embodiments, acellular tissue matrices that are made by any of the methods described herein are provided. In some embodiments, such acellular tissue matrices can be used to treat injury to, or repair, a large number of tissues and/or organs in a mammal (e.g., a human). For example, the matrices can be used to repair injuries to fascia, bone, and/or cartilage.

The disclosure also provides compositions (e.g., solutions) and methods for sterilizing and preserving tissues and/or decellularized tissue matrices. In certain embodiments, the methods can be used alone or in conjunction with the methods of making acellular tissue matrices.

Exemplary methods for making and preserving acellular tissue matrices as well as applications in which the matrices can be used are set forth below.

Acellular Tissue Matrices

As used herein, an "acellular tissue matrix" ("ATM"), "tissue matrix," or decellularized tissue (each used interchangeably) is a tissue-derived structure that is made from any of a wide range of collagen-containing tissues by removing all, or substantially all, viable cells and all detectable subcellular components and/or debris generated by killing or lysing cells. As used herein, "lacking substantially all viable cells" means that the concentration of viable cells is less than 1% (e.g., 1%, 0.9%, 0.8%, 0.7%, 0.6%, 0.5%, 0.4%, 0.3%, 0.2%, 0.1%; 0.01%; 0.001%; 0.0001%; 0.00001%; 0.000001%, or any value between) of that in the tissue or organ from which the ATM was made. However, decellularized tissues may be reseeded with cells from other sources, e.g., after processing to produce an ATM, in order to support tissue regeneration or repair.

In some embodiments, the ATM is treated in such a way as to remove all, or substantially all, of the DNA in the tissue. As used herein, an ATM lacking "substantially all DNA" is an ATM in which the concentration of DNA is less than 1% (e.g., less than: 1%, 0.9%, 0.8%, 0.7%, 0.6%, 0.5%, 0.4%, 0.3%, 0.2%, 0.1%; 0.01%; 0.001%; 0.0001%; 0.00001%; or 0.000001%) of that in the tissue or organ from which the ATM was made. This includes all DNA (e.g., DNA within intact cells (alive or dead cells) or residual DNA material left from the decellularization process).

In some embodiments, the ATM can lack, or substantially lack, an epithelial basement membrane. The epithelial basement membrane is a thin sheet of extracellular material contiguous with the basilar aspect of epithelial cells. Sheets of aggregated epithelial cells form an epithelium. Thus, for example, the epithelium of skin is called the epidermis, and the skin epithelial basement membrane lies between the epidermis and the dermis. The epithelial basement membrane is a specialized extracellular matrix that provides a barrier function and an attachment surface for epithelial-like cells; however, it does not contribute any significant structural or biomechanical role to the underlying tissue (e.g., dermis). Unique components of epithelial basement membranes include, for example, laminin, collagen type VII, and nidogen. The unique temporal and spatial organization of the epithelial basement membrane distinguish it from, e.g., the dermal extracellular matrix. The presence of the epithelial basement membrane in an ATM could be disadvantageous in that the epithelial basement membrane likely contains a variety of species-specific components that would elicit the production of antibodies, and/or bind to preformed antibodies, in xenogeneic graft recipients of the acellular matrix. In addition, the epithelial basement membrane can act as barrier to diffusion of cells and/or soluble factors (e.g., chemoattractants) and to cell infiltration. Its presence in ATM grafts can thus significantly delay formation of new tissue from the acellular tissue matrix in a recipient animal.

In some embodiments, the ATM will retain certain biological functions. In certain embodiments, the biological functions retained by ATM include cell recognition and cell binding as well as the ability to support cell spreading, cell proliferation, and cell differentiation. Such functions are provided by undenatured collagenous proteins (e.g., type I collagen) and a variety of non-collagenous molecules (e.g., proteins that serve as ligands for either molecules such as integrin receptors, molecules with high charge density such as glycosaminoglycans (e.g., hyaluronan) or proteoglycans, or other adhesins). As detailed in the accompanying Examples, in certain embodiments, ATMs produced by the methods described herein possess an ability to induce cellular repopulation and revascularization at the site of implantation. Thus, in some embodiments, an ATM produced by the methods described herein can support cellular repopulation or revascularization at a site of implantation that is at least 50% (e.g., at least: 50%; 60%; 70%; 80%; 90%; 95%; 98%; 99%; 99.5%; 100%; or more than 100%) of the number of cells (but not necessarily the type of cells) or of the level of vascularization (respectively) of the native tissue or organ from which the ATM is made.

Suitable methods for measuring the efficiency of the biological functions of an ATM are set forth in the accompanying Examples. In some embodiments, the efficacy of the biological functions of an ATM can be measured by the ability of the ATM to support cell proliferation and is at least 50% (e.g., at least: 50%; 60%; 70%; 80%; 90%; 95%; 98%; 99%; 99.5%; 100%; or more than 100%) of that of the native tissue or organ from which the ATM is made.

In certain embodiments, structural functions retained by useful acellular matrices include maintenance of histological architecture, maintenance of the three-dimensional array of the tissue's components and physical characteristics such as strength, elasticity, and durability, defined porosity, and retention of macromolecules.

In some embodiments, it is not necessary that the grafted matrix material be made from tissue that is identical to the surrounding host tissue, but should simply be amenable to being remodeled by invading or infiltrating cells such as differentiated cells of the relevant host tissue, stem cells such as mesenchymal stem cells, or progenitor cells. Remodeling is directed by the above-described ATM components and signals from the surrounding host tissue (such as cytokines, extracellular matrix components, biomechanical stimuli, and bioelectrical stimuli). The presence of mesenchymal stem cells in the bone marrow and the peripheral circulation has been documented in the literature and shown to regenerate a variety of musculoskeletal tissues (Caplan (1991) J. Orthop. Res. 9:641-650; Caplan (1994) Clin. Plast. Surg. 21:429-435; and Caplan et al. (1997) Clin Orthop. 342:254-269). Additionally, in some embodiments, the graft must provide some degree (greater than threshold) of tensile and biomechanical strength during the remodeling process.

In certain embodiments, the ATM can be produced from any collagen-containing soft tissue and musculo-skeletal tissue (e.g., dermis, fascia, pericardium, dura, umbilical cords, placentae, cardiac valves, ligaments, tendons, vascular tissue (arteries and veins such as saphenous veins), neural connective tissue, urinary bladder tissue, ureter tissue, or intestinal tissue), as long as the above-described properties are retained by the matrix. Moreover, in certain embodiments, the tissues in which the above ATMs are placed include essentially any tissue that can be remodeled by invading or infiltrating cells. Relevant tissues include, without limitation, skeletal tissues such as bone, cartilage, ligaments, fascia, and tendon. Other tissues in which any of the above allografts can be placed include, without limitation, skin, gingiva, dura, myocardium, vascular tissue, neural tissue, striated muscle, smooth muscle, bladder wall, ureter tissue, intestine, and urethra tissue.

Furthermore, in some embodiments, an ATM can have been made from one or more individuals of the same species as the recipient of the ATM graft. Alternatively, in certain embodiments, an ATM can have been made from a porcine tissue, or other animal source, and can be implanted in a human patient. Species that can serve as recipients of ATM and donors of tissues or organs for the production of the ATM include, without limitation, humans, non-human primates (e.g., monkeys, baboons, or chimpanzees), porcine, bovine, horses, goats, sheep, dogs, cats, rabbits, guinea pigs, gerbils, hamsters, rats, or mice. In certain embodiments, the donors are animals (e.g., pigs) that have been genetically engineered to lack the terminal galactose-α-1-3-galactose moiety, or alternatively, tissue samples from such animals can be treated with an agent (such as alpha-galactosidase) to remove all, or substantially all, of the terminal galactose-α-α-1-3-galactose moieties from the tissue (see below under "Methods for Making an ATM"). For descriptions of appropriate animals, see co-pending U.S. application Ser. No. 10/896,594 and U.S. Pat. No. 6,166,288, the disclosures of all of which are incorporated herein by reference in their entirety. In addition, certain exemplary methods of processing tissues to produce acellular matrices with or without reduced amounts of or lacking alpha-1,3-galactose moieties, are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," *Tissue Engineering*, Vol. 15, 1-13 (2009), which is incorporated by reference in its entirety.

In some embodiments, the form in which the ATM is provided will depend on the tissue or organ from which it is derived and on the nature of the recipient tissue or organ, as well as the nature of the damage or defect in the recipient tissue or organ. Thus, for example, a matrix derived from a heart valve can be provided as a whole valve, as small sheets or strips, as pieces cut into any of a variety of shapes and/or sizes, or in a particulate form. The same concept applies to ATM produced from any of the above-listed tissues and organs. It is understood that an ATM can be made from a recipients own collagen-based tissue.

Methods for Making an ATM

One exemplary method for making (or preparing) an ATM can include the steps of: providing a tissue sample from a mammal; removing all, or substantially all, of the cells from the tissue sample resulting in a decellularized tissue; and contacting the decellularized tissue with a DNA nuclease that removes all, or substantially all, of the DNA from the decellularized tissue, thereby resulting in an ATM.

Decellularization of a tissue can be accomplished using a number of chemical or enzymatic treatments known in the art and described in, e.g., U.S. Pat. No. 5,336,616 (the disclosure of which is incorporated by reference in its entirety). For example, in some embodiments, cells can be removed from a tissue by incubating the tissue in a processing solution containing certain salts (e.g., high concentrations of salts), detergents (e.g., mild or strong detergents), enzymes, or combinations of any of the foregoing. Strong detergents include, e.g., ionic detergents such as, but not limited to: sodium dodecyl sulfate, sodium deoxycholate, and 3-[(3-chloramidopropyl)-dimethylammino]-1-propanesulfonate. Mild detergents include, e.g., polyoxyethylene (20) sorbitan mono-oleate and polyoxyethylene (80) sorbitan mono-oleate (TWEEN-20® and TWEEN-80®), saponin, digitonin, TRITON X-100™ (polyethylene glycol p-(1,1,3,3-tetramethylbutyl)-phenyl ether), CHAPS (3-[(3-Cholamidopropyl)dimethylammonio]-1-Propanesulfonate), and NONIDET-40 (NP40) (octylphenoxypolyethoxyethanol). The use of the detergent TRITON X-100™, a trademarked product of Rohm and Haas Company of Philadelphia, Pa., has been demonstrated to remove cellular membranes, as detailed in U.S. Pat. No. 4,801,299, the entire contents of which are incorporated by reference in their entirety.

In some embodiments, decellularization can be accomplished using a variety of lysogenic enzymes including, but not limited to, dispase II, trypsin, and thermolysin. In certain embodiments, to minimize any potential adverse proteolytic effects on the extracellular matrix, the concentration, temperature, and the amount of time the enzymatic reaction is allowed to proceed should be carefully monitored. Such optimization of these reactions (e.g., for a particular tissue type) is well within the capability of one of ordinary skill in the art.

In some embodiments, low salt concentrations can also be used to decellularize tissue through osmotic disregulation of the cells contained therein. Alternatively, in some embodiments, where the tissue sample is a skin sample, high salt concentrations can be used to separate the epidermis from the dermis of the skin. For example, Livesey et al. (U.S. Pat. No. 5,336,616, supra) describes that incubation of a skin sample in 1 M sodium chloride for approximately 16 hours for human skin and approximately 48 hours for porcine skin will routinely allow clean separation of the epidermis and dermis without damage to the basement membrane complex.

In addition to salts, detergents, and enzymes, the processing solution used to decellularize a tissue can also contain a battery of certain inhibitors (e.g., protease inhibitors) to prevent degradation of the extracellular matrix. The processing solution can also contain one or more protease inhibitors selected from the group consisting of N-ethylmaleimide (NEM), phenylmethylsulfonylfluoride (PMSF) ethylenediamine tetraacetic acid (EDTA), ethylene glycol-bis-(2-aminoethyl(ether)NNN'N'-tetraacetic acid, ammonium chloride, elevated pH, apoprotinin, and leupeptin.

In some embodiments, the processing solutions can also contain an appropriate buffer. Suitable buffers include any of a variety of biocompatible buffers such as, but not limited to, 2-(N-morpholino)ethanesulfonic acid (MES), Tris (hydroxymethyl)aminomethane (TRIS), (N-[2-hydroxyethyl] piperazine-N'-[2-ethanesulfonic acid] (HEPES), or a buffer containing phosphate, bicarbonate, acetate, citrate, or glutamate, with or without glycine.

A tissue can be treated with a processing solution containing one or more (e.g., two, three, four, five, six, seven, eight, nine, or 10 or more) different enzymes, detergents, salts (e.g., high or low concentrations or different salt combinations), or combinations of any of the foregoing. For example, a processing solution can contain a mild detergent and a strong detergent or two mild detergents and an enzyme.

In certain embodiments, a tissue can be treated once or more than once (e.g., two, three, three, four, five, six, seven, eight, nine, or 10 or more times) with a processing solution. In some embodiments, a tissue can be treated more than one time with the same processing solution or can be treated with several different processing solutions in series. For example, a tissue can be treated with one processing solution multiple times, or the tissue can be treated with a first processing solution and subsequently with a second processing solution.

As the processing solution can contain chemicals or agents that would be irritating or inflammatory when administered to a mammalian subject, washing can be performed to substantially remove the processing solution from the tissue. In some embodiments, a tissue can be washed one or more (e.g., two, three, four, five, six, or more than seven) times following treatment with a processing solution, or the tissue can be washed one or more times between processing solution treatments. For example, a tissue can be treated with a first processing solution and then washed three times before treatment with a second processing solution. Alternatively, rather than or in addition to, components of the processing solution may be neutralized by specific inhibitors, e.g., dispase II by ethylenediaminetetraacetic acid (EDTA) or trypsin by serum.

Methods for determining the extent of decellularization are known in the art and include, e.g., cell-counting/trypan blue exclusion assays (on any cells collected from a treated tissue) or various microscopy methods such as direct immunostaining of a decellularized tissue section using antibodies that bind to specific cell markers (e.g., markers of the cell nucleus, mitochondria, or cell cytoplasm). Such methods are described in, e.g., Ramos-Vara, J A (2005) *Vet Pathol* 42: 405-426 and Hayat (2002) *Microscopy, Immunohistochemistry, and Antigen Retrieval Methods: For Light and Electron Microscopy*, $1^{st}$ Ed. Springer, the disclosures of each of which are incorporated by reference in their entirety.

In some embodiments, following the decellularization process described above, a decellularized tissue matrix can be contacted with one or more solutions containing a DNA nuclease to remove all, or substantially all, of the DNA. The DNA nuclease can be a DNA exonuclease, a DNA endonuclease, or a DNA nuclease that possesses both activities. For example, a solution for removing DNA in a decellularized tissue can include DNase I, Exonuclease III, Mung bean nuclease, or Nuclease BAL 31. Suitable reaction conditions for removing DNA from a tissue include incubating the tissue in a buffered solution containing the DNA nuclease and a divalent cation such as magnesium (or manganese), at a physiologic pH (e.g., 7.5) and temperature (e.g., 37° C.), for about 5 minutes or more (e.g., about 10 minutes, about 20 minutes, about 30 minutes, about 40 minutes, about 50 minutes, about an hour, about 1.5 hours, about 2 hours, about 2.5 hours, about 3 hours, about 3.5 hours, about 4 hours, or about 4.5 hours or more).

In certain embodiments, a decellularized tissue can be treated with a solution containing one or more (e.g., two, three, four, five, six, seven, eight, nine, or 10 or more) different DNA nucleases such as any of those described herein or known in the art. For example, a solution can contain a mixture of DNase I, Exonuclease III, and Mung bean nuclease. In some embodiments, a tissue can be treated more than one time with the same DNA nuclease solution or can be treated with several different DNA nuclease solutions. For example, a tissue can be treated with one DNA nuclease solution multiple times, or the tissue can be treated with a first DNA nuclease solution and then subsequently with a second DNA nuclease solution.

In some embodiments, a tissue can be washed one or more (e.g., two, three, four, five, six, or more than seven) times following treatment with a DNA nuclease solution or can be washed one or more times between DNA nuclease solution treatments. For example, a tissue can be treated with a first DNA nuclease solution and then washed three times before treatment with a second DNA nuclease solution.

Methods for determining the extent of DNA removal from a decellularized tissue are known in the art and include, e.g., polymerase chain reaction methods (e.g., to amplify a target region of DNA) or direct quantification of any DNA isolated from the decellularized tissue using spectrophotometry. Such methods are described in detail in, e.g., Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989), the disclosures of each of which are incorporated by reference in their entirety.

In some embodiments, the methods can also include obtaining (or harvesting) the tissue from a donor (e.g., a non-human mammal such as a pig or any of the non-human mammalian species described herein). Suitable methods for obtaining a tissue sample from a subject are set forth in the accompanying Examples. Additional methods for obtaining tissue samples are known in the art and described in, e.g., U.S. Publication No. 2006/0073592 and U.S. Pat. Nos. 5,336,616 and 6,933,326, the disclosures of each of which are incorporated by reference in their entirety. For example, donor skin samples can be harvested under aseptic conditions with a dermatome. (See, e.g., Olsson et al. (1997) *Acta Derm. Venereol.* 77(6):463-6; and Stone (1990) *Int. J. Dermatol.* 29(3):187-9).

In some embodiments, once obtained, the tissue can be placed into an initial stabilizing solution that arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution can contain an appropriate buffer (e.g., a biocompatible buffer such as any of those described herein), one or more antioxidants, one or more oncotic agents, one or more antibiotics, one or more protease inhibitors, and in some cases, a smooth muscle relaxant. For example, a harvested skin sample can be maintained at, e.g., 4° C. in RPMI 1640 tissue culture media containing penicillin and streptomycin solution for up to seven 7 days prior to further processing (see, e.g., U.S. Pat. No. 6,933,326).

In various embodiments, the tissue sample can be any of those described herein including, e.g., skin, bone, cartilage, meniscus, dermis, myocardium, periosteum, artery, vein, stomach, small intestine, large intestine, diaphragm, tendon, ligament, neural tissue, striated muscle, smooth muscle, bladder, urethra, ureter, and gingiva.

Galactosyl-α(1,3)galactose is a glycosyl modification of cell surface components and some serum proteins in all mammals, except humans and Old World apes. A major obstacle to successful xenotransplantation of porcine and other non-Old World ape vertebrate species organs into humans is the presence of Gal epitopes on the tissues of those organs. In some embodiments (e.g., where the input tissue sample is obtained from a nonhuman mammal such as a pig), the methods can also include contacting a tissue or a decellularized tissue with an agent (e.g., alpha-galactosidase or an N-glycanase such as peptide-N-glycosidase) that is capable of removing all, or substantially all, of the terminal galactose-α-1-3-galactose moieties from the tissue or decellularized tissue. As used herein, a tissue (e.g., a decellularized tissue or an ATM) lacking "substantially all terminal galactose-α-1-3-galactose moieties" is a tissue in which the concentration of terminal galactose-α-1-3-galactose moieties is less than 5% (e.g., less than: 4%, 3%, 2%, 1%, 0.9%, 0.8%, 0.7%, 0.6%, 0.5%, 0.4%, 0.3%, 0.2%, 0.1%; 0.01%; 0.001%; 0.0001%; 0.00001%; 0.000001%, or any values between) of that in the tissue prior to treatment with the agent. The decellularized tissue can be contacted with a solution comprising an effective amount of alpha-galactosidase, as described in, e.g., U.S. Pat. No. 6,331,319, the disclosure of which is incorporated by reference in its entirety. Methods for determining the amount of terminal galactose-α-1-3-galactose moieties, before and/or after treatment with an agent are known in the art and described in U.S. Pat. No. 6,331,319. For example, a tissue can be subjected to immunostaining techniques using an antibody specific for the galactose-α-1-3-galactose epitope (see, e.g., Galili (1993) $Immunol.$ $Today$ 14:480; the disclosure of which is incorporated herein by reference in its entirety). In addition, in certain embodiments, ATMs can be produced from animals genetically modified to have reduced levels of, or lacking -α-1-3-galactose moieties, as described, for example, in in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," $Tissue$ $Engineering$, Vol. 15, 1-13 (2009), which is incorporated by reference in its entirety.

In some embodiments, the methods can further include sterilizing the decellularized tissue. The sterilization methods described herein are generally non-damaging and are capable of: (i) providing a sterilized product (e.g., a sterilized ATM) at a sterility assurance level (SAL) of greater than about $10^{-6}$ (e.g., $10^{-7}$, $10^{-8}$, $10^{-9}$, or $10^{-10}$ or greater); (ii) achieving a greater than six (e.g., seven, eight, nine, 10, 11, 12, 13, 15, or more than 20) fold reduction in viral load in a product (e.g., a tissue or an ATM described herein); (iii) and substantially maintains the biological and structural functions of the product (e.g., a tissue or an ATM described herein) (described above). It is understood that the sterilization methods can be used to sterilize not only any decellularized tissues made by the methods described herein, but any tissue.

Such sterilization can include the steps of contacting a tissue (such as any decellularized tissue matrix made by a method described herein) with a solution comprising peracetic acid (PAA) and exposing the tissue to radiation. In some embodiments, the tissue can be contacted with the solution prior to exposure to irradiation. In some embodiments, the tissue can be exposed to irradiation prior to contact with the solution.

An aqueous solution containing PAA can contain less than about 5% (e.g., less than: 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, or values between) PAA. The solution can contain PAA at about 0.01% to about 2% (e.g., about 0.01% to about 1%, about 0.01% to about 0.5%, about 0.05% to about 1%, about 0.05% to about 2%, about 0.5% to about 0.75%, about 1.0% to about 2.0%, or about 0.05% to about 1.5%). The amount of PAA needed in the solution can vary based on, e.g., the type or amount of a microbial contaminant (e.g., an enveloped or non-enveloped virus) present, or suspected of being present, in a tissue sample (e.g., an acellular tissue matrix). In some embodiments, the solution comprising PAA can include additional components. For example, in some embodiments, the solution can include a peroxide. Exemplary solutions comprising PAA that may be used for sterilization of tissue matrices are described in U.S. Pat. No. 5,460,962, which is entitled, "Peracetic Acid Sterilization of Collagen or Collagenous Tissue," which is herein incorporated by reference in its entirety.

The solution containing PAA can contain a biocompatible buffer, such as any biocompatible buffer known in the art or described herein. The buffers can be used to adjust the pH of the PAA solution. For example, a buffer can be used to adjust the pH of a PAA solution to a neutral pH (e.g., a pH of about 6.0 to about 8.0 pH). Exemplary pH ranges for a PAA-containing solution include, e.g., a pH of about 7.0 to about 7.5; a pH of about 4.0 to about 7.5; or a pH of about 6.5 to about 7.5.

The PAA-containing solution can have a high ionic strength, e.g., a high salt concentration. For example, the PAA-containing solution can have a salt concentration from about 500 mM to about 3 M (Molar). An exemplary range of salt concentrations is about 0.5 M to about 2 M (or about 1 M to about 2 M). Suitable salts for use in the PAA-containing solutions include, but are not limited to, sodium chloride, potassium chloride, calcium chloride, and the like.

A decellularized tissue can be soaked in or washed with a PAA-containing solution (e.g., one with a neutral pH and a high ionic strength) for a time and under conditions sufficient to achieve sterilization. The amount of time required for treatment of the decellularized tissue with the PAA-containing solution can vary based on, e.g., the size of the tissue, the type of the tissue, and the type and/or amount of microbial contaminant in, or suspected of being present in, the tissue sample. A decellularized tissue can be contacted with the PAA-containing solution for about 5 minutes to about 30 hours (e.g., about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 15 hours, about 20 hours, about 25 hours, about 28 hours, or about 30 hours). In some embodiments, a tissue sample can be contacted with the PAA-containing solution for more than 30 hours.

In some embodiments, the PAA-containing solution can be washed from the decellularized tissue. For example, following treatment with a PAA-containing solution, a decellularized tissue can be washed once (or more than once) with, e.g., sterile water, saline, buffer, or a storage media to remove the PAA. Alternatively, the decellularized tissue can be placed directly into a sterile storage media or exposed to irradiation without rinsing.

In some embodiments, the radiation includes E-beam irradiation. In certain embodiments, the radiation includes gamma radiation. In some embodiments, the radiation is provided at a dose sufficient to sterilize the tissue after contacting the tissue with a solution comprising PAA. In some embodiments, the radiation is at a dose that is low enough to prevent loss of biological functions or otherwise damage the tissue. Further, as described in more detail below, in some embodiments, the tissue may be contacted with a protective solution before irradiation.

E-beam radiation is a form of ionizing energy that is generally characterized by its low penetration and high dosage rates. The beam, a concentrated, highly charged stream of electrons, is generated by the acceleration and conversion of electricity. The electrons are generated by equipment referred to as accelerators, which are capable of producing beams that are either pulsed or continuous. As the product/material being sterilized passes beneath or in front of the electron beam, energy from the electrons is absorbed. This absorption of energy alters various chemical and biological bonds within the product/material. The energy that is absorbed is referred to as the "absorbed dose." It is this absorption of energy—or "dose delivery"—that destroys the reproductive cells of microorganisms, e.g., by destroying their DNA chains.

A variety of E-beam irradiators can be used in the methods described herein and are commercially available, e.g., the RHODOTRON TT300 (from IBA, Louvain-la-Neuve, France) and the AEB emitter (from AEB, Willington, Mass.).

A decellularized tissue can be exposed to low-dose E-beam irradiation for a time and in an amount sufficient to achieve sterilization. The dosage of E-beam irradiation required to sterilize a decellularized tissue can vary based on, e.g., the size of the tissue, the type of the tissue, and the type and amount of microbial contaminant in, or suspected of being present in, the tissue sample.

A decellularized tissue can be subjected to a one-sided exposure of the electron beam until a sterilizing dose of radiation is absorbed. An "absorbed dose" of radiation is expressed in terms of kilograys (kGy), wherein one kilogray is equal to one thousand joules of energy deposited per kilogram of material. For example, the decellularized tissue can be irradiated until an absorbed dose of about 6 kGy or more (e.g., 7 kGy, 8 kGy, 9 kGy, 10, kGy, 12 kGy, 15 kGy, 20 kGy, 22 kGy, 25 kGy, 27 kGy, or up to 30 kGy, or fractional values of the foregoing) is achieved. In some embodiments, a decellularized tissue can be exposed to irradiation until an absorbed dosage of about 6 kGy to about 30 kGy, about 10 kGy to about 15 kGy, or about 10 kGy to about 20 kGy is achieved.

E-beam or gamma irradiation of a decellularized tissue can be carried out, e.g., by placing the tissue in a suitable container, e.g., a glass or plastic container, and exposing the tissue to the radiation. For example, the tissue may be placed on a conveyor, which then passes through the electron beam or is exposed to the gamma source. The time of exposure to the radiation can be proportional to the dimensions of the tissue.

Dosage can also be determined with the use of radiochromic dye films. Such films can be calibrated, usually in a gamma field, by reference to a national standard.

In some embodiments, the methods can also include the step of, following the sterilization step, testing for the presence or amount of one or more microorganisms (e.g., viruses, bacteria, or protozoa) in the decellularized tissue. Methods for determining whether a decellularized tissue contains a microorganism are known in the art and include, e.g., a variety of PCR techniques (e.g., quantitative amplification of specific microbial DNA or RNA markers); enzyme-linked immunosorbent assays (ELISA) using antibodies specific for microbial proteins; plaque-assays; hemagluttination assays; or colony formation tests. Effective sterilization can also be determined using conventional microbiological techniques, such as, for example, the inclusion of suitable biological indicators in a radiation batch or contacting the tissue with a culture medium, and incubating the medium to determine sterility of the tissue.

Methods for determining the structural integrity of a tissue, such as a decellularized tissue, are known in the art and described in the accompanying Examples. For example, the retention of structural integrity of an ATM can be determined by, e.g., histological observation of the matrix structure, collagen denaturation profiling, collagenase susceptibility, and removal of antigenic matrix components. In addition, the mechanical strength of a matrix can be determined, e.g., by measuring the maximum strength, the stiffness, the suture pull-out strength, or the pre-tension strain of the matrix. A collagen denaturation profile of a sterilized ATM can be determined, e.g., by measuring the temperature ($T_{onset}$) at which the protein structure of the matrix denatures, wherein the denaturation temperature decreases as a function of the level of damage to a matrix. Such a measurement can be performed by differential scanning calorimetry (DSC). Collagenase susceptibility of a sterilized ATM can be determined by contacting the ATM with collagenase and measuring the amount of time is required to digest the collagen of the matrix (as compared to the amount of time required for a non-sterilized ATM), wherein the amount of time decreases as a function of the level of damage to a matrix.

In some embodiments, the methods can also include the steps of incorporating one or more factors (e.g., growth factors, angiogenic factors, cytokines, hormones, or chemokines) into the decellularized matrices. Factors that can be incorporated into the matrices, include any of a wide range of cell growth factors, angiogenic factors, differentiation factors, cytokines, hormones, and chemokines known in the art. Any combination of two or more of the factors can be administered to a subject by any of the means recited below. Examples of relevant factors include fibroblast growth factors (FGF) (e.g., FGF1-10), epidermal growth factor, keratinocyte growth factor, vascular endothelial cell growth factors (VEGF) (e.g., VEGF A, B, C, D, and E), platelet-derived growth factor (PDGF), interferons (IFN) (e.g., IFN-α,β, or γ), transforming growth factors (TGF) (e.g., TGF α or β); tumor necrosis factor-α, an interleukin (IL) (e.g., IL-1-IL-18), Osterix, Hedgehogs (e.g., sonic or desert), SOX9, bone morphogenic proteins, parathyroid hormone, calcitonin prostaglandins, or ascorbic acid.

In some embodiments, the methods described herein can also include, prior to decellularizing the tissue, optionally slicing tissue in the horizontal plane to generate multiple sheets, removing the epithelial basement membrane.

An ATM can be preserved using any of a variety of treatment modalities, depending on, e.g., the desired use for the ATM (e.g., in particulate or sheet form), the amount of time the ATMs need to be stored, and type of tissue from which the ATMs are derived. For example, an ATM can be treated with a cryopreservation agent and cryopreserved and, optionally, freeze dried, under conditions necessary to maintain the described biological and structural properties of the matrix. If the tissue is to be frozen and freeze dried, following incubation in the cryopreservation solution, the ATM can be packaged inside a sterile vessel that is permeable to water vapor yet impermeable to bacteria, e.g., a water vapor permeable pouch or glass vial. One side of a preferred pouch can consist of medical grade porous TYVEK® membrane, a trademarked product of DuPont Company of Wilmington, Del. This membrane is porous to water vapor and impervious to bacteria and dust. The TYVEK® membrane is heat sealed to a impermeable polyethylene laminate sheet, leaving one side open, thus forming a two-sided pouch. The open pouch can be (optionally) sterilized prior to use (e.g., using gamma-irradiation or E-beam irradiation, as described above). The vessel containing the tissue is cooled to a low temperature at a specified rate that is compatible with the specific cryoprotectant formulation to minimize freezing damage. (See U.S. Pat. No. 5,336,616 for examples of appropriate cooling protocols). The tissue can then be dried at a low temperature under vacuum conditions, such that water vapor is removed sequentially from each ice crystal phase.

At the completion of the drying of the samples in the water vapor permeable vessel, the vacuum of the freeze drying apparatus is reversed with a dry inert gas such as nitrogen, helium or argon. While being maintained in the same gaseous environment, the semipermeable vessel is placed inside an impervious (i.e., impermeable to water vapor as well as microorganisms) vessel (e.g., a pouch), which is further sealed, e.g., by heat and/or pressure. Where the tissue sample was frozen and dried in a glass vial, the vial is sealed under vacuum with an appropriate inert stopper and the vacuum of the drying apparatus reversed with an inert gas prior to unloading. In either case, the final product is hermetically sealed in an inert gaseous atmosphere.

After freeze drying, the matrix can be pulverized or micronized to produce a particulate acellular tissue matrix under similar function-preserving conditions.

Particulate ATM can be made from any of the above described non-particulate ATM by any process that results in the preservation of the biological and structural functions described above and, in particular, damage to collagen fibers, including sheared fiber ends, should be minimized. Many known wetting and drying processes for making particulate ATM do not so preserve the structural integrity of collagen fibers.

One appropriate method for making particulate ATM is described in U.S. patent application Ser. No. 09/762,174. The process is briefly described below with respect to a freeze-dried dermal ATM but one of skill in the art could readily adapt the method for use with freeze-dried ATM derived from any of the other tissues listed herein.

The ATM can be cut into strips (using, for example, a Zimmer mesher fitted with a non-interrupting "continuous" cutting wheel). The resulting long strips are then cut into lengths of about 1 cm to about 2 cm. A homogenizer and sterilized homogenizer probe (e.g., a LABTEK MACRO homogenizer available from OMNI INTERNATIONAL™, Warrenton, Va.) is assembled and cooled to cryogenic temperatures (i.e., about <196° C. to about −160° C.) using sterile liquid nitrogen which is poured into the homogenizer tower. Once the homogenizer has reached a cryogenic temperature, cut pieces of ATM are added to the homogenizing tower containing the liquid nitrogen. The homogenizer is then activated so as to cryogenically fracture the pieces of ATM. The time and duration of the cryogenic fracturing step will depend upon the homogenizer utilized, the size of the homogenizing chamber, and the speed and time at which the homogenizer is operated, and are readily determinable by one skilled in the art. As an alternative, the cryofracturing process can be conducted in a cryomill cooled to a cryogenic temperature.

The cryofractured particulate acellular tissue matrix is, optionally, sorted by particle size by washing the product of the homogenization with sterile liquid nitrogen through a series of metal screens that have also been cooled to a cryogenic temperature. It is generally useful to eliminate large undesired particles with a screen with a relatively large pore size before proceeding to one (or more screens) with a smaller pore size. Once isolated, the particles can be freeze-dried to ensure that any residual moisture that may have been absorbed during the procedure is removed. The final product is a powder (usually white or off-white) generally having a particle size of about 1 micron to about 900 microns, about 30 microns to about 750 microns, or about 150 to about 300 microns. The material is readily rehydrated by suspension in normal saline or any other suitable rehydrating agent known in the art. It may also be suspended in any suitable carrier known in the art (see, for example, U.S. Pat. No. 5,284,655 incorporated herein by reference in its entirety). If suspended at a high concentration (e.g., at about 600 mg/ml), the particulate ATM can form a "putty," and if suspended at a somewhat lower concentration (e.g., about 330 mg/ml), it can form a "paste." Such putties and pastes can conveniently be packed into, for example, holes, gaps, or spaces of any shape in tissues and organs so as to substantially fill such holes, gaps, or spaces.

Alternatively, the ATM can be preserved by replacing most of the water in the tissue with a water-replacing agent such as glycerol such that the acellular tissue matrix contains, for example, up to approximately 85% by weight glycerol. One exemplary method for storing the ATMs using water-replacing agents is described in co-pending U.S. Patent Publication No. 2006/0073592, the disclosure of which is incorporated herein by reference in its entirety. The ATMs can be stored in this form for an extended period at less than 20° C. All steps are generally carried out under aseptic, preferably sterile, conditions.

In some embodiments, the ATM can be preserved in a ready-to-use preservation solution described herein (see, e.g., "Solutions"). Further, in some embodiments, the tissue is irradiated to sterilize the tissue while in the ready-to-use solution. As described in more detail below, in some embodiments, the ready-to-use solution can be selected to protect the tissue from radiation and to stabilize the tissue during storage. In some embodiments, the ready-to-use solution can have antimicrobial properties.

Following the preparations described above, an ATM is ready for implantation and, in some cases, only need be processed into a desired shape or size. The ATMs can be prepared in a variety of forms, including those selected from the group consisting of liquid, colloid, semi-solid, solid, particulate, gel, paste, and combinations of any of the foregoing as described above.

Articles of Manufacture

In some embodiments, the present disclosure provides articles of manufacture comprising a container and a composition contained within the container. In certain embodiments, the composition contains an active agent for treating an organ or tissue in need of repair or amelioration in a mammal, and the active agent in the composition comprises an acellular tissue matrix made by any of the methods described herein. In some embodiments, the container has a label indicating that the composition is for use in treating an organ or tissue in need of repair or amelioration in a mammal. The label can further indicate that the composition is to be administered to the mammal if the mammal is identified as having an organ or tissue in need of repair or amelioration. The types of organs and/or tissues that can be treated with a composition comprising an ATM are described above.

In some embodiments, the article can also include instructions for administering the active agent to the mammal. The instructions can feature any of the methods described above under the section titled "Methods for Using an ATM."

The ATM contained in the composition can be in a variety of forms such as, but not limited to, a liquid, colloid, semi-solid, solid, particulate, gel, paste, or combinations of any of the foregoing.

Methods for Using an ATM

In some embodiments, the form of ATM used in any particular instance will depend on the tissue or organ to which it is to be applied. Sheets of ATM (optionally cut to an appropriate size) can be, for example: (a) wrapped around a tissue or organ that is damaged or that contains a defect; (b) placed on the surface of a tissue or organ that is damaged or has a defect; or (c) rolled up and inserted into a cavity, gap, or space in the tissue or organ. Such cavities, gaps, or spaces can be, for example: (i) of traumatic origin, (ii) due to removal of diseased tissue (e.g., infarcted myocardial tissue), or (iii) due to removal of malignant or non-malignant tumors. The ATM can be used to augment or ameliorate underdeveloped tissues or organs or to augment or reconfigure deformed tissues or organs. One or more (e.g., one, two, three, four, five, six, seven, eight, nine, ten, 12, 14, 16, 18, 20, 25, 30, or more) such strips can be used at any particular site. The grafts can be held in place by, for example, sutures, staples, tacks, or tissue glues or sealants known in the art. Alternatively, if, for example, packed sufficiently tightly into a defect or cavity, they may need no securing device. Particulate ATM can be suspended in a sterile pharmaceutically acceptable carrier (e.g., normal saline) and injected via hypodermic needle into a site of interest. Alternatively, the dry powdered matrix or a suspension can be sprayed onto into or onto a site or interest. A suspension can be also be poured into or onto particular site. In addition, by mixing the particulate ATM with a relatively small amount of liquid carrier, a "putty" can be made. Such a putty, or even dry particulate ATM, can be layered, packed, or encased in any of the gaps, cavities, or spaces in organs or tissues mentioned above. Moreover, a non-particulate ATM can be used in combination with particulate ATM. For example, a cavity in bone could be packed with a putty (as described above) and covered with a sheet of ATM.

In some embodiments, an ATM can be applied to a tissue or organ in order to repair or regenerate that tissue or organ and/or a neighboring tissue or organ. Thus, for example, in some embodiments, a strip of ATM can be wrapped around a critical gap defect of a long bone to generate a periosoteum equivalent surrounding the gap defect and the periosteum equivalent can in turn stimulate the production of bone within the gap in the bone. Similarly, in some embodiments, by implanting an ATM in a dental extraction socket, injured gum tissue can be repaired and/or replaced, and the "new" gum tissue can assist in the repair and/or regeneration of any bone in the base of the socket that may have been lost as a result, for example, of tooth extraction. In regard to gum tissue (gingiva), receding gums can also be replaced by injection of a suspension, or by packing of a putty of particulate ATM into the appropriate gum tissue. Again, in addition to repairing the gingival tissue, this treatment can result in regeneration of bone lost as a result of periodontal disease and/or tooth extraction. Compositions used to treat any of the above gingival defects can contain one or more other components listed herein, e.g., demineralized bone powder, growth factors, or stem cells.

Both non-particulate and particulate ATM can be used in combination with other scaffold or physical support components. For example, one or more sheets of ATM can be layered with one or more sheets made from a biological material other than ATM, e.g., irradiated cartilage supplied by a tissue bank such as LifeNet, Virginia Beach, Va., or bone wedges and shapes supplied by, for example, the Osteotech Corporation, Edentown, N.J. Alternatively, such non-ATM sheets can be made from synthetic materials, e.g., polyglycolic acid or hydrogels such as that supplied by Biocure, Inc., Atlanta, Ga. Other suitable scaffold or physical support materials are disclosed in U.S. Pat. No. 5,885,829. It is understood that such additional scaffold or physical support components can be in any convenient size or shape, e.g., sheets, cubes, rectangles, discs, spheres, or particles (as described above for particulate ATM).

Active substances that can be mixed with particulate ATM or impregnated into non-particulate ATM include bone powder, demineralized bone powder, and any of those disclosed above (as described above under "Methods of Making and Using ATMs").

Factors that can be administered to the placement site of an ATM graft, or administered systemically include any of a wide range of cell growth factors, angiogenic factors, differentiation factors, cytokines, hormones, and chemokines known in the art and set forth above. Any combination of two or more of the factors can be administered to a subject by any of the means recited below. Factors that are proteins can also be delivered to a recipient subject by administering to the subject: (a) expression vectors (e.g., plasmids or viral vectors) containing nucleic acid sequences encoding any one or more of the above factors that are proteins; or (b) cells that have been transfected or transduced (stably or transiently) with such expression vectors. In the expression vectors' coding sequences are operably linked to one or more transcription regulatory elements (TRE). Cells used for transfection or transducion are preferably derived from, or histocompatible with, the recipient. However, it is possible that only short exposure to the factor is required and thus histo-incompatible cells can also be used. The cells can be incorporated into the ATM (particulate or non-particulate) prior to the matrices being placed in the subject. Alternatively, they can be injected into an ATM already in place in a subject, into a region close to an ATM already in place in a subject, or systemically.

In some embodiments, administration of the ATM and/or any of the other substances or factors mentioned above can be single, or multiple (e.g., two, three, four, five, six, seven, eight, nine, 10, 15, 20, 25, 30, 35, 40, 50, 60, 80, 90, 100, or as many as needed). Where multiple, the administrations can be at time intervals readily determinable by one skilled in art. Doses of the various substances and factors will vary according to the species, age, weight, size, and sex of the subject and are also readily determinable by a skilled artisan.

Conditions for which the matrices can be used are multiple. Thus, for example, they can be used for the repair of bones and/or cartilage with any of the above-described damage or defects. Both particulate and non-particulate ATM can be used in any of the forms and by any of the processes listed above. Bones to which such methods of treatment can be applied include, without limitation, long bones (e.g., tibia, femur, humerus, radius, ulna, or fibula), bones of the hand and foot (e.g., calcaneas bone or scaphoid bone), bones of the head and neck (e.g., temporal bone, parietal bone, frontal bone, maxilla, mandible), or vertebrae. As mentioned above, in some embodiments, critical gap defects of bone can be treated with ATM. In such critical gap defects, the gaps can be filled with, for example, a putty of particulate ATM or packed sheets of ATM and wrapped with sheets of ATM. Alternatively, the gaps can be wrapped with a sheet of ATM and filled with other materials (see below). In all these bone and/or cartilage treatments, additional materials can be used to further assist in the repair process.

For example, in certain embodiments, the gap can be filled cancellous bone and or calcium sulfate pellets and particulate ATM can be delivered to sites of bone damage or bone defects mixed with demineralized bone powder. In addition, ATM can be combined with bone marrow and/or bone chips from the recipient.

In certain embodiments, ATM can also be used to repair fascia, e.g., abdominal wall fascia or pelvic floor fascia. In such methods, strips of ATM are generally attached to the abdominal or pelvic floor by, for example, suturing either to the surrounding fascia or host tissue or to stable ligaments or tendons such as Cooper's ligament.

In some embodiments, infarcted myocardium is another candidate for remodeling repair by ATM. Contrary to prior dogma, it is now known that not all cardiac myocytes have lost proliferative, and thus regenerative, potential (see, e.g., Beltrami et al. (2001) *New. Engl. J. Med.* 344:1750-1757; Kajstura et al. (1998) *Proc. Natl. Acad. Sci.* USA 95:8801-8805). Moreover, stem cells, present for example in bone marrow and blood, and as pericytes associated with blood vessels, can differentiate to cardiac myocytes. Either the infarcted tissue itself can be removed and replaced with a sheet of ATM cut to an appropriate size or a suspension of particulate ATM can be injected into the infarcted tissue. Congenital heart hypoplasia, or other structural defects, can be repaired by, for example, making an incision in the tissue, expanding the gap created by the incision, and inserting a sheet of ATM cut to the desired size, or placing sheets of ATM on the epicardial and endocardial surfaces and placing particulate ATM between them. It is understood that, in certain conditions, creating a gap by incision may not be sufficient and it may be necessary to excise some tissue. Naturally, one of skill in the art will appreciate that the ATM can be used similarly to repair damage to, or defects in, other types of muscle, e.g., ureter or bladder or skeletal muscle such as biceps, pectoralis, or latissimus.

In certain embodiments, sheets of ATM can be used to repair or replace damaged or removed intestinal tissue, including the esophagus, stomach, and small and large intestines. In this case, the sheets of ATM can be used to repair perforations or holes in the intestine. Alternatively, a sheet of ATM can be formed, for example, into a cylinder that can be used to fill a gap in the intestine (e.g., a gap created by surgery to remove a tumor or a diseased segment of intestine). Such methods can be used to treat, for example, diaphragmatic hernias. It will be understood that an ATM in sheet form can also be used to repair the diaphragm itself in this condition as well as in other conditions of the diaphragm requiring repair or replacement, or addition of tissue.

Solutions

In some embodiments, Ready-To-Use (RTU) solutions for use in storage and/or preservation of, a tissue or an ATM (e.g., an ATM made by the methods described herein) are provided. As used herein, the term "RTU solutions" and the term "RTU" are each used interchangeably with the term "preservation solution" or "protective solution." In certain embodiments, such solutions allow for an ATM to: (i) be delivered to a medical practitioner (e.g., a doctor) in a fully hydrated state; (ii) be ready for use upon opening of a sterile package containing the ATM; and (iii) be stored for up to 2 years (e.g., 3 months, 4 months, 5 months, 6 months, 1 year, 1.5 years, or up to 2 years) when maintained at about 2° C. to about 8° C. or for up to 1 year (e.g., 2 months, 3 months, 4 months, 5 months, 6 months, 7 months, 8 months, 9 months, 10 months, 11 months, or up to 1 year) at room temperature. In some embodiments, the solutions can also inhibit one or more of the following phenomena: (i) microbial growth; (ii) hydrolysis of an ATM; (iii) oxidation and/or discoloration of an ATM; (iv) Maillard reactions within the ATM; (v) residual, detrimental enzymatic activities present in the ATM (e.g., matrix metalloproteinases). Additional properties of the solutions are set forth in the accompanying Examples.

In some embodiments, the solutions can contain the following components: a biocompatible buffer; a salt; a surfactant; one or more reducing agents, transition metal chelators, and free-radical scavengers; a tissue stabilizer (and/or a microbial stasis agent); and one or more biocompatible co-solutes. In some embodiments, the solution can have a pH of between about 5.2 to about 6.9 (e.g., a pH of about 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or any ranges or fractional values between these). In some embodiments, the solution can also have a water activity of between about 0.930 to about 0.995.

As used herein, the "water activity" ($a_w$) of a solution is a measurement of the energy status of the water in a solution, which is defined as the equilibrium vapor pressure of water in the solution divided by that of pure water at the same temperature. Thus, pure distilled water has a water activity of exactly one.

In some embodiments, the biocompatible buffer can be, e.g., a citrate buffer, a phosphate buffer, an acetate buffer; HEPES buffer, MOPS buffer, Tris buffer, a combination of a citrate buffer and a phosphate buffer (citrate/phosphate buffer), or any other biocompatible buffers known in the art or described herein. The buffer can be at a concentration of up to 150 (e.g., 1, 5, 10, 15, 20, 25, 30, 35, 50, 55, 60, 65, 70, 75, 80, 85, 90, 95, 100, 110, 115, 120, 125, 130, 135, 140, 145, 150, or any ranges or fractional values between these) mM in the solution. In embodiments where a phosphate containing buffer is selected, the solution can also contain any of a variety of polymeric hydroxyl compounds (e.g., stabilizing polyols), which can prevent salt crystallization upon freezing of the buffers.

In some embodiments, the salt can be, e.g., a sodium salt such as sodium chloride (e.g., fluoride, sulfate, or phosphate). In some embodiments, the salt is not a potassium or a calcium salt. The salt can be at a concentration of up to about 150 (e.g., 1, 5, 10, 15, 20, 25, 30, 35, 50, 55, 60, 65, 70, 75, 80, 85, 90, 95, 100, 105, 110, 115, 120, 125, 130, 135, 140, 145, 150, or any ranges or fractional values between these) mM in the solution.

In some embodiments, the surfactant can be, e.g., an ionic (e.g., anionic, cationic, or Zwitterionic) or non-ionic surfactant. For example, ionic surfactants include, e.g., SDS, ammonium laurel sulfate, alkyl benzene sulfonate, soaps, fatty acids, cetyl trimethylammonium bromide (CTAB), cetylpyridinium chloride (CPC), polyethoxylated tallow amine (POEA), benzalkonium chloride (BAC), benzethonium chloride (BZT), dodecyl betaine, dodecyl dimethylamine oxide, docamidopropyl betaine, and coco ampho glycinate. Non-ionic surfactants include, but are not limited to, TWEEN-20®, TWEEN-80®, alkyl poly(ethylene oxide), copolymers of poly(ethylene oxide) and poly(propylene oxide), octyl glucoside, decyl maltoside, cetyl alcohol, oleyl alcohol, cocamide MEA, cocamide DEA, and cocamide TEA. The surfactant can be in an amount of about 0.2% (w/v) or less (e.g., 0.19%, 0.18%, 0.17%, 0.16%, 0.15%, 0.14%. 0.13%, 0.12%, 0.11%, 0.10%, 0.09%, 0.08%, 0.07%, 0.06%, 0.05%, 0.04%, 0.03%, 0.02%, 0.01%, 0.009%, 0.005%, or 0.001% or lower, or any ranges or fractional values between these) of the solution.

In some embodiments, the metal chelating agents that can be used in the solutions described herein include, e.g., EDTA, EGTA, DMPS, DMSA, and DTPA. The metal chelating agent can be present at a concentration of between about 1 mM to about 50 mM (e.g., about 2, 3, 4, 5, 6, 7, 8, 9 10, 11, 12, 13, 14, 15, 20, 22, 25, 27, 30, 32, 35, 37, 40, 42, 45, 47, or 50 mM, or any ranges or fractional values between these) in the solution.

In some embodiments, the suitable tissue stabilizers for use in the solutions described herein include, e.g., glycerol, dimethylsulfoxide (DMSO), sodium glycerophosphate and any of a wide range of polyhydroxyl compounds (also sometimes called polyhydroxy or polyol compounds) such as poly-glycerol, ethylene glycol, propylene glycol, polyethylene glycol (PEG), polyvinyl alcohols, or combinations of any of the foregoing. The tissue stabilizer can in an amount of about 10% or less (e.g., 9%, 8%, 7%, 6%, 5%, 4%, 3%, 2%, or 1% or less, or any ranges or fractional values between these) of the solution or it can be at a concentration of about 500 mM or less (e.g., 450 mM, 400 mM, 350 mM, 300 mM, 250 mM, 200 mM, 150 mM, 100 mM, 50 mM, 25 mM, or 10 mM or less, or any ranges or fractional values between these) in the solution.

In some embodiments, the biocompatible co-solutes can include, but are not limited to, sugars or sugar alcohols such as trehalose, mannitol, sorbitol, xylitol, erythritol, arabitol, isomalt, maltitol, lactitol, or combinations of any of the foregoing. A biocompatible co-solute can be present in an amount of up to about 20% (w/v) or less (e.g., 19%, 18%, 17%, 16%, 15%, 14%, 13,%, 12%, or 11% 10%, 9%, 8%, 7%, 6%, 5%, 4%, 3,%, 2%, or 1% or less, or any ranges or fractional values between these) of the solution (or up to a concentration of 1 (e.g., 0.05, 0.1, 0.2, 0.3, 0.4, 0.5, 0.6, 0.7, 0.8, 0.9, or up to 1, or any ranges or fractional values between these) M in the solution).

In some embodiments, the solution can have a pH of about 5.4 to about 6.0 (e.g., a pH of about 5.5, 5.6, 5.7, 5.8, 5.9, or 6.0). In some embodiments, the solution can have a water activity of about 0.95 to about 0.97 (e.g., about 0.951, 0.952, 0.953, 0.954, 0.956, 0.957, 0.958, 0.959, 0.960, 0.961, 0.962, 0.963, 0.964, 0.966, 0.967, 0.968, 0.969, or 0.970).

Exemplary solutions are as follows:

(i) a solution comprising: citrate at a concentration of about 20 mM; sodium chloride at a concentration of about 100 mM in the solution; TWEEN-20® in an amount of about 0.2% (w/v) of the solution; EDTA at a concentration of about 2 mM; and glycerol in an amount of about 10% (w/v) of the solution, and having a pH of about 5.4;

(ii) a solution comprising: citrate at a concentration of about 20 mM; sodium chloride at a concentration of about 100 mM in the solution; TWEEN-20® in an amount of about 0.2% (w/v) of the solution; EDTA at a concentration of about 2 mM; glycerol in an amount of about 10% (w/v) of the solution; and trehalose at a concentration of about 500 mM, and having a pH of about 5.4;

(iii) a solution comprising: citrate at a concentration of about 20 mM; sodium chloride at a concentration of about 100 mM in the solution; TWEEN-20® in an amount of about 0.2% (w/v) of the solution; EDTA at a concentration of about 2 mM; glycerol in an amount of about 10% (w/v) of the solution; trehalose at a concentration of about 200 mM; and mannitol at a concentration of about 200 mM; and having a pH of about 6.4;

(iv) a solution comprising: 4.8 mM citric acid (monohydrate), 15.2 mM sodium citrate tribasic dehydrate, 7.3 mM EDTA 2Na, 83.5 mM NaCl, 200 mM mannitol (anhydrous), 10% (w/v) glycerol, 0.013% (w/v) TWEEN-20®, 0.34 mM $KH_2PO_4$, and 1.85 mM$Na_2HPO_4$;

(v) a solution comprising: 4.8 mM citric acid (monohydrate), 15.2 mM sodium citrate tribasic dehydrate, 7.3 mM EDTA 2Na, 83.5 mM NaCl, 200 mM mannitol (anhydrous), 10% (w/v) glycerol, 100 mM trehalose (dihydrate), 0.013% (w/v) TWEEN-20®, 0.34 mM $KH_2PO_4$, and 1.85 mM$Na_2HPO_4$; and (vi) a solution comprising: 4.0 mM citric acid, 26 mM sodium citrate, 5 mM sodium EDTA, 80 mM NaCl, 15% (w/v) glycerol, and 0.02% (w/v) TWEEN-20®; and one of the following: (a) 300 mM trehalose and 300 mM mannitol; (b) 100 mM trehalose and 100 mM mannitol; (c) 100 mM trehalose and 300 mM mannitol; or (d) 300 mM trehalose and 100 mM mannitol.

Methods for determining the pH and water activity of a solution, as well as any of the above-described properties of the solutions, are known in the art and are set forth in the accompanying Examples. For example, the antibacterial property of a solution described herein can be measured by inoculating a sample of the buffer with any of a variety of microorganisms (such as, e.g., *E. coli* ATCC 8739, *Pseudomonas aeruginosa* ATCC 9027, *Staphylococcus aureus* ATCC 6538, *Bacillus subtilis* ATCC 6633, *Candida albicans* ATCC 10231, and *Aspergillus niger* ATCC 16404) and culturing the inoculated samples for varying amounts of time at storage temperatures (e.g., at 2° C. to 8° C.). The amount of a microorganism remaining in the sample at a given time point can be assessed as the number of colony forming units per milliliter (cfu/ml) present in each solution preparation.

Suitable methods for preserving ATMs using the solutions are described above and set forth in the accompanying Examples. For example, a ATM can be incubated in a solution at a ratio of 2 ml solution per gram (g) of the ATM for about 48 (e.g., about one, two, three, four, five, six, seven, eight, nine, 10, 11, 12, 13, 15, 17, 20, 21, 22, 23, 24, 25, 27, 30, 31, 32, 35, 37, 40, 41, 42, 43, 44, 45, 46, 47, or 48) hours.

Kits

Also provided in the present disclosure are kits containing any of the solutions described above and, optionally, instructions for preserving a tissue. Alternatively, the kits can contain one or more individual dried components (or, e.g., a single package containing all of the dried components) for making one of the solutions described above. In some embodiments, the kits can also include a sterile, pharmaceutically acceptable diluent for hydrating the dried components of the buffer. In some embodiments, the kits can also include one or more vessels for storing an ATM contacted with the solutions, or for storing the solutions prior to use.

The following examples serve to illustrate, not limit, the invention.

EXAMPLES

Example 1. Design of an Aqueous Preservation Solution for a Tissue Matrix

In some embodiments, in order to preserve a non crosslinked ATM's structural integrity and functionality of crucial biochemical components (e.g., collagens, elastin, and proteoglycans), an aqueous preservation formulation can be able to address any or all of the following issues:

1) Microbial growth;
2) Hydrolysis—Hydrolytic breakdown is a spontaneous process in aqueous solution;
3) Lipid oxidation—the lipid content of the ATMs is still very high after processing and varies greatly from donor to donor. Lipid peroxides, by-products of lipid oxidation, are very reactive and can significantly reduce the product shelf life;

4) Maillard reactions—When coupled with lipid oxidation, the ATM's functionality may be compromised; and 5) Enzyme activity—matrix metalloproteinases (MMPs), e.g., may still be present in trace amounts after processing the ATM.

In view of the foregoing, ready-to-use ATM preservation solutions were developed using three rational formulation principles:

1) selection of a proper buffer system to increase the stability of ATM proteins;

2) application of hurdle technologies (e.g., microbial stasis agents, free radical scavengers); and 3) incorporation of specific and non-specific compatible co-solvents (e.g., stabilizers).

Selection of Biocompatible Buffers

In some embodiments, a suitable buffer for ATM preservation is non-toxic and has maximum buffer capacity at a pH where ATM proteins exhibit optimal stability. In some embodiments, the buffer agent should be stable and should not absorb either in the visible or in the ultraviolet (UV) region. Photon absorption by buffer agents in the visible and UV region causes photosensitizing reactions. A number of biocompatible buffers will meet these requirements including, e.g., acetate buffers (pH from 3.6 to 5.8), citrate/phosphate buffers (pH from 2.6 to 7.0), phosphate buffers (pH from 5.8 to 8.0), and citrate buffers (pH from 3.0 to 6.0).

In some embodiments, a suitable buffer should be one that exhibits little or no change in pH with temperature, especially when the tissue in solution is frozen (e.g., when cold gamma irradiation or E-beam is used for terminal sterilization). In addition to the pH effect, the extent to which proteins may be stabilized or destabilized by a buffer also depends on other factors. For example, the conformation of collagen molecules is known to be protonation-dependent. The unfolding of such proteins is linked to the protonation of a solvent-exposed amino acid residue, and as a result, the stability of proteins is inversely correlated with the buffer's ionization enthalpy. The citrate buffer has one of the lowest ionization enthalpies (−11 kJ/mol) among many biological buffers including phosphate (−1 kJ/mol), HEPES (+3 kJ/mol) and MOPS (+23 kJ/mol). The buffer/metal complexation alters protein conformation if the metal ion acts as a catalyst in redox reactions or it changes the free energy of protein denaturation. The citrate buffer improves the effectiveness of antioxidants. Citric acid and its salts are also powerful calcium chelators, and therefore, are expected to inactivate some MMPs if such MMPs are still present in the ATM after tissue processing.

To formulate a proper ATM preservation solution, a number of different buffers were screened over a range of pH values. In earlier experiments, four buffers (acetate, phosphate, citrate, and citrate/phosphate) were used in ATM storage studies. The pH varied from 4.0 to 7.4. An accelerated storage experiment at 37° C. showed that lipid oxidation (browning) in ATM increased with pH.

Slightly acidic conditions (pH ~5.0 to 6.0) were believed to provide greater stability of collagen-based ATM. Type I collagen has three alpha chains: 2 alpha 1 chains and 1 alpha 2 chain. The isoelectric point (pI) of the type I alpha 1 chain is ~5.66 and the pI of the type I alpha 2 chain is ~9.08. The difference between pI and the storage pH influences the net charge on proteins. The greater the difference is, the more net charges collagen molecules have. The ability of ionic compounds to stabilize collagen by binding to specific amino acid residues increases with the difference between pI and pH. But, if the pH is too low, collagen molecules can swell and become less stable at ambient temperatures for long-term storage. The ability of certain ionic compounds to destabilize collagen also increases with the difference between pI and pH. The considerations described above led to the selection of two testing buffers:

(a) 20 mM citrate buffer, pH ~5.4; and (b) 4 mM citrate and 26 mM phosphate buffer, pH ~6.4.

MicroDSC is commonly used to screen different pHs and buffers for liquid protein formulations (including acid-soluble small collagen molecules). The pH condition that results in the highest $T_m$ of proteins typically maintains the protein in its native state for the longest time at lower temperatures as well. Using DSC, the effect of pH on ATM stability was investigated. These experiments demonstrated that the collagen of decellularized human ATM is most stable at pH from 7.0 to 8.0, and the stability decreases significantly at pH<5.0.

A slightly acidic pH range (5.0 to 6.5) represents a compromise for maintaining collagen stability and inhibiting lipid oxidation and ATM browning.

Selection of ATM Stabilizers

Initially, the selection of stabilizers for the ready-to-use ATM formulation was based on several considerations. Two considerations were (a) to prevent or retard undesirable events that could occur during ATM storage (e.g., microbial growth, lipid oxidation, etc) and (b) to preserve both various ATM proteins and their supramolecular assembly (i.e., matrix physical structure). The strategy that was used to preserve ATM proteins and their supramolecular assembly was a "molecular coating" mechanism, i.e., the incorporation of specific and non-specific compatible co-solvents (stabilizers) into the formulation so that the preferential exclusion of such co-solvents from the protein hydration shell could lead to the preferential hydration (and thus stabilization) of proteins that were surrounded with a co-solvent layer of increased density relative to the bulk solution concentration.

Several molecular simulation studies have reported this unique property of trehalose in aqueous protein solutions. For example, Lins R. D. et al. "Trehalose—Protein Interaction in Aqueous Solution," *Proteins: Structure Function and Bioinformatics* 55: 177-186 (2004), which is herein incorporated by reference in its entirety, describe the radial distribution functions [g(r)] for water oxygen moieties or trehalose oxygen moieties around the geometric center of the protein (in an ATM) in the absence or in the presence of 0.5 M trehalose. The molecular simulation data shows that trehalose molecules cluster and move toward the protein (neither expelling water from the protein surface nor forming hydrogen bonds with the protein). The coating by trehalose at moderate concentration does not significantly reduce conformational fluctuations of the protein.

In addition, in some embodiments, it is desirable to select ready-to-use formulations that are radiolysis-resistant and provide at least some protection for an ATM under radiation conditions (as gamma radiation was found to produce several undesirable effects that were similar to the aging processes during ATM storage). Thus, low dose cold gamma irradiation was used to screen the combinations of stabilizers for the ready-to-use formulation. The combination of glycerol and trehalose was found to be superior to other combinations for ATM protection against gamma irradiation. In addition, it was thought that this screening strategy might lead to a formulation that would also offer some protection against radiation damage.

Other considerations for the solutions included, e.g., the water activity and ionic strength. The water activity of the solution was reduced to about 0.95 to 0.97. Ionic strength was balanced by adding NaCl. NaCl affects protein conformation because the cation of the salt (i.e., Na$^+$) is a buffer component.

The content of lipids in processed ATM varies greatly from one sample to another, ranging from 0.2% to >30% (w/w) of tissue mass (based on the data of >60 production lots). Lipid oxidation and its by-products could cause an array of free radical-mediated protein degradation reactions. Lipids can undergo auto-oxidation, and therefore, the oxygen exclusion packaging method alone is not adequate to prevent lipid oxidation during ATM storage. Thus, mannitol and trehalose were added in the formulations to inhibit lipid degradation.

Table 1 lists six components and their perceived roles in the ready-to-use preservation solutions. The number of chemicals used in formulations was kept to a minimum through the selection of agents that were able to play multiple roles to address those major issues described above. For example, EDTA and glycerol served as microbial stasis agents and, at the same time, were able to inhibit the activities of matrix metaloproteinaces (MMPs) (if they were present). EDTA was also an effective free radical scavenger, and at a concentration of 1 to 5 mM, it prevented metal-induced oxidation of —SH groups and helped to maintain proteins in a reduced state.

TABLE 1

Perceived roles of individual components in the ready-to-use formulations.

| Perceived roles | Citrate | EDTA | TWEEN-20 ® | Glycerol | Mannitol | Trehalose |
|---|---|---|---|---|---|---|
| Inhibition of microbial activity | | ** | * | ** | * | * |
| Inhibition of enzymatic activity | | * | | * | | |
| Inhibition of hydrolytic activity | | | | | * | * |
| Inhibition of lipid oxidation | | * | | | ** | ** |
| Inhibition of Maillard reactions | | | | | | * |
| Stabilization of proteins | * | | ** | ** | * | * |

* or ** indicates the relative effectiveness of each component in the solution.

Example 2. Antimicrobial Activities of Solutions

Antimicrobial activities of preservation solutions were tested using the following two solution formulations.

1: a solution containing 4.8 mM citric acid (monohydrate), 15.2 mM Na citrate tribasic dehydrate, 7.3 mM EDTA 2Na, 83.5 mM NaCl, 200 mM mannitol (anhydrous), 10% (w/v) glycerol, 0.013% (w/v) TWEEN-20®, 0.34 mM KH$_2$PO$_4$, and 1.85 mM Na$_2$HPO$_4$.

2: a solution containing 4.8 mM citric acid (monohydrate), 15.2 mM Na citrate tribasic dehydrate, 7.3 mM EDTA 2Na, 83.5 mM NaCl, 200 mM mannitol (anhydrous), 10% (w/v) glycerol, 100 mM trehalose (dihydrate), 0.013% (w/v) TWEEN-20®, 0.34 mM KH$_2$PO$_4$, and 1.85 mM Na$_2$HPO$_4$.

Prepared solutions were sterile-filtrated and dispensed into sterile plastic bottles (50 ml solution added to each bottle). Solution bottles were inoculated with six different microorganisms (*Escherichia coli* ATCC 8739, *Pseudomonas aeruginosa* ATCC 9027, *Staphylococcus aureus* ATCC 6538, *Bacillus subtilis* ATCC 6633, *Candida albicans* ATCC 10231, and *Aspergillus niger* ATCC 16404). The appropriate microorgamsm was added to each bottle in each set to produce a final concentration of between $4.0 \times 10^5$ and $8.7 \times 10^6$ colony forming units per milliliter (cfu/ml). The initial concentration of viable organisms in each test solution (at day 0) was determined by heterotrophic plate counts (HPC) before storage at 2 to 8° C. The colony forming units per milliliter (cfu/ml) present in each solution preparation at day 60 and 180 of storage were determined again by HPC.

Figure 1B:
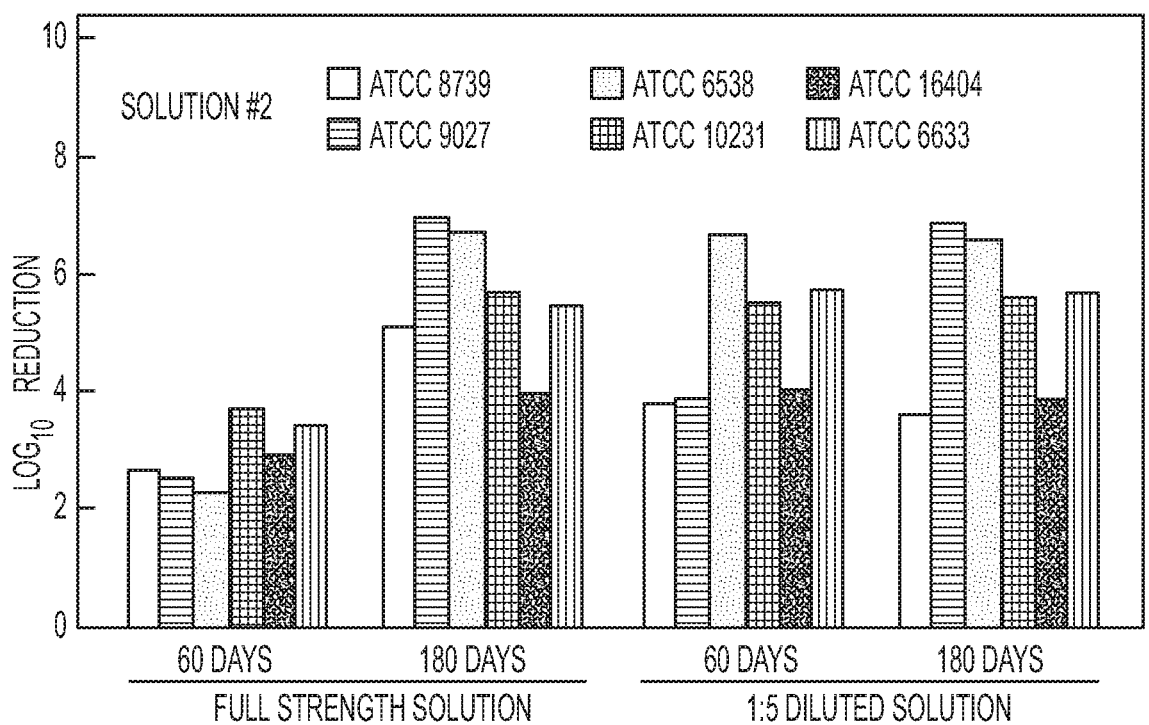

The change in $\log_{10}$ values of cfu/ml for each microorganism at the applicable test intervals was expressed in terms of log reductions. FIGS. 1A and 1B are a pair of bar graphs depicting the antimicrobial activity of two exemplary preservation solution formulations—Solution formulation #1 (top graph) and Solution formulation #2 (bottom graph)—(including solutions diluted 1:5 in water) during storage at 2 to 8° C. The Y-axis represents the reduction of microbes (in $\log_{10}$). The X-axis represents the amount of time the exemplary solutions containing the different microorganisms were incubated.

Both test solutions showed strong antimicrobial activities during storage at 2 to 8° C.

Example 3. Sterilization of ATM in Preservation Solutions Using Low-Dose Gamma Irradiation The presence of antimicrobial activities of the preservation solution suggests that the sterility of tissue products that are preserved in a preservation solution can be achieved by low dose gamma irradiation. The following experiment was performed to test the ability of low gamma irradiation (0, 5 and 10 kGy) to kill microbes in the preservation solutions.

The test solution used for the experiment contained: 2.7 mM citric acid, 17.3 mM sodium citrate, 7.3 mM EDTA, 116.7 mM sodium chloride, 200 mM mannitol, 10% (w/v) glycerol, 0.02% (w/v) TWEEN-20®, 200 mM trehalose, 0.34 mM KB$_2$PO$_4$, and 1.85 mM KB$_2$PO$_4$.

Solutions were sterile-filtrated and dispensed into sterile plastic bottles (40 ml each). Four sets of solution bottles were prepared for inoculation with each of six different microorganisms. Microorganisms tested were: *Escherichia coli* ATCC 8739, *Pseudomonas aeruginosa* ATCC 9027, *Staphylococcus aureus* ATCC 6538, *Bacillus subtilis* ATCC 6633, *Candida albicans* ATCC 10231, *Aspergillus niger* ATCC 16404. The appropriate microorgamsm was added to each bottle in each set to produce a final concentration of between $7.5 \times 10^7$ and $1.25 \times 10^8$ colony forming units per milliliter (cfu/ml).

One set of inoculated samples was used to determine the number of surviving organisms after inoculation and brief storage under refrigeration (control #1). Three sets were sent out to a commercial gamma irradiation facility and subjected to 0 (control #2), 5, and 10 kGy gamma irradiation, respectively.

Following irradiation, heterotrophic plate counts (HPC) of all controls and irradiated solutions were performed in duplicate to determine the number of surviving organisms present.

Following plate count enumeration, confirmation of the identity of the indicated organism was performed using standard microbiological methods.

The numbers of surviving organisms in the control #1 set were determined to be $4.7 \times 10^7$ for *Escherichia coli* ATCC 8739, $1.0 \times 10^6$ for *Pseudomonas aeruginosa* ATCC 9027, $3.1 \times 10^7$ for *Staphylococcus aureus* ATCC 6538, $1.0 \times 10^6$ for *Bacillus subtilis* ATCC 6633, $4.2 \times 10^7$ for *Candida albicans* ATCC 10231 and $1.0 \times 10^6$ for *Aspergillus niger* ATCC 16404. These numbers were lower than the number of microorganisms added, indicating that a large number of microorganisms did not survive the exposure to the preservation solution and/or that they could not be recovered.

The control #2 set was shipped to a commercial gamma irradiation facility and was sent back without gamma irradiation. During the brief shipment period at ambient temperature (2 days), there was further reduction in the number of surviving microorganisms for *Escherichia coli* ATCC 8739, *Staphylococcus aureus* ATCC 6538, *Bacillus subtilis* ATCC 6633, *Candida albicans* ATCC 10231 and *Aspergillus niger* ATCC 16404 (five out of six organisms tested).

Figure 2:
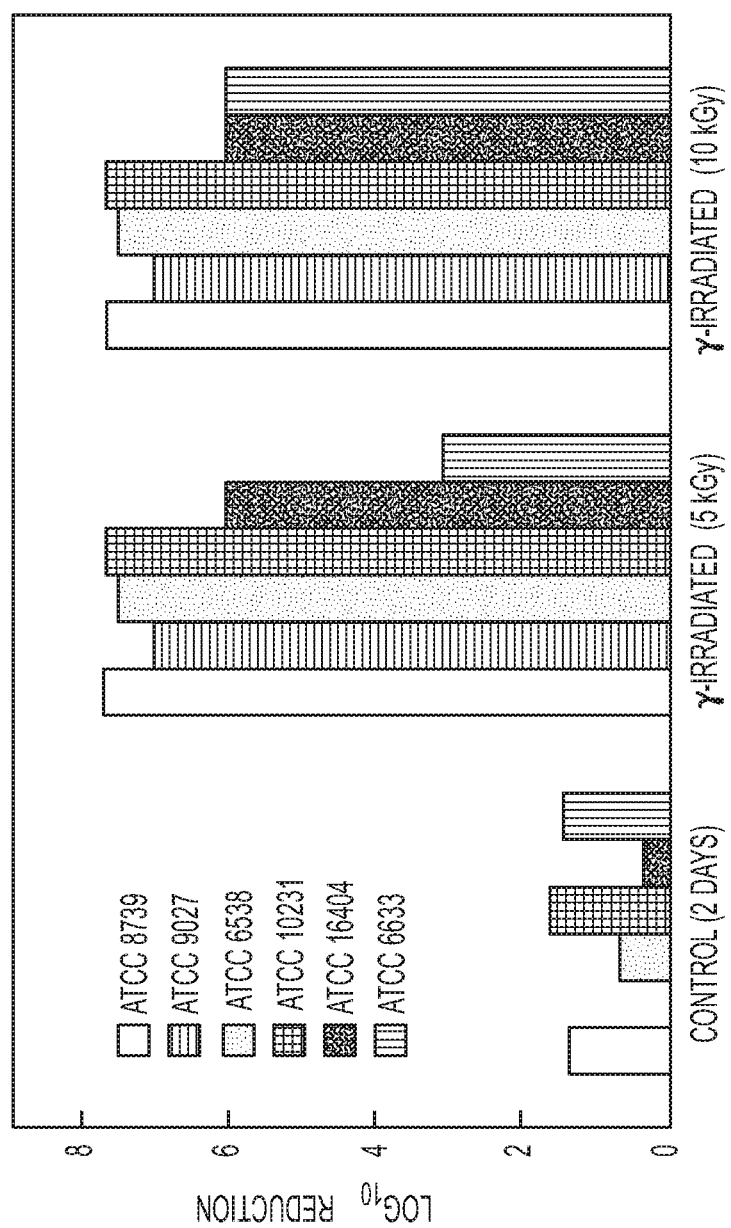
FIG. 2 is a bar graph depicting the effect of low dose gamma irradiation on bacterial growth in an exemplary preservation solution, according to certain embodiments.

FIG. 2 is a bar graph depicting the effect of low-dose gamma irradiation on bacterial growth in an exemplary preservation solution. The Y-axis represents the reduction of microbes (in $\log_{10}$). The X-axis represents the dosage of gamma-irradiation delivered to the exemplary solution containing the different microorganisms. A dose as low as 5 kGy achieved at least 6 log reduction of all bacteria types except for *Bacillus subtilis* ATCC 6633; and 10 kGy achieved at least 6 log reduction for all tested microorganisms.

Example 4. Protection by Stabilizers Against Tissue Damage from Gamma Irradiation at −80° C.

The following experiment was performed to demonstrate the protective effect of some stabilizers and their combinations against tissue damage upon cold gamma irradiation.

Human skin tissue samples (5 donor lots) were processed to remove the epidermis and cells from the skin. The epidermis was removed by soaking in 0.5% Triton X100 and 5.85% sodium chloride for about 20 hours, and de-cellularization was performed by soaking 2% sodium deoxycholate for 18 hours. Decellularized tissue matrix was then preserved in a preservation solution containing a base citrate/phosphate buffer, as well as sucrose, trehalose and glycerol as protectants against cold gamma irradiation at −80° C. The base buffer contained 12.8 mM $Na_2HPO_4$, 3.6 mM citric acid, 100 mM NaCl and 0.02% TWEEN-20®. The following six solutions were tested: (i) base buffer only; (ii) base buffer+1.0 M glycerol; (iii) base buffer+0.5 M sucrose; (iv) base buffer+1.0 M glycerol+0.5 M sucrose; (v) base buffer+0.5 M trehalose; and (vi) base buffer+1.0 M glycerol+0.5 M trehalose.

Tissue samples (1 square cm) were placed into 2.0 mL cryotubes containing different protective solutions and were frozen at −80° C. One set of tissue samples was placed into a box filled with crushed dry ice (−78.5° C.) and gamma-irradiated at a dose of 13 kGy. Both control samples and irradiated samples were stored at −80° C. before they were thawed and washed for histological evaluation of tissue samples. Sections of tissue matrix samples were mounted on glass microscope slides and stained with hematoxylin and eosin (H&E) stain using standard procedures. Slides were examined for gamma irradiation induced tissue matrix damage. Samples were scored using the following criteria:

Presence of Holes in the Sample:

Holes in the ATM may represent a variety of structures including blood vessels, empty adipocytes, vacant hair follicles, and expansion of gas bubbles within the sample during the freeze-drying process. Histologically, it is difficult to distinguish between these, and hence the presence of holes is graded according to the total percentage area of the sample occupied by these structures. Scoring is determined based on the following thresholds:

| Score | Assessment |
| --- | --- |
| 1-2 | Holes in 0%-10% of the sample. |
| 3-4 | Holes in 11%-25% of the sample. |
| 5-6 | Holes in 26%-40% of the sample. |
| 7-9 | Holes in 41%-60% of the sample. |
| 10 | Holes in >60% of the sample. |

Collagen Damage:

"Collagen damage" refers to the presence of broken collagen fibers, condensed collagen fibers, or distorted fibers. Collagen damage is reported as incidence of observation in visual fields for all samples. Scoring is determined based on the following thresholds:

| Score | Assessment |
| --- | --- |
| 1-2 | Damage in 0%-10% of the fields examined. |
| 3-4 | Damage in 11%-25% of the fields examined. |
| 5-6 | Damage in 26%-50% of the fields examined. |
| 7-8 | Damage in 51%-75% of the fields examined. |
| 9-10 | Damage in 76%-100% of the fields examined. |

Papillary and Reticular Layer:

Normal human dermis contains a papillary layer consisting of a superficial basement membrane zone and a layer of vascular and amorphous structure lacking clearly defined thick bundles of collagen. The collagen and elastin appearance of the papillary layer is one of fine reticulation. The reticular layer merges with the papillary layer and is composed of clearly defined collagen bundles. If collapse or melting occurs during processing of the tissue to produce the ATM, a condensation of the papillary layer is often observed. Scoring is determined based on the following thresholds:

| Score | Assessment |
| --- | --- |
| 0 | Clearly defined vascular plexus, clear transition. |
| 0-2 | Loss of structural features in superficial papillary layer, including vascular plexus. |
| 0-2 | Loss of structural features in inner papillary layer. |
| 0-2 | Loss of transition zone between papillary and reticular layer. |
| 0-10 | Absence or replacement of papillary layer with amorphous condensed layer. |

Figure 3A:
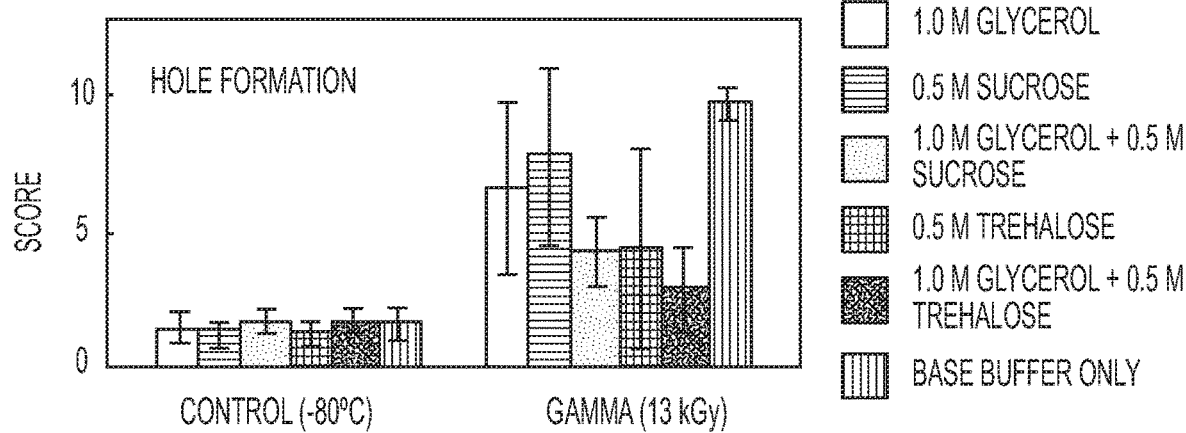
FIGS. 3A-3C are a series of bar graphs depicting the change of histological scores after cold (−80° C.) gamma irradiation for tissue matrices, according to certain embodiments.
Figure 3B:
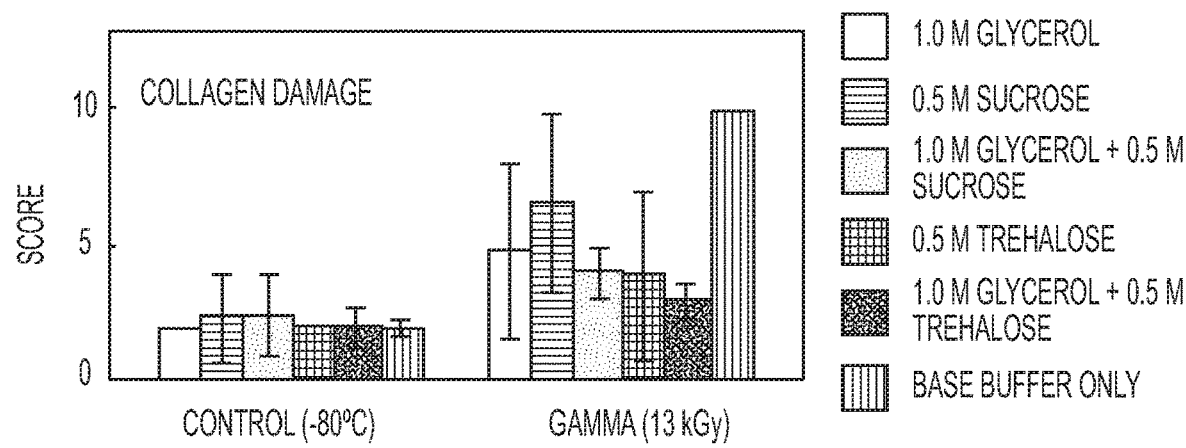
Figure 3C:
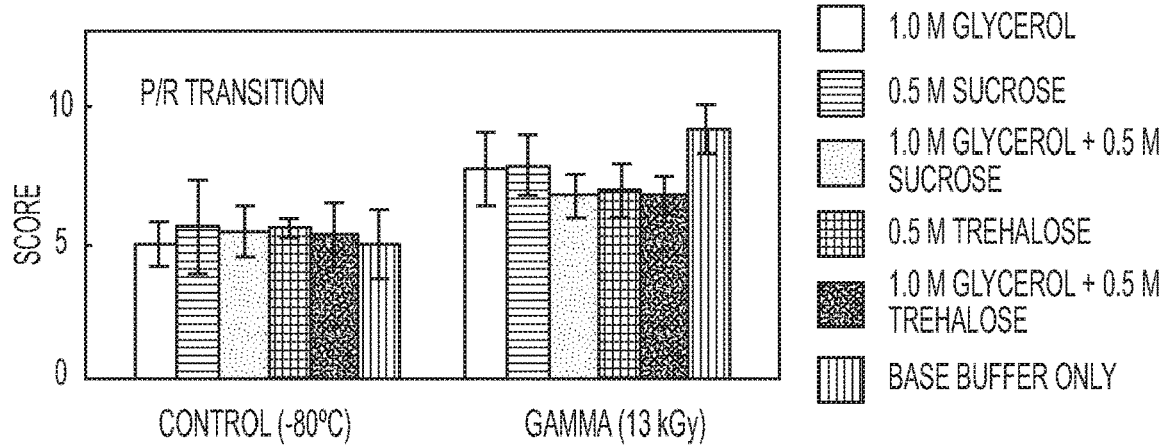

FIGS. 3A-3C depict differences between stabilizers and their combinations in tissue protection against radiation damage. The top left graph depicts the histological scoring for "hole formation;" the top right graph depicts the histological scoring for "collagen damage;" and the lower left graph depicts the histological scoring for the P/R transition, for an ATM (preserved in a variety of different types of solutions; see figure key). The data is presented as a mean±a standard deviation of 5 donor lots. A combination of glycerol and trehalose offered the highest quality preservation as determined by tissue histology in these experiments.

Example 5. Changes in Collagen Stability in a Preservation Solution after Gamma Irradiation at Ambient Temperature The protective role of the preservation solutions against the damaging effects of ionizing radiation was examined with decellularized human and porcine dermal tissue matrix. Skin tissue from one human donor was processed to remove epidermis and cells as described above in Example 4. Porcine tissue was processed by shaving and washing the skin, de-epidermalizing by soaking in 0.5% Triton X100 and 5.85% sodium chloride for about 44 hours, de-cellularizing by soaking in 2% sodium deoxycholate for 18 hours, and plucking remaining hairs manually.

The tissue was then washed with Dulbecco's PBS solution containing 5 mM EDTA (sodium salt) twice, and was incubated in a solution containing 7.2 mM citric acid, 22.8 mM sodium citrate, 6 mM EDTA (sodium salt), 100 mM sodium chloride, 300 mM mannitol, 15% (w/v) glycerol, 0.02% (w/v) TWEEN-20®, and 200 mM trehalose dihydrate. The amount of the solution added was 2 ml per gram decellularized tissue matrix. After incubation, the tissue matrix was packaged in film-to-film pouches. The film-to-film pouches were then packaged in secondary foil-to-foil pouches. The tissue matrix samples were then gamma-irradiated at a dose of 20 kGy.

After gamma irradiation, tissue samples were washed with 0.9% saline to remove protectants, and tissue damage was assessed using differential scanning calorimetric (DSC). DSC analysis measures the change of thermostability of tissue matrix. When collagen-based materials are heated to their denaturation temperature, heat-labile intramolecular cross-links are broken, and collagen molecules undergo the transition measured by DSC from a highly organized structure to a random gel-like state.

The effect of gamma irradiation on collagen-based tissue matrix was investigated using bovine insoluble collagen matrix of Archilles heel (Sigma Chemical Co., St Louis, Mo.) and human dermis matrix (acellular tissue matrix). Samples of acellular tissue matrix and bovine insoluble collagen matrix were gamma irradiated at a dose of 19 to 20 kGy. After gamma irradiation, tissue samples were rehydrated in 0.9% saline, and tissue damage was assessed using DSC.

Figure 4:
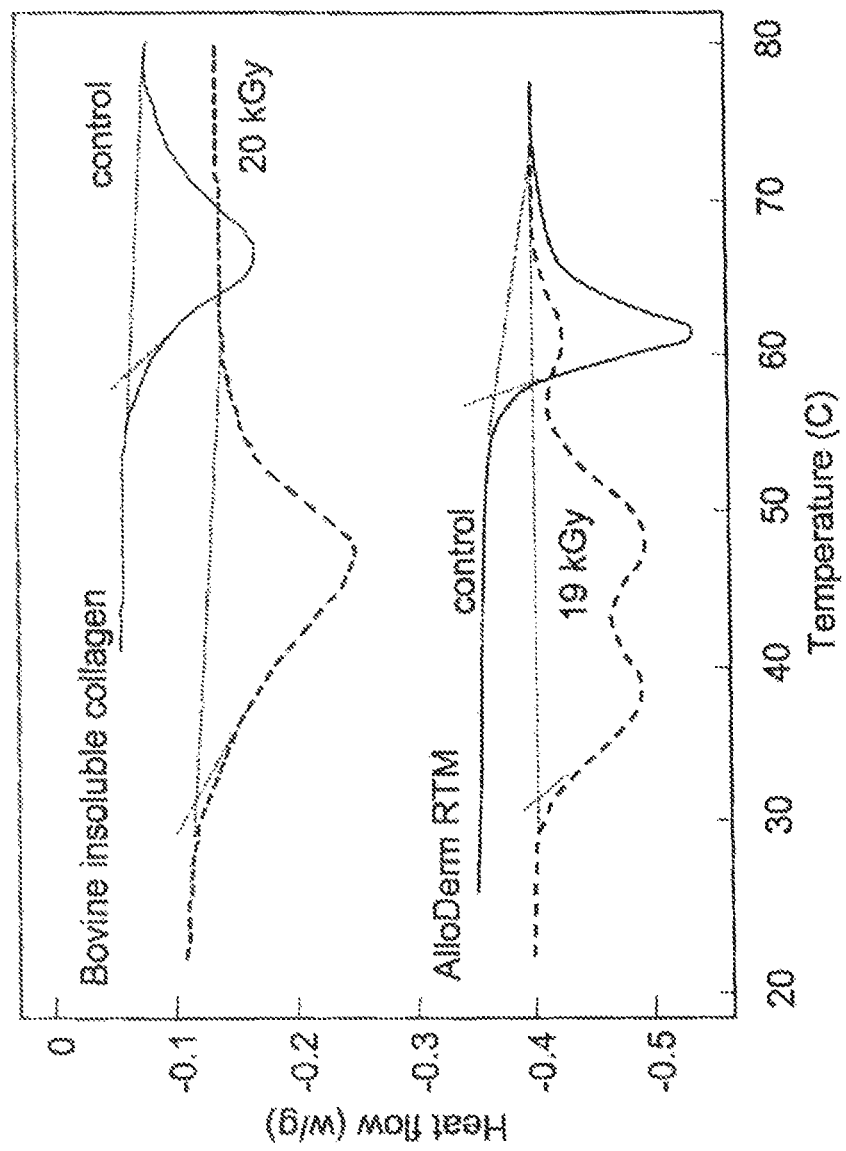
FIG. 4 is a series of thermograms of tissue matrices before and after gamma irradiation at ambient temperature, according to certain embodiments.

FIG. 4 is a series of thermograms of ATM (Alloderm® regenerative tissue matrix (RTM)) and bovine insoluble collagen matrix before and after 19 to 20 kGy gamma irradiation at ambient temperature, according to some embodiments. The Y-axis represents the heat flow (w/g) and the X-axis represents the temperature in ° C. Before gamma irradiation, the onset denaturation temperature was 58 to 60° C. for both bovine collagen matrix and acellular tissue matrix. After gamma irradiation, the onset denaturation temperature decreased to approximately 32° C., or below body temperature. Three separate domains appeared in gamma irradiated acellular tissue matrix. This DSC analysis predicted a partial, spontaneous denaturation of gamma-irradiated tissue matrix after implantation in vivo. The damage to the tissue matrix after gamma irradiation was also reflected by the significant increase in denaturation enthalpy (denaturation peak size).

Figure 5:
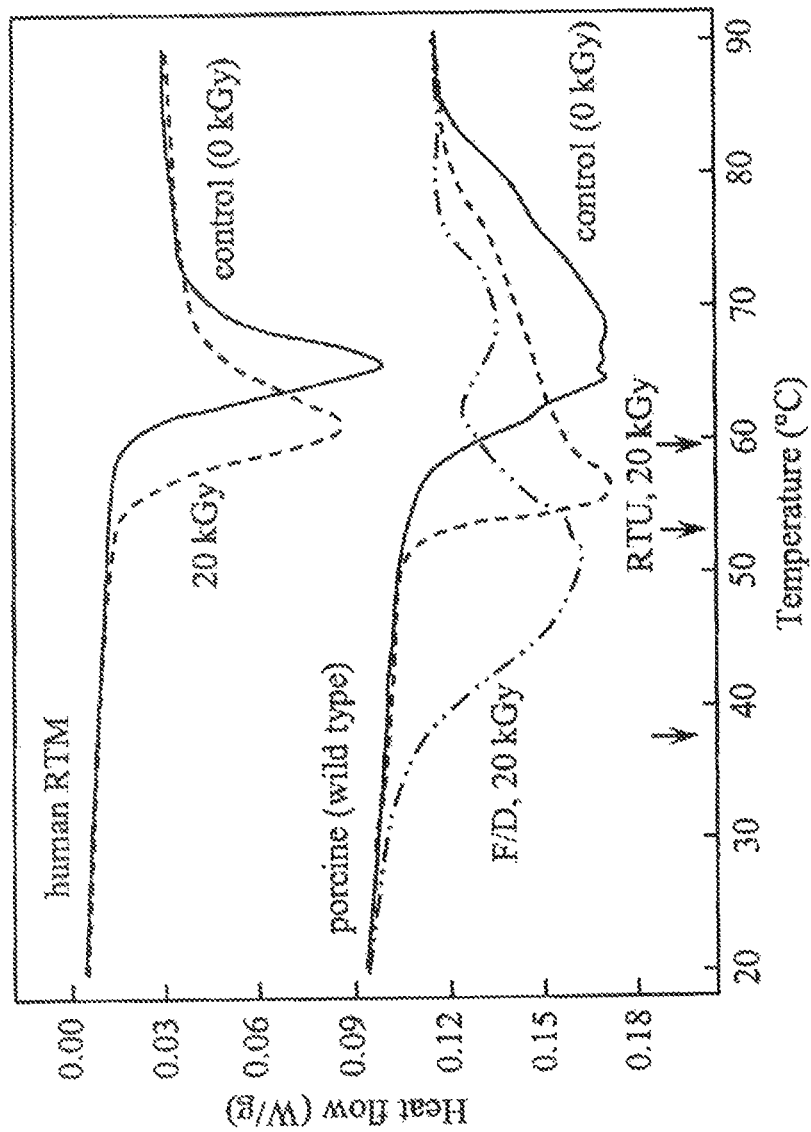
FIG. 5 is a series of thermograms of decellularized human and porcine dermal tissue matrices in an exemplary preservation solution before and after 20 kGy (kilogray) gamma irradiation at ambient temperature, according to certain embodiments.

FIG. 5 is a series of thermograms of decellularized human and porcine dermal tissue matrices in an exemplary preservation solution before and after 20 kGy gamma irradiation at ambient temperature. The Y-axis represents the heat flow (w/g) and the X-axis represents the temperature in ° C. Gamma irradiation (20 kGy) only caused a 4° C. decrease in the onset denaturation temperature in human dermal tissue matrix. The onset denaturation temperature of gamma irradiated human ATM remained to be as high as 56 to 57° C., in contrast to the onset denaturation temperature of −32° C. for the freeze-dried, gamma irradiated ATM. In addition, there was no domain separation in the tissue matrix preserved in the solution after gamma irradiation. The results for the porcine dermal tissue matrix were similar to the human dermal tissue matrix. The onset denaturation temperature of porcine tissue matrix in the preservation solution decreased only slightly from 58 to 59° C. to 53° C., whereas the onset denaturation temperature of freeze-dried porcine tissue decreased to 35 to 37° C., along with significant domain separation. The DSC results demonstrated that tissue matrix in the preservation solution was resistant to gamma irradiation damage.

Example 6. The Effect of 26 kGy Gamma Irradiation on Processed Porcine Tissue Matrix at Ambient Temperature The experiment compared the differences in tissue histology, collagen thermal stability, tensile properties, resistance of tissue matrix to collagenase and proteinase K degradation between freeze-dried porcine tissue matrix samples and samples preserved in a preservation solution.

In the experiment, pig skin tissue was decellularized as described in Example 5. Decellularized porcine dermal tissue matrix was also treated with DNAse and α-galactosidase. Processed porcine tissue matrix was cut into small sample pieces (1.5 cm×6.0 cm) in the same direction. Tissue samples were divided into four groups. Samples of two groups were packaged into TYVEK® pouches and freeze dried. Freeze-dried samples were then packaged in secondary foil-to-foil pouches. Samples of the other two groups were incubated in a preservation solution containing: 4 mM citric acid, 26 mM sodium citrate, 3 mM EDTA (sodium salt), 80 mM sodium chloride, 200 mM mannitol, 15% (w/v) glycerol, 0.02% (w/v) TWEEN-20®, and 400 mM trehalose dihydrate. The amount of the solution added was 2 ml per gram (g) of decellularized tissue matrix. After incubation, tissue matrix was packaged in film-to-film pouches. The film-to-film pouches were then packaged in secondary foil-to-foil pouches. One group of freeze-dried samples and one group of samples in the solution were gamma irradiated at a dose of 26 kGy at ambient temperature.

The change in tissue histology after gamma irradiation was examined using the histological method described in Example 4. Tissue samples were washed with PBS saline overnight, and fixed in 10% formalin. Samples were processed and stained with H&E.

After rinsing and rehydrating the tissue, the change in collagen thermal stability was measured using DSC. The change in tensile properties was tested using Instron after rinse and rehydration with 0.9% saline.

To determine the resistance of tissue samples against collagenase and proteinase K, tissue samples were first washed in 0.9% saline with gentle agitation. The saline solution was changed three times during the washing to remove protectants in the tissue samples. Washed samples were then freeze-dried and used for enzymatic analysis.

The susceptibility of tissue matrix to collagenase was measured with the following method. The stock solution of type I collagenase was prepared at 10 mg/ml in 10 mM Tris-HCl buffer (pH 7.5) containing 5 mM $CaCl_2$. Tissue samples of 20 to 30 mg dry mass were rehydrated in 2.0-ml Eppendorf tubes with 1.5 mL of Tris-HCl buffer at 2 to 8° C. overnight. Samples were centrifuged at 12,000 rpm for 5 minutes, and the supernatant containing protectants was discarded. Tissue samples were re-suspended in 1.5 ml of Tris-HCl buffer, and centrifuged again to wash out the remaining protectant. Washed tissue samples were resuspended again with 1.5 ml of pre-warmed (37° C.) Tris-HCl buffer, and 60 µl of collagenase stock solution was added for each sample. Enzyme digestion was performed for 3 and 7 hours at 37° C. with gentle agitation. At the end of collagenase digestion, samples were centrifuged and washed twice with distilled water. Pelleted tissue samples were freeze dried, and the resistance of tissue matrix to type I collagenase digestion was determined according to the dry weight of tissue remaining after digestion.

The susceptibility of tissue matrix to proteinase K was measured with the following method. Proteinase K stock solution was prepared at 10 mg/ml in 10 mM Tris-HCl (pH 7.5) containing 2 mM $CaCl_2$ and 50% glycerol (w/v). Samples of 20 to 30 mg dry mass were rehydrated in 2.0-ml Eppendorf tubes with 1.5 mL of 10 mM Tris-HCl buffer (pH 7.5) containing 2 mM $CaCl_2$ at 2 to 8° C. overnight. Samples were centrifuged at 12,000 rpm for 5 minutes, and the supernatant was discarded. Tissue samples were re-suspended in 1.5 ml of fresh Tris-HCl buffer, and 30-µl proteinase K stock solution was added to each sample for digestion at 50° C. The resistance of tissue matrix to proteinase K digestion was determined by weight after centrifugation, washing, and freeze drying.

DSC analysis showed that freeze drying did not affect the thermal stability of the tissue matrix. The onset denaturation temperature was 60.8±0.7° C. (N=6) and 60.0±0.9° C. (N=5) for freeze-dried samples and samples in preservation solution, respectively. However, upon exposure of the matrix to 26 kGy gamma irradiation, the onset denaturation temperature of freeze-dried samples decreased to 37.8±0.6° C. (N=4), whereas the onset denaturation temperature of the matrix samples treated with preservation solution was 53.3±1.1° C. (N=4). The depression of the onset denaturation temperature was 23° C. in freeze-dried samples in comparison to 7° C. in samples treated with preservation solution.

FIGS. 6A and 6B are a pair of bar graphs depicting the tensile strength and stiffness of Yucatan porcine tissue matrix after 26 kGy gamma irradiation. The data is presented as a mean±standard deviation of the values obtained from 4 replicates. The left graph depicts the Maximum strength (Y-axis) of the tissue matrix treated with 26 kGy gamma irradiation without (F/D) or with a preservation solution (RTU). The right graph depicts the Stiffness (Y-axis) of the tissue matrix treated with 26 kGy gamma irradiation without (F/D) or with a preservation solution (RTU)

Gamma irradiation at 26 kGy reduced the tensile strength and stiffness of porcine tissue matrix. For freeze-dried tissue samples, tensile strength was reduced by more than 90%, and tissue stiffness was reduced by ~85%. Pig tissue matrix samples incubated in the preservation solution were more resistant to gamma irradiation damage. Tensile strength and tissue stiffness of the samples in preservation solution was reduced by only ~25%.

Figure 7:
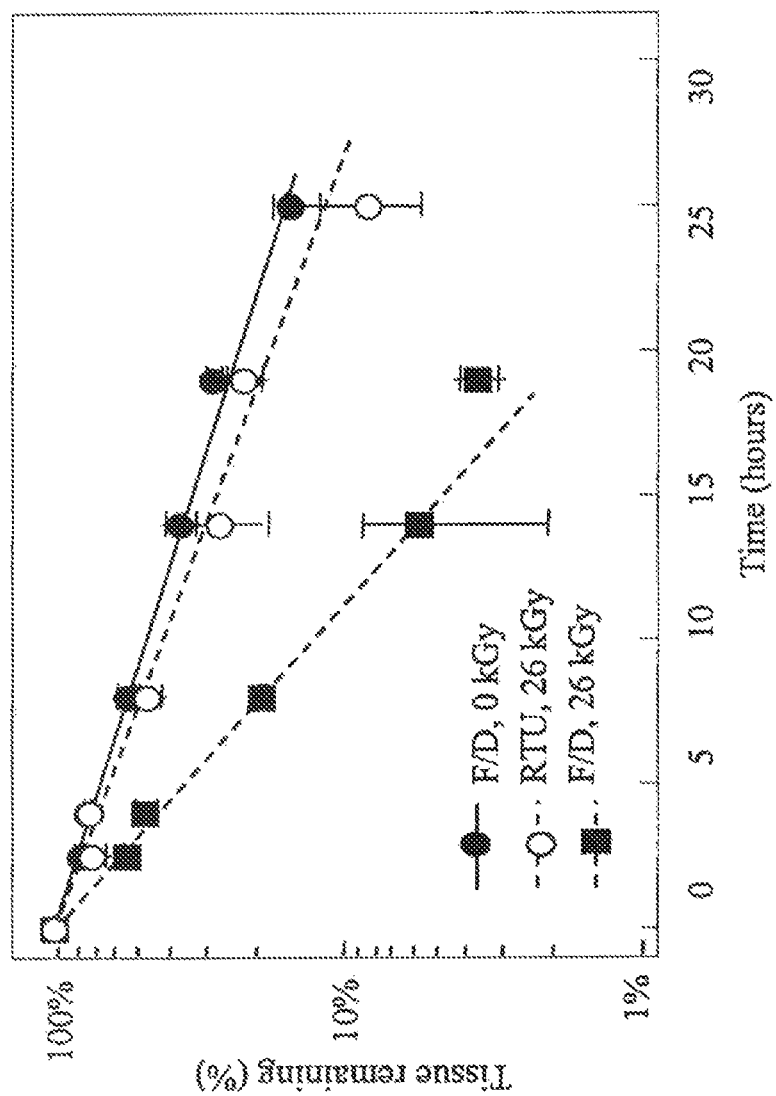
FIG. 7 is a line graph depicting the resistance of Yucatan porcine tissue matrix against collagenase digestion after gamma irradiation, according to certain embodiments.

Type I collagen is the predominant component of the porcine ATM (pATM). The susceptibility of gamma-irradiated pATM to enzyme degradation was evaluated in vitro using type I collagenase. FIG. 7 is a line graph depicting the resistance of Yucatan porcine tissue matrix against collagenase digestion after gamma irradiation. The data is presented as mean±standard deviation of three replicates (N=3). The Y-axis represents the percentage of tissue remaining and the X-axis represents time. The line denoted by filled circles represents the rate of digestion of tissue matrix that was not treated with preservation solution or gamma irradiation. The line denoted by the filled squares represents the rate of digestion of tissue matrix that was treated with gamma irradiation. The line denoted by the empty circles represents the rate of digestion of tissue matrix that was treated with preservation solution and gamma irradiation. The rate constant (i.e., slope) of tissue degradation in freeze-dried pATM increased by ~160% from 0.07 to 0.179 after 26 kGy gamma irradiation, whereas that value of the pATM treated with the solution was only increased by ~20% to 0.083 after gamma irradiation.

In addition to a collagenase degradation assay, another proteolytic enzyme (proteinase K) was also used to examine the tissue matrix integrity after gamma irradiation. Proteinase K is an enzyme that cleaves peptide bonds at the carboxylic sides of aliphatic, aromatic or hydrophobic amino acids, and is known to have higher affinity to proteins that have destabilizing conformational changes and are partially unfolded or damaged. The susceptibility to proteinase K degradation can indicate small protein structural changes.

Figure 8:
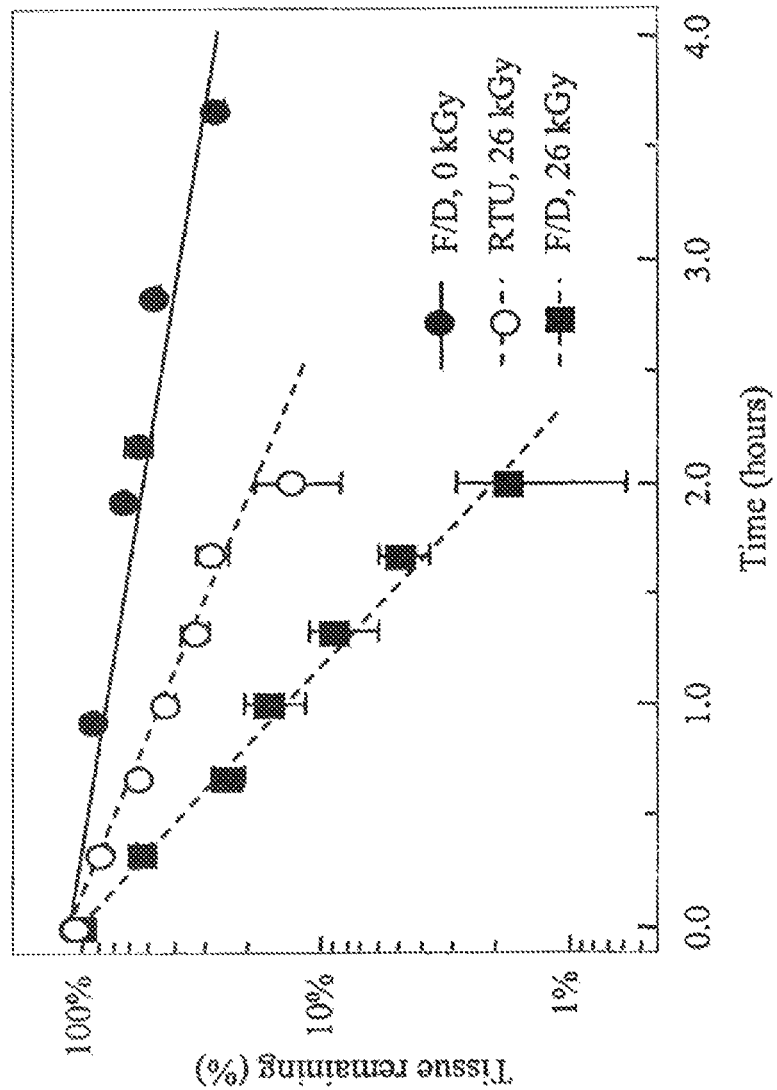
FIG. 8 is a line graph depicting the resistance of Yucatan porcine tissue matrix against proteinase K digestion after gamma irradiation, according to certain embodiments.

FIG. 8 is a line graph depicting the resistance of Yucatan tissue matrix against proteinase K digestion after gamma irradiation. The data is presented as mean±standard deviation of three replicates (N=3). The Y-axis represents the percentage of tissue remaining and the X-axis represents time. The line denoted by filled circles represents the rate of digestion of tissue matrix that was not treated with preservation solution or gamma irradiation. The line denoted by the filled squares represents the rate of digestion of tissue matrix that was treated with gamma irradiation. The line denoted by the empty circles represents the rate of digestion of tissue matrix that was treated with preservation solution and gamma irradiation.

The 1st order kinetic plots showed a marked increase in the rate constant of tissue matrix degradation in freeze-dried samples after gamma irradiation. Gamma irradiation also increased the rate constant of tissue matrix degradation in the samples in solution, but to a much less extent, suggesting less structural modification upon gamma irradiation.

Example 7. The Effect of Gamma Irradiation Dose on Human Tissue Matrix at Ambient Temperature The following experiment demonstrated that minimal modification to a tissue matrix occurs when it is preserved in an exemplary solution and dosed with 0, 5, 10, 15, 20, or 25 kGy of gamma irradiation.

The exemplary protective solution used in the experiment contained: 4.0 mM citric acid, 26 mM sodium citrate, 6 mM EDTA, 100 mM sodium chloride, 300 mM mannitol, 15% (w/v) glycerol, 0.03% (w/v) TWEEN-20®, and 300 mM trehalose.

Four lots of human donor skin tissue were processed as described above. After washing with Dulbecco's PBS solution twice, decellularized tissues were treated with 0.1% PAA for 3 hours. Then the tissue matrices were placed in the protective solution overnight.

For each donor lot, six orientation-paired (3×7 cm) pieces were cut from the same large piece of skin tissue. These matched samples were used for biomechanical testing after gamma irradiation. In addition, 24 (2×2 cm) small pieces were cut for DSC and histological evaluation after gamma irradiation. Samples (sample 6 and 24) were placed into a 125 mL bottle and incubated in the solution at a volume ratio of 2 to 1 (2 mL solution per 1 g processed tissue) for 48 to 72 hours.

After incubation, tissue samples were removed from the solutions and packaged into film-to-film pouches. One paired piece and 4 small unpaired pieces were packaged into one pouch. The film-to-film pouches were packaged in secondary foil-to-foil pouches. Packaged tissue samples were gamma-irradiated for 0, 5, 10, 15, 20, or 25 kGy at an ambient temperature.

Calorimetric Analysis of Tissue Matrix Integrity.

Tissue samples were washed with PBS saline overnight, and evaluated by differential scanning calorimeter (DSC) to determine the onset denaturation temperature and denaturation enthalpy after gamma irradiation. Three samples from different tissue pieces were analyzed for each gamma dose level.

Histological Evaluation.

Tissue samples were washed with PBS saline overnight and were then fixated in 10% formalin. Samples were processed and stained with H&E. Standard histological evaluation was carried out as describe in Example 4 above. Three samples from different tissue pieces were evaluated for each gamma dose level.

Biomechanical Test.

After irradiation, paired samples were rinsed with 0.9% saline for ~1 hour. Each paired sample was cut into two 1×7 cm samples. Tensile strengths of the samples were tested using an Instron system (described above).

After the biomechanical test, tissue samples were washed in 0.9% saline with gentle agitation. The saline solution was changed three times during washing. The extended washing step was meant to rinse out any protectant within tissue matrix. Washed samples were then freeze-dried and used for enzymatic analysis.

The susceptibility of tissue matrices to collagenase degradation was measured (as described above). The half life was used to express the resistance of tissue matrix to type I collagenase digestion. The susceptibility of gamma-irradiated tissue to trypsin digestion was determined according to the following method. Samples (20-30 mg) of freeze-dried tissue were placed into 2.0 ml Eppendorf tubes, and 1.5 ml Tris-HCl buffer (100 mM Tris-HCl, 2 mM $CaCl_2$, pH 7.6) was added to rehydrate tissue overnight at 2 to 8° C. An aliquot of 100 μl trypsin stock solution (20 mg/mL trypsin in 1 mM HCl with 20 mM $CaCl_2$) was mixed by gentle inversion, and samples were incubated at 37° C. for 40-48 hours. At the completion of digestion, samples were centrifuged for 5 minutes at 12,000 rpm, and the supernatant was discarded. Pellets were washed with 1.5 ml of milli-Q water and centrifuged again for 5 minutes at 12,000 rpm. Centrifuged tissue pellets were freeze dried, and the remaining tissue weight was determined. The loss of tissue was used to express the resistance to trypsin degradation.

Figure 9:
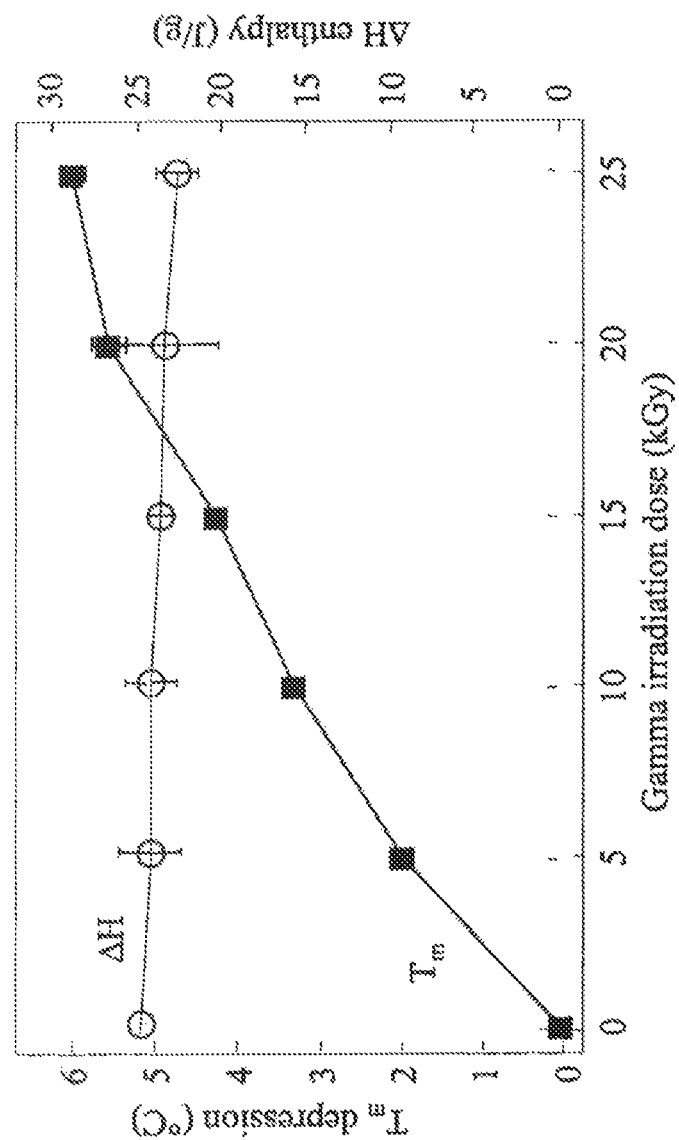
FIG. 9 is a line graph depicting the depression of the onset tissue matrix denaturation temperature and denaturation enthalpy after gamma irradiation for a tissue matrix in an exemplary preservation solution, according to certain embodiments.

FIG. 9 is a line graph depicting the depression of the onset tissue matrix denaturation temperature and denaturation enthalpy after gamma irradiation for a tissue matrix in an exemplary preservation solution. The data is presented as mean±standard deviation of four donor lots. The Y-axis represents the $T_m$ depression (in ° C.; left) or the ΔH enthalpy (right) and the X-axis represents the dosage of gamma irradiation. The line denoted by empty circles represents the ΔH and the line denoted by the filled squares represents $T_m$.

DSC analysis (FIG. 9) showed a depression of the onset tissue matrix denaturation temperature ($T_m$ depression) up to 6° C. upon gamma irradiation at 25 kGy. The extent of the onset $T_m$ depression was dose-dependent. There was no significant change in denaturation enthalpy between control and irradiated samples. The observed change in tissue matrix integrity after gamma irradiation for matrices in the solution was very small when compared to freeze-dried tissue matrix (compare to the results shown in Examples 5 and 6).

Figure 10:
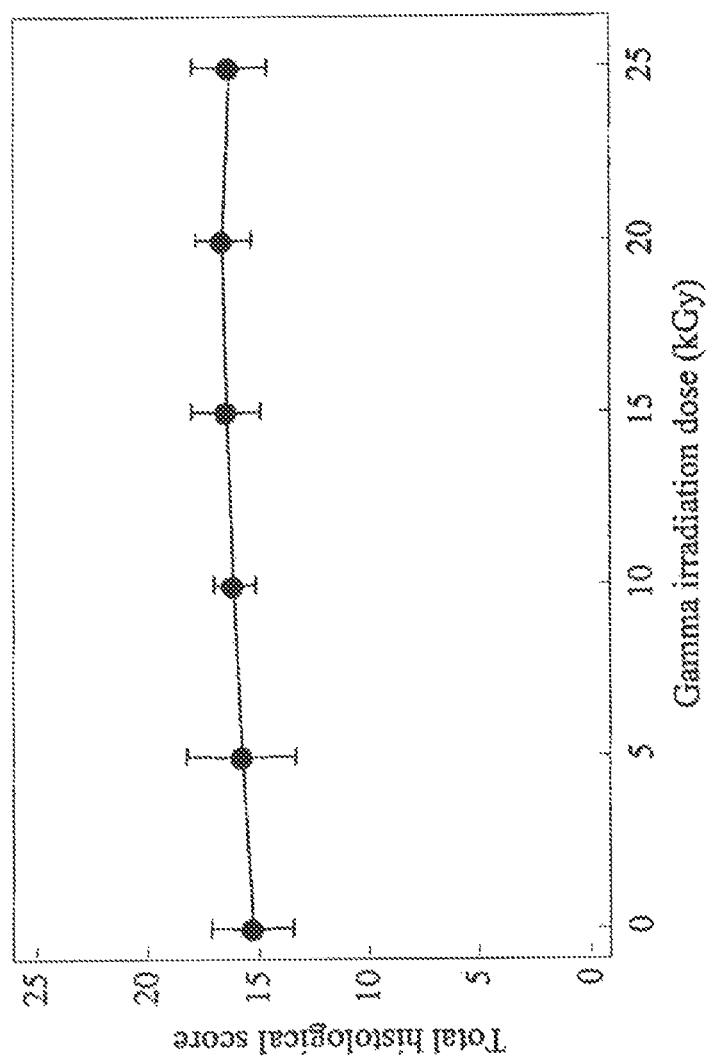
FIG. 10 is a line graph depicting the change of total histological scores of a tissue matrix exposed to a dose of gamma irradiation up to 25 kGy, according to certain embodiments.

FIG. 10 is a line graph depicting the change of total histological scores of a tissue matrix exposed to a dose of gamma irradiation up to 25 kGy. The data is presented as mean±standard deviation of four donor lots. Histological evaluation also showed no significant change in total histological scores in tissue matrix samples after gamma irradiation in the preservation solution.

Figure 11:
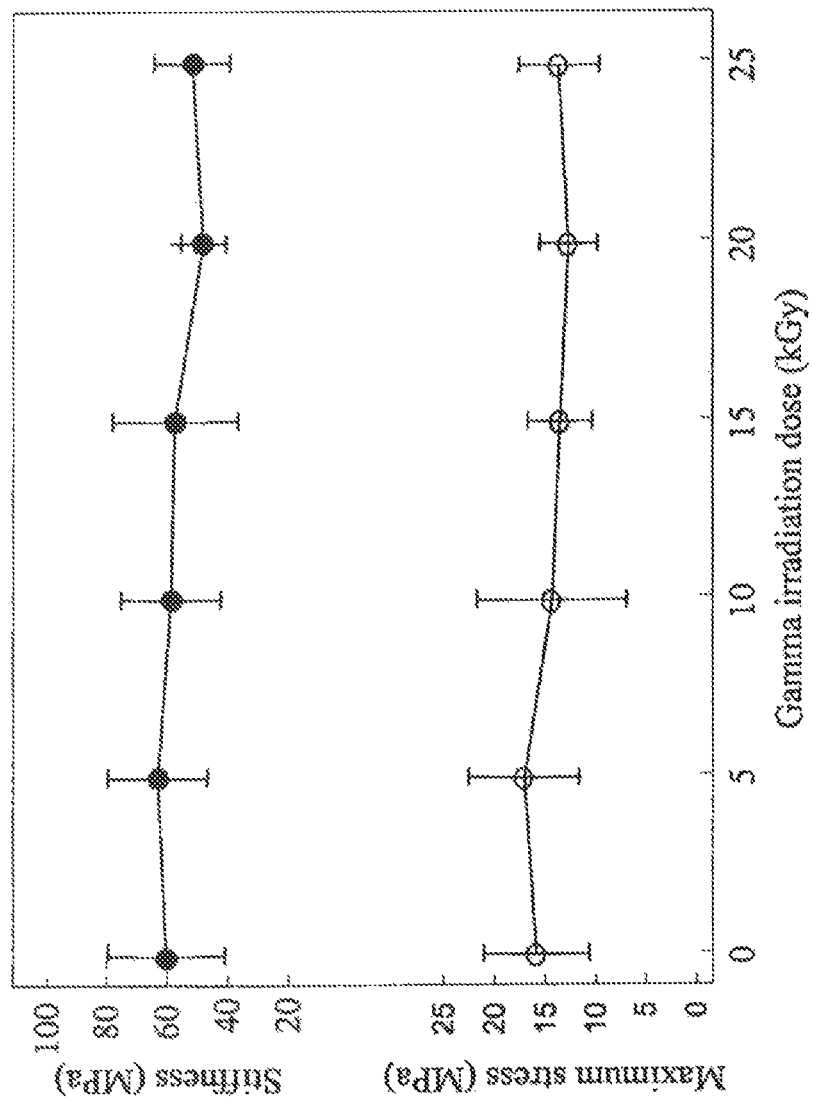
FIG. 11 is a line graph depicting changes in stiffness and strength of a tissue matrix after gamma irradiation, according to certain embodiments.

FIG. 11 is a pair of line graphs (split) depicting changes in stiffness and strength of a tissue matrix after gamma irradiation up to 25 kGy. The data is presented as mean±standard deviation of four donor lots. The upper line represent the Stiffness of the tissue matrix (filled circles) and the lower line represents the maximum stress (empty circles) by dose of gamma irradiation (X-axis). Tensile testing (FIG. 11) showed that no significant change in stiffness and strength of tissue matrix samples occurred for matrices in the preservation solution when exposed to gamma irradiation.

Figure 12A:
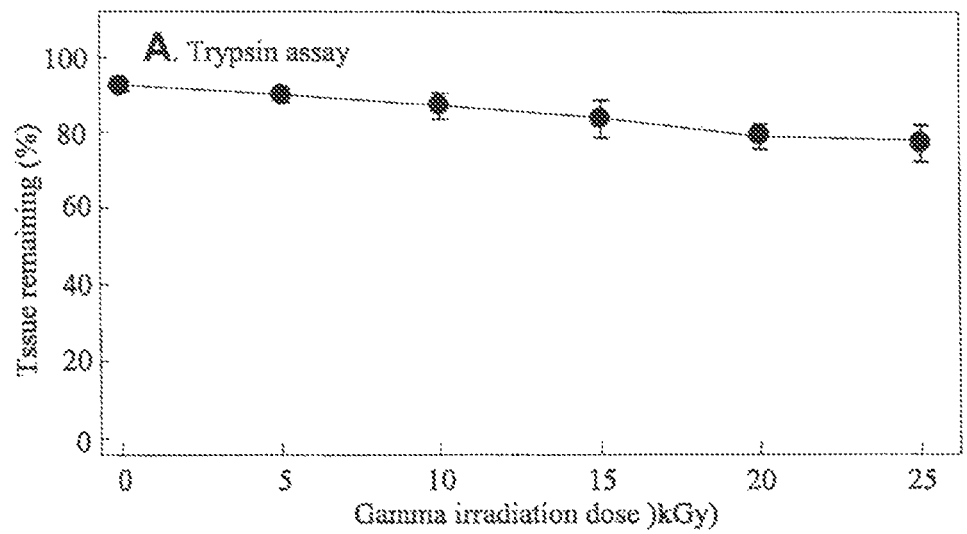
FIGS. 12A and 12B are a pair of line graphs depicting the resistance of a tissue matrix against trypsin and collagenase digestion after gamma irradiation, according to certain embodiments.
Figure 12B:
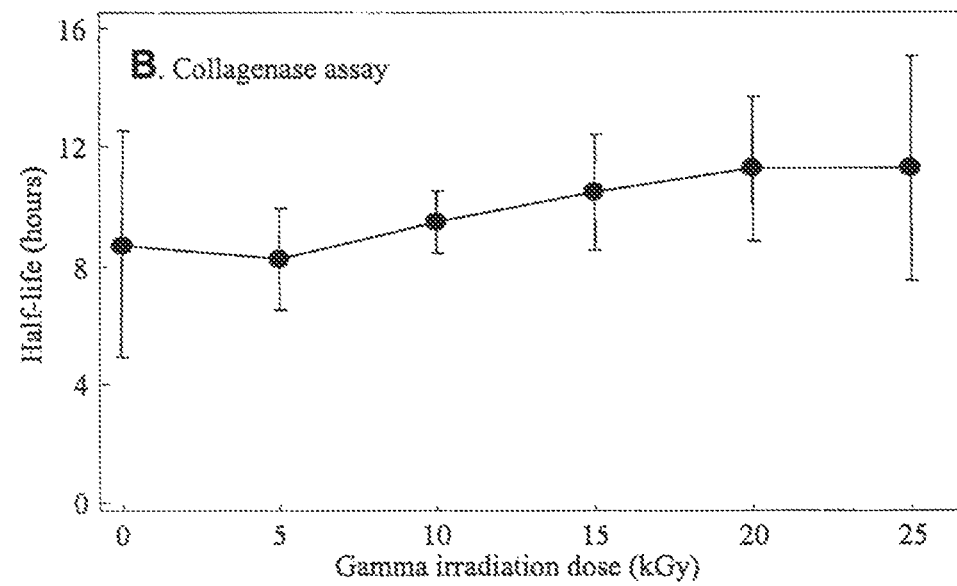

FIGS. 12A and 12B are a pair of line graphs depicting the resistance of a tissue matrix against trypsin and collagenase digestion after gamma irradiation. The data is presented as mean±standard deviation of four donor lots. The upper graph (A) depicts the rate of digestion of the tissue matrix by trypsin. The lower graph (B) depicts the rate of digestions of the tissue matrix by collagenase. Trypsin and collagenase digestion studies also showed insignificant changes in the resistance of tissue matrix against enzyme degradation after gamma irradiation (FIGS. 12A-12B).

Example 8. The Effect of Preservation Solution Variations

The preservation solutions consisted of biocompatible buffer agents, osmolyte, surfactant, reducing agents, transition metal chelator and other stabilizers (e.g., glycerol, mannitol and trehalose). Because some components may play multiple roles in preserving tissue matrix materials, there could be many variations in preservation solution formulation. An important bulk property of those solutions is a water activity between 0.930 to 0.995, which allows adequate hydration of tissue matrix to be pliable while at the same time retards adventitious deleterious processes during storage.

In the following experiment, the effect of variation of concentrations of trehalose and mannitol was tested. The base solution contained: 4.0 mM citric acid, 26 mM sodium citrate, 5 mM sodium EDTA, 80 mM NaCl, 15% (w/v) glycerol, and 0.02% (w/v) TWEEN-20®. The base solution was test solution #1. Test solution #2 contained additional 300 mM trehalose and 300 mM mannitol. Test solution #3 additional contained 100 mM trehalose and 100 mM mannitol. Test solution #4 contained additional 100 mM trehalose and 300 mM mannitol. Test solution #5 contained additional 300 mM trehalose and 100 mM mannitol.

Decellularized human dermal tissue matrix (produced as describe in Example 4) was incubated in these five solutions in a ratio of 2 ml preservation solution per g tissue. After incubation, tissue samples were packaged into film-to-film pouches that were packaged in secondary foil pouches. Packaged tissue samples were gamma-irradiated with 9 or 26 kGy at ambient temperature. Freeze-dried, non-irradiated samples were used as control samples. Tissue histology, tensile strength, and collagen stability were measured after gamma irradiation.

Table 2 shows the results of histological evaluation. There were no significant differences between the five solutions for human dermal tissue matrix after gamma irradiation of 9 and 26 kGy.

TABLE 2

Histological scores (H & E stain) of tissue matrix samples in five preservation solutions after gamma irradiation.

| Methods | No. of donor lots | Gamma dose (kGY) | Holes | Collagen damage | Papillary to reticular transition |
|---|---|---|---|---|---|
| FD | 8 | 0 | 3.4 ± 1.0 | 4.7 ± 1.0 | 7.0 ± 0.9 |
| RTU#1 | 7 | 9 | 3.0 ± 0.0 | 3.9 ± 0.9 | 7.0 ± 0.8 |
| RTU#2 | 7 | 9 | 2.9 ± 0.7 | 3.9 ± 0.9 | 6.3 ± 0.8 |
| RTU#3 | 7 | 9 | 3.0 ± 0.8 | 4.1 ± 1.3 | 7.1 ± 1.1 |
| RTU#4 | 7 | 9 | 3.1 ± 1.1 | 4.1 ± 1.2 | 7.0 ± 1.2 |
| RTU#5 | 7 | 9 | 2.9 ± 0.7 | 4.1 ± 1.1 | 6.9 ± 1.1 |
| RTU#1 | 8 | 26 | 2.1 ± 0.6 | 4.9 ± 1.0 | 7.1 ± 0.8 |
| RTU#2 | 8 | 26 | 2.5 ± 0.8 | 4.6 ± 1.2 | 7.0 ± 0.9 |
| RTU#3 | 8 | 26 | 2.3 ± 0.5 | 4.9 ± 1.4 | 7.4 ± 0.7 |
| RTU#4 | 8 | 26 | 2.1 ± 0.6 | 4.4 ± 1.1 | 6.9 ± 1.1 |
| RTU#5 | 8 | 26 | 2.1 ± 0.7 | 5.3 ± 1.3 | 7.6 ± 1.0 |

Table 3 shows the tensile strength and tissue stiffness of gamma-irradiated tissue matrices in each of the different test solutions. In comparison to freeze-dried, non-irradiated tissue samples, the tensile strength and stiffness of tissue samples in the solutions did not change after gamma-irradiation at 26 kGy.

TABLE 3

Tensile strength of tissue matrix samples in five preservation solutions after gamma irradiation

| Methods | No. of lots | Dose (kGy) | Strength (MPa) | Stiffness (MPa) |
|---|---|---|---|---|
| FD | 6 | 0 | 12.4 ± 3.4 | 50.0 ± 12.3 |
| RTU1 | 6 | 26 | 13.1 ± 4.4 | 44.5 ± 11.8 |
| RTU2 | 6 | 26 | 13.7 ± 2.0 | 46.3 ± 7.9 |
| RTU3 | 6 | 26 | 13.6 ± 2.5 | 47.1 ± 7.0 |
| RTU4 | 6 | 26 | 12.7 ± 2.5 | 46.1 ± 7.4 |
| RTU5 | 6 | 26 | 12.4 ± 4.3 | 45.1 ± 11.1 |

Table 4 shows the collagen thermal stability of irradiated tissue matrices in each of the preservation solutions. Gamma irradiation (9 and 26 kGy) slightly decreased collagen stability of tissue samples in preservation solutions. In comparison to the freeze-dried, non-irradiated tissue products, the onset denaturation temperature decreased by ~3 to 5° C.

TABLE 4

The onset denaturation temperature of tissue matrix samples in five preservation solutions after gamma irradiation.

| Methods | Gamma Dose (kGy) | Onset Tm (° C.) |
|---|---|---|
| FD | 0 | 61.8 ± 0.7 |
| RTU#1 | 9 | 58.4 ± 0.7 |
| RTU#2 | 9 | 58.9 ± 0.7 |
| RTU#3 | 9 | 59.1 ± 0.9 |

TABLE 4-continued

The onset denaturation temperature of tissue matrix samples in five preservation solutions after gamma irradiation.

| Methods | Gamma Dose (kGy) | Onset Tm (° C.) |
|---|---|---|
| RTU#4 | 9 | 58.7 ± 0.7 |
| RTU#5 | 9 | 59.0 ± 0.8 |
| RTU#1 | 26 | 56.1 ± 1.3 |
| RTU#2 | 26 | 56.6 ± 1.1 |
| RTU#3 | 26 | 56.3 ± 1.2 |
| RTU#4 | 26 | 56.2 ± 1.5 |
| RTU#5 | 26 | 56.4 ± 1.3 |

Example 9. Histological and Biochemical Evaluation of Human Dermal Matrix in Exemplary Preservation Solutions Subjected to E-Beam Irradiation of 10 and 20 kGy This experiment evaluated histological, biochemical and thermochemical properties of human dermal tissue matrix preserved in four exemplary preservation solutions after the E-beam irradiation (10 and 20 kGy). These exemplary preservation solutions contained different combinations of glycerol, trehalose and mannitol. The freeze-dried, non-irradiated samples were used as controls.

Solution #1 in the experiment was the base solution and contained 4 mM citric acid, 16 mM sodium phosphate (dibasic), 100 mM NaCl and 4 mM sodium EDTA. Solution #2 contained 12% (w/v) glycerol and 360 mM trehalose in the base solution. Solution #3 contained 12% (w/v) glycerol, 360 mM and 360 mM trehalose in the base solution. Solution #4 contained 4 mM citric acid, 26 mM sodium phosphate (dibasic), 100 mM NaCl, 5 mM sodium EDTA, 0.12% (w/v) TWEEN-20®, 12% (w/v) glycerol, 240 mM mannitol and 240 mM trehalose. The pH of solution #1 to #3 was 6.0, and the pH of solution #4 was 6.4.

Ten (10) human donor skin lots were de-epidermized and decellularized. Processed tissue matrices were rinsed and washed with Dulbecco's PBS solution. Tissue materials of each donor lot were divided into five groups. Four groups were incubated with the exemplary preservation solutions, and the other group was freeze dried and used as controls. The preservation solutions were added to bottles containing the processed tissues at a ratio of 3 ml solution per gram tissue, and the samples were incubated for at least 6 hours. After incubation, tissue samples were removed from the preservation solutions and packaged into film-to-foil pouches. The film-to-foil pouches were sealed in a second foil-to-foil pouch. The group of control tissue samples was incubated in a cryoprotectant solution and packaged in TYVEK® pouches for freeze drying. After freeze drying, samples were packaged into secondary foil-to-foil pouches. The packaged tissue samples (in preservation solution) were irradiated with E-beam of 10 and 20 kGy at ambient temperature.

Tissue samples were examined using a battery of histological, calorimetric, and biochemical tests. Histological evaluation was done using standard histological processing techniques, and tissue slides were H&E stained. DSC analysis and trypsin digestion assays were described above.

Biochemical analysis after E-beam irradiation included the determination of glycosaminoglycan (GAG) and tissue-bound lipid peroxidation by-products in the tissue matrix samples. The presence of GAG was detected using the cellulose acetate membrane method. Tissue-bound lipid peroxidation by-products were measured using the TBA (thiobabituric acid) method with malondialdehyde bis(dimethyl acetal) as a standard.

Histological evaluation showed much lower histological scores for the presence of holes, collagen damage, papillary-to-reticular layer transition than freeze-dried control samples. No significant difference was evident between groups subjected to 10 and 20 kGy E-beam irradiation in any solutions.

Results of GAG analysis are presented in Table 5. GAG analysis detected whether hyaluronic acid and chondroitin sulfate were present after incubation in the preservation solution and E-beam irradiation. E-beam irradiation did not eliminate the GAG species in the tissue.

TABLE 5

Results of GAG analysis of human dermal tissue matrix with Preservation Solutions and E-beam irradiation (10 and 20 kGy).

| Treatment | Lot# 33105 HA/CS | 30706 HA/CS | 31316 HA/CS | 30534 HA/CS | 40341 HA/CS | 34255 HA/CS | 32156 HA/CS | 41067 HA/CS | 41374 HA/CS | 36085 HA/CS |
|---|---|---|---|---|---|---|---|---|---|---|
| S0, e10 | −/+ | −/+ | −/+ | −/+ | −/+ | −/+ | −/+ | −/+ | −/+ | −/+ |
| S1, e10 | +/+ | +/+ | −/+ | +/+ | −/+ | +/+ | −/+ | −/+ | +/+ | −/+ |
| S2, e10 | +/+ | +/+ | +/+ | +/+ | +/+ | +/+ | −/+ | −/+ | +/+ | −/+ |
| S3, e10 | +/+ | +/+ | +/+ | +/+ | −/+ | +/+ | −/+ | +/+ | +/+ | −/+ |
| S0, e20 | +/+ | +/+ | −/+ | −/+ | −/+ | −/+ | −/+ | −/+ | −/+ | −/+ |
| S1, e20 | +/+ | −/+ | −/+ | +/+ | −/+ | +/+ | −/+ | +/+ | +/+ | −/+ |
| S2, e20 | +/+ | +/+ | +/+ | −/+ | −/+ | +/+ | −/+ | +/+ | −/+ | −/+ |
| S3, e20 | +/+ | +/+ | +/+ | +/+ | −/+ | +/+ | −/+ | +/+ | +/+ | −/+ |
| F/D | +/+ | +/+ | +/+ | +/+ | −/+ | +/+ | +/+ | +/+ | +/+ | −/+ |
| F/D, e20 | +/+ | +/+ | +/+ | +/+ | −/+ | +/+ | −/+ | +/+ | +/+ | −/+ |

HA—Hyaluronic acid; Cs—Chondroitin sulfate

HA—Hyaluronic acid; Cs—Chondroitin sulfate

Lot #refers to individual subjects from which the tissue samples used to make the ATMs were derived.

e10 or e20 refer to the dosage in kGy of E-beam irradiation that the ATMs were exposed to.

S0, S1, S2, or S3 refer to the preservation solution contacted to each ATM.

Figure 13:
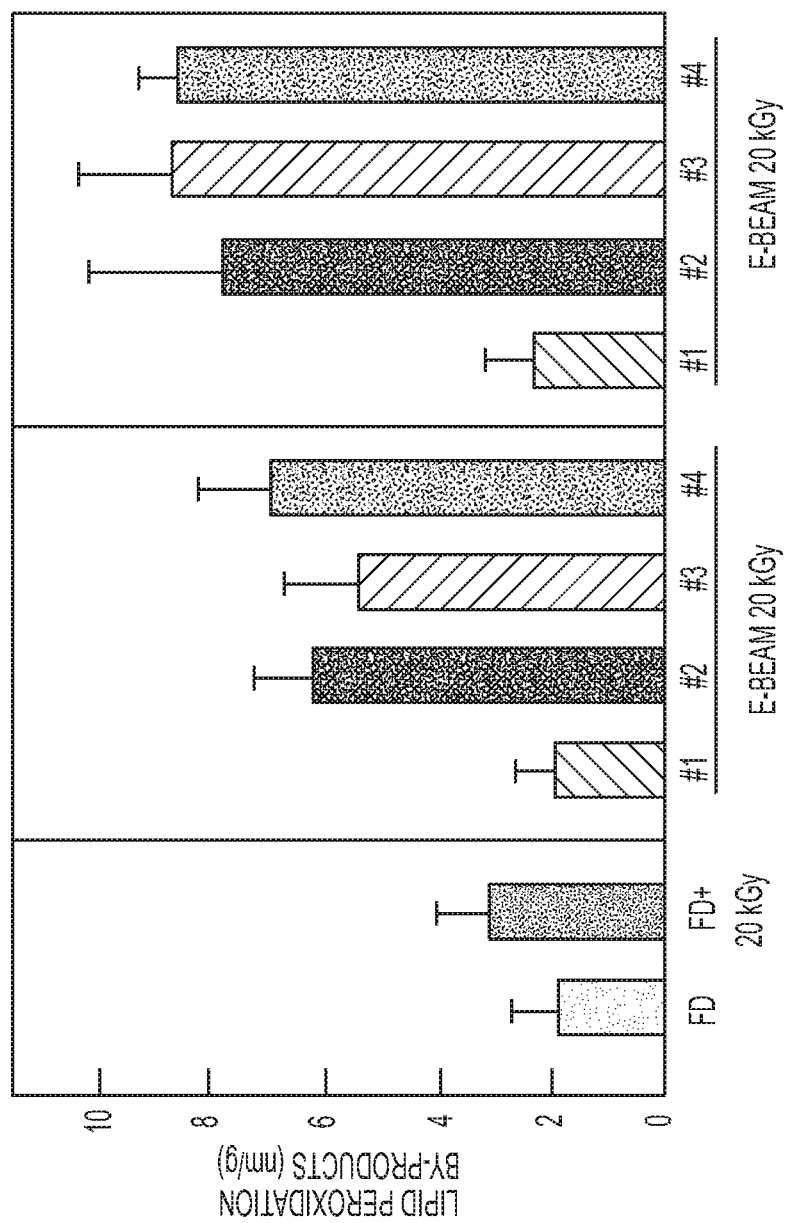
FIG. 13 is a bar graph depicting the content of tissue-bound lipid peroxidation by-products in tissue samples treated with exemplary preservation solutions and E-beam irradiation, according to certain embodiments.

Lipid peroxides are highly reactive by-products of polyunsaturated fatty acids. The formation of lipid peroxides in tissue may be induced by E-beam irradiation. Once formed, lipid peroxides will react with collagen and other protein molecules, covalently bind to tissue matrix, and potentially initiate tissue aging/degradation pathways (Maillard reactions). FIG. 13 is a bar graph depicting the content of tissue-bound lipid peroxidation by-products in tissue samples treated with exemplary preservation solutions (formulations 1 to 4) and E-beam irradiation (X-axis). Freeze-dried samples had very low lipid peroxidation by-products. Even after E-beam irradiation, the content of lipid peroxidation by-products remained low in freeze-dried samples and in samples in the #1 base buffer solution. Tissue samples treated with solutions #2, #3, or #4 contained much greater tissue bound lipid peroxidation by-products after E-beam irradiation, presumably because the presence of stabilizers slowed down the reaction between tissue matrix and reactive by-products.

Figure 14:
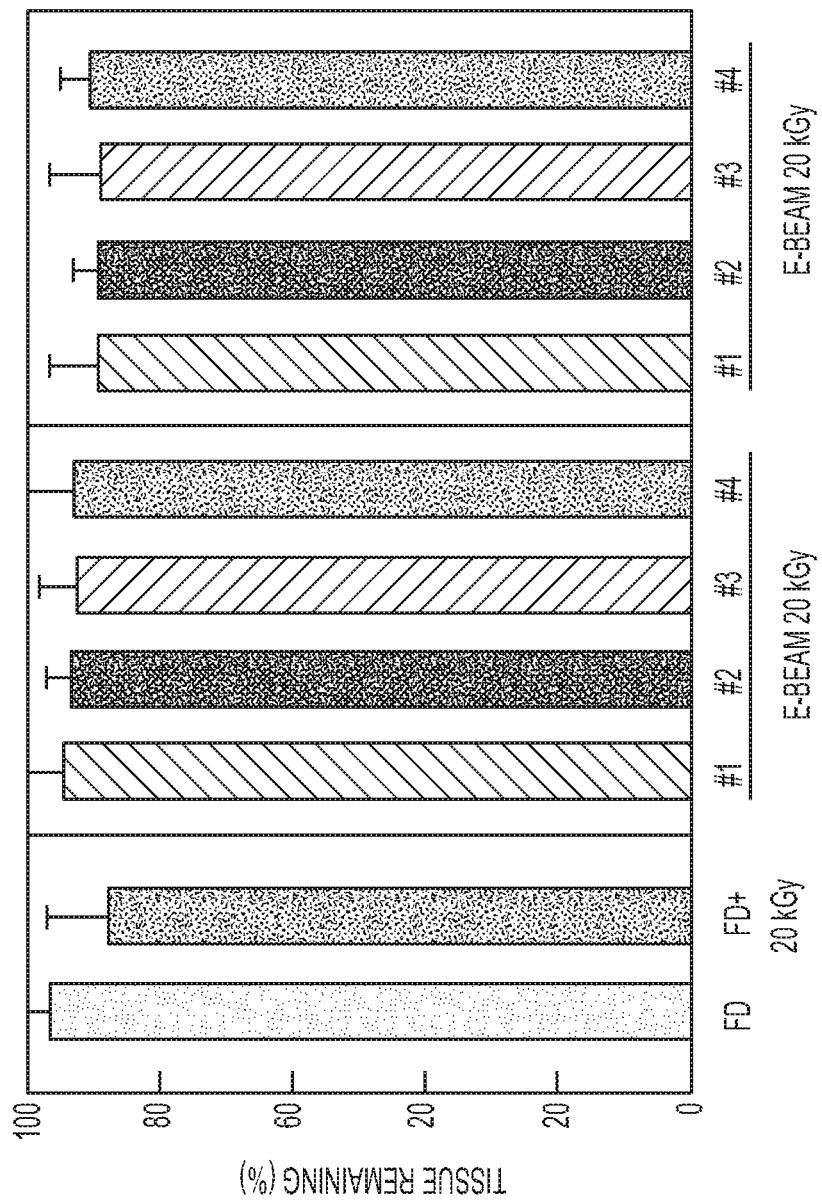
FIG. 14 is a bar graph depicting the results of a trypsin digestion assay for a human tissue matrix treated with exemplary preservation solutions and E-beam irradiaction, according to certain embodiments.

FIG. 14 is a bar graph depicting the results of a trypsin digestion assay for the human tissue matrix treated with exemplary preservation solutions (formulations 1 to 4) after 10 and 20 kGy E-beam irradiation (X-axis). Freeze-dried tissue was used for comparison. No difference in the susceptibility to trypsin digestion was observed between the four exemplary preservation solutions. However, E-beam irradiation of 20 kGy slightly increased tissue matrix digestion by trypsin.

Table 6 shows results of DSC analysis of tissue matrix samples in preservation solution after E-beam irradiation. E-beam irradiation decreased the onset denaturation temperature of tissue samples, and higher E-beam doses led to a greater decrease in onset temperatures. Tissue samples in preservation solutions had a significantly smaller decrease in the onset denaturation temperatures. No significant difference was evident in denaturation enthalpy between all treatments.

TABLE 6

DSC analysis results of tissue samples after E-beam irradiation.

| Tissue materials | E-beam dose (kGy) | Onset denaturation temperature (° C.) | Enthalpy (J/q) |
|---|---|---|---|
| Freeze-dried | 0 | 61.0 ± 1.0 | 21.1 ± 2.7 |
| Freeze-dried | 20 | 52.4 ± 1.8 | 21.9 ± 4.0 |
| #1 solution | 10 | 57.5 ± 1.8 | 20.9 ± 2.5 |
| #1 solution | 20 | 56.1 ± 1.6 | 19.7 ± 2.1 |
| #2 solution | 10 | 58.4 ± 1.6 | 20.5 ± 2.3 |
| #2 solution | 20 | 56.6 ± 1.5 | 21.0 ± 2.0 |
| #3 solution | 10 | 58.6 ± 1.1 | 20.9 ± 2.4 |
| #3 solution | 20 | 56.2 ± 1.4 | 20.4 ± 3.6 |
| #4 solution | 10 | 58.5 ± 1.1 | 20.2 ± 3.3 |
| #4 solution | 20 | 56.6 ± 1.8 | 21.1 ± 3.1 |

Example 10: Water Content of De-Cellularized Human Dermis and Effect of Tissue Hydration on Collagen Stability and Resistance to Gamma Irradiation-Induced Damage The radiolysis of water molecules is considered to be a factor that contributes to the damage of a tissue exposed to radiation such as high energy electrons and gamma rays. When a water molecule is irradiated, it becomes $H^+$ and $OH^-$, which then diffuse to and react with proteins and other macromolecules. In a protein solution, this action of radiation accounts for 99.9% of the irradiation damage to proteins (Kempner, 2001, Journal of Pharmaceutical Sciences, 90:1637-1646). Thus, the water content of tissue can affect the degree of tissue damage caused by ionizing irradiation. It has been reported that protein and tissue damage by ionizing irradiation could be reduced by freezing or immobilizing water molecules and thus limiting the diffusion of radiation byproducts. However, it has been discovered that freeze-dried tissue displays more histologic damage than some wet tissues upon radiation, and complete drying may not be desirable for some tissues. Thus, the problem appears to be complex, and there is a need to determine the optimal tissue hydration range at which irradiation damage can be minimized. The following experiments provide a method for determining the optimal hydration range for tissue sterilization by ionizing irradiation.

Figure 15:
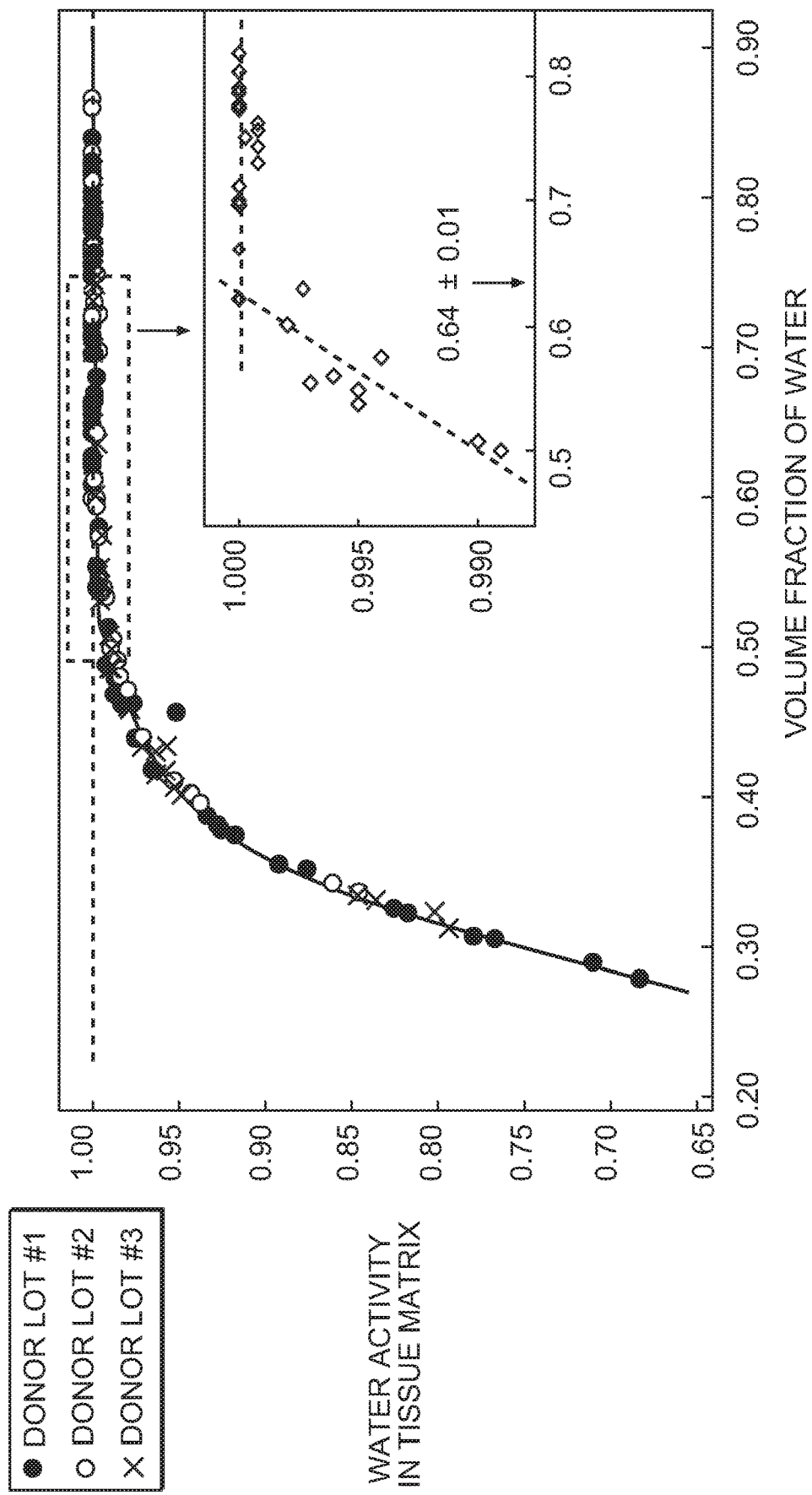
FIG. 15 is a line graph depicting the relations between water activity and volume fraction of water in a tissue matrix, according to certain embodiments.

Processed porcine tissue (produced as described in Example 5) was rinsed and fully rehydrated in distilled water. Tissue samples of three donor lots were dehydrated at ambient temperature (22 to 24° C.) to different hydration levels (i.e. different water contents). Tissue samples at different water contents were hermetically sealed in conical tubes before measurements of water activity (25° C.) (AQUALAB 3TE) and water content (vacuum drying). The volume fraction of water in tissue matrix was calculated using a collagen density of 1380 kg m$^{-3}$. FIG. 15 shows the water relation plot of water activity against the volume fraction of water in decellularized tissue matrix.

Results revealed a threshold volume fraction of water (0.63±0.2, N=6 donor lots) for tissue matrix hydration. At any water content above this threshold level, water is in excess, and the tissue property remains unchanged with further increase in water content.

Figure 16A:
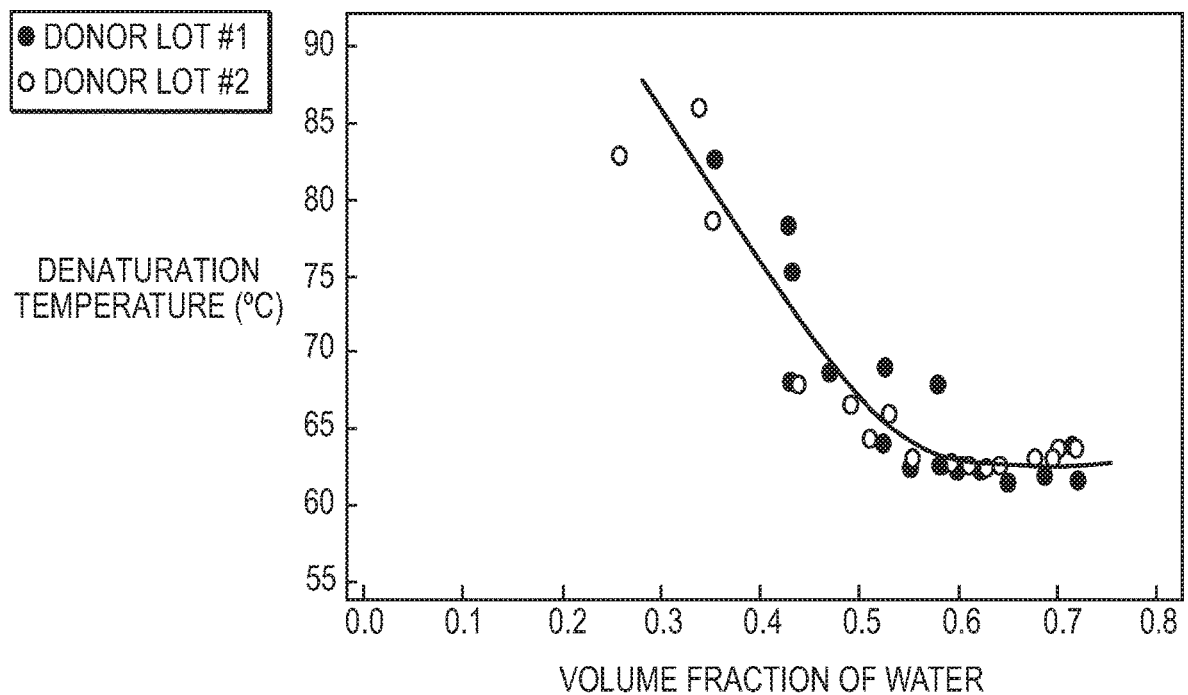
FIG. 16A is a line graph depicting the effect of hydration on the stability of a tissue matrix without irradiation, according to certain embodiments.

The stability of human acellular dermal matrix (produced as described in Example 4) was measured using differential scanning calorimetric (DSC). As shown in FIG. 16A, for tissue matrices that were dehydrated below ~0.60 volume fraction of water, the stability of tissue matrix increased with the decrease of volume fraction of water. As described above, a volume fraction of water below ~0.60 is below the threshold hydration level.

Figure 16B:
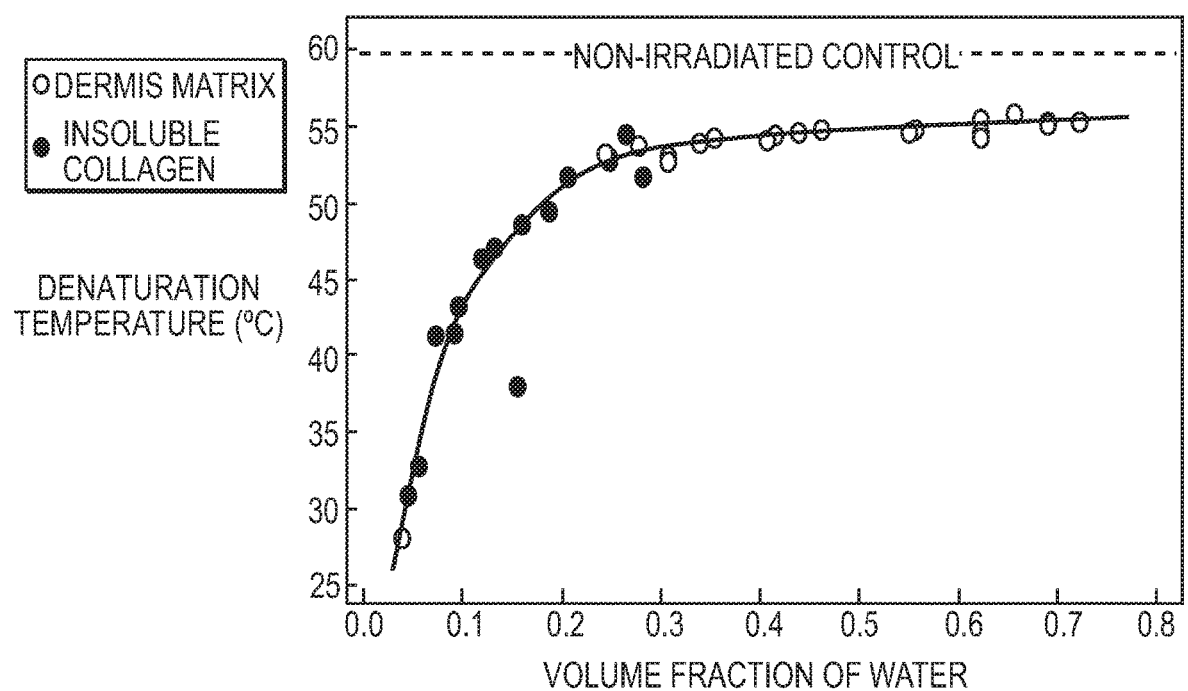
FIG. 16B is a line graph depicting the effect of hydration on the stability of a tissue matrix after treatment with gamma irradiation, according to certain embodiments.

Tissue samples and insoluble bovine collagen samples with different water content were treated with gamma irradiation at 19.3 kGy. After treatment, the gamma irradiation damage in tissue and collagen samples was assessed using DSC to determine the denaturation temperature of the samples. As shown in FIG. 16B, at the volume fraction of water below ~0.35, irradiation damage increased significantly as the volume fraction of water decreased.

From these experiments, it can be concluded that, in order to minimize the damage caused by gamma irradiation, the volume fraction of water in tissue matrix needs to be maintained between 0.35 and 0.60. This tissue hydration range corresponds to the water activity in tissue materials between 0.900 and 0.99. To retain optimal water activity in the tissue and also to minimize tissue damages caused by ionizing irradiation, a proper amount of tissue material can be incubated in a proper volume of concentrated protective solutions as described in the present disclosure.

Example 11: Repopulation and Revascularization of a Tissue Matrix in Murine Model The purpose of this study was to evaluate the cellular repopulation and revascularization of porcine regenerative tissue matrix (pATM) in a subcutaneous implantation model in the athymic mouse. This study was used to verify the following design requirements: (1) the tissue supports connective tissue cell in-growth, and (2) the tissue becomes vascularized when implanted into a subject.

This study was conducted in accordance with the following Regulation: FDA 21 CFR Part 58 *Good Laboratory Practice Regulations for Nonclinical Laboratory Studies* (GLP), Revised Apr. 1, 2006. The Test Facility followed all requirements specified in the LIFECELL approved protocol (LRD2007-01-001) and all applicable governmental regulations, as well as the Standard Operating Procedures of the Test Facility. The procedures were based on the International Organization for Standardization (ISO) 10993: Biological Evaluation of Medical Devices, Part 6: Tests for Local Effects after Implantation. The Quality Assurance Unit from NAMSA monitored the facilities, equipment, personnel, methods, practices, records and controls used in this study to assure that they were in conformance with this protocol, company SOP's and the appropriate GLP regulations.

Twenty (20) nude mice (*Mus musculus*)/Hsd: Athymic nude-nu/nu were assigned to one of four (4) groups representing eight (8) material samples of porcine regenerative acellular tissue matrix (pATM). The pATM was made by a process comprising the following steps: removing hair from a skin sample from a pig; decellularizing the skin sample; removing DNA from the decellularized skin sample using a DNase; treating the decelullarized skin sample with alpha-galactosidase, and sterilizing the decellularized skin sample (first with a solution containing 0.2% PAA followed by exposing the sample to low dose E-beam irradiation of 18 kGy±10%), each of which is described in detail above. Five (5) separate pieces of the same pATM material were placed in the animals during the surgical implantation. Each animal was implanted with two (2) pieces of material (A & B) chosen randomly. The study design is detailed below in Table 7.

TABLE 7

Study Design

| Group | Test Material # | Number of Implants | Number of Animals |
|---|---|---|---|
| A | 601(A & B) | 10 | 5 |
| B | 608(A & B) | 10 | 5 |
| C | 621(A & B) | 10 | 5 |
| D | 647(A & B) | 10 | 5 |

Animal testing is a prerequisite for safety testing. As the Test Materials were derived from pigs, these samples were xenogenic to the mice used in the study. In order to avoid problems with cross-species incompatibilities, the immuno-compromised athymic nude mouse was one of the available models. The athymic mouse has historically been used to evaluate the response of a biomaterial following implantation without the interference of an immune response.

The implants were stored refrigerated at 2 to 8° C. at the study facility until the time of implantation. Immediately prior to implantation, the implants were rinsed in a 0.9% sterile saline wash for a minimum of two (2) minutes, as per the instructions in the approved study protocol. All handling of the implant test materials was done utilizing aseptic technique.

On the day of the surgery, each of the twenty (20) mice was implanted with two (2) separate pieces of the same implant test material. The animals for each group were randomized. Two large incisions were made subcutaneously on either side of the lumbar region of the vertebral column. Using blunt dissection, a pocket was created in the subcutaneous tissue to accommodate the 0.5 cm×1.0 cm pieces of the implant test material. Once implanted, the surgical sites were closed with stainless steel wound clips.

Following implantation, the animals were observed daily for abnormal clinical signs. All of the animals survived for thirty-five (35) days post-implantation. At the end of the thirty-five (35) day time period, the implant test material and adjacent soft tissue were removed, fixed, and processed for histology. The slides were prepared, stained, and evaluated for histological evidence of the cellular repopulation of the tissue with fibroblasts and histological evidence of revascularization within the implant test material and surrounding tissue.

Characteristics of fibroblast repopulation of the implant test material were evaluated via histological assessment based on PASS/FAIL criteria. The following criteria were used to evaluate acceptance of the test material:

Cellular Repopulation:
1. Observed histological evidence of cellular repopulation is considered a PASS; and
2. The absence of cellular repopulation is considered a FAIL.

Revascularization:
1. Observed histological evidence of vascular channels is considered a pass; and
2. The absence of vascular channels is considered a FAIL.

The acceptance criteria for verification of the ability to "support connective tissue cell in-growth" and "become vascularized" are three (3) of the four (4) implant test material samples yielding a PASS for cellular repopulation and three (3) of the four (4) Test Material samples yielding a PASS for revascularization.

Fixed samples of the tissue underwent standard histological processing which was followed by hematoxylin and eosin (H & E) staining. A Pass/Fail scoring system was used to assess cellular (fibroblast) repopulation and revascularization of the implant. Cellular repopulation and revascularization was apparent in all test groups at thirty-five (35) days post-implantation. Details of the scoring per Test Group are summarized in Table 8.

TABLE 8

Histological Results Summary

| Group | Test Material | Number of Implants | Histology Assessment Repopulation | Revascularization |
|---|---|---|---|---|
| A | 601A | 5 | Pass | Pass |
|   | 601B | 5 | Pass | Pass |
| B | 608A | 5 | Pass | Pass |
|   | 608B | 5 | Pass | Pass |
| C | 621A | 5 | Pass | Pass |
|   | 621B | 5 | Pass | Pass |
| D | 647A | 5 | Pass | Pass |
|   | 647B | 5 | Pass | Pass |

Thus, the histological analysis of the porcine regenerative tissue matrix (pATM) indicates that the Test Groups showed revascularization and cellular repopulation at thirty-five (35) days. Additionally, all test materials including components A and B yielded passing outcomes for cellular repopulation and revascularization. These results indicate that the pATM does support the design verification requirement for "supports connective tissue in-growth" and "becomes vascularized" when implanted in a mammalian host.

Example 12. Repopulation and Revascularization of a Tissue Matrix in a Primate Model The following example describes the results from porcine Regenerative Tissue Matrix (pATM) implanted in an African Green monkey abdominal wall defect model over a 6-month time course. pATM grafts were implanted in the primate abdominal wall defect repair model and assessed for biological attributes through post-operative observations, biomechanical testing and histological assessment following 2-weeks, 1-month, 3 months and 6-months after implantation.

Gross and tactile examination of the explanted grafts at all time points yielded no evidence of graft defects, graft herniation, attachment of visceral tissue or signs of unusual inflammation. Furthermore, the explanted grafts yielded mechanical strength values consistent with a significant integration of the graft with the native abdominal wall tissue.

The histological assessment of the explanted grafts demonstrated evidence of fibroblast infiltration as early as 2-weeks and uniform cellular repopulation by 3-months. The revascularization of the grafts was minimal at 2-weeks, but appeared robust following 1-month of implantation. By 3-months of implantation, the grafts were uniformly revascularized with the presence of capillaries and arterioles. At the 2-week time point, the grafts elicited moderate immune cell infiltration at the periphery, consisting of lymphocytes and eosinophils. Following 1-month of implantation, an insignificant concentration of immune cells was observed throughout the grafts. The grafts displayed a time-dependent increase in new collagen deposition and collagen orientation. While no new collagen deposition was observed following 2 weeks of implantation, by 1 month, a significant amount of new, organized collagen was evident. By 3 months, 100% of the collagen within the grafts appeared to be newly deposited as well as fully aligned and organized.

pATM:

Briefly, the porcine dermal matrix was processed to pATM according to the methods described above in Example 9. The final packaged product was sterilized using E-beam irradiation.

Implantation:

The primate abdominal wall surgical procedure was performed at the Behavioral Science Foundation, Basseterre, St. Kitts. Twenty-four (24) adult African Green monkeys (*Chlorocebus aethiops*), weighing 3-6 kg (male or female), were obtained from Caribbean Primates Ltd. Full thickness defects (3×7 cm) were surgically made in the abdominal wall of each monkey, and each defect was closed with a single piece of pATM graft, followed by closure of the surgical site. Six animals were implanted per time point. The animals were held in-life for 2-weeks, 1-month, 3-months and 6-month implant intervals.

At the time of implantation, the surgeon made assessments of handling and tactile properties of the pATM. Post-operatively and until explants of grafts, the animals were monitored for evidence of pain, redness, swelling, inflammation, or other trauma consistent with a surgical procedure. Oral intake and elimination were observed.

At the time of explant, the animals were sacrificed, and the entire abdominal wall was circumferentially incised exposing the entire repair site. The veterinary surgeon made the following observations at the time of the explant surgery:

1) observational evidence of graft defects or herniation
2) observational evidence of bulging or wrinkling of the implant tissue
3) observational evidence of attachment of visceral tissue to the implant
4) observational evidence of unusual inflammatory response The explant samples were shipped to LIFECELL in tissue culture media at 4° C. on ice. Following receipt of the material at LIFECELL, the explants were evaluated for the following properties:

1) physical evidence of graft defects or herniation
2) physical evidence of bulging or wrinkling of the implant tissue
3) physical evidence of attachment of visceral tissue to the implant
4) measurement of implant tissue dimensions
5) integration of implant and native tissue
6) color of pATM
7) mechanical healing strength Histology preparation and staining of the pATM were performed as described above. The stained histology slides were reviewed (blind study) by a Board Certified Pathologist. The scoring of the slides is described below.

Samples explanted at the three month time point were damaged/altered due to a deviation in shipping procedures, thus rendering these samples unusable for some test methods. Gross observation of the explants was performed by the surgeons prior to the deviation and thus is included in the results. Photos taken of the explanted abdominal wall tissue following the deviation appeared similar to the photos from the other time points but were not used to generate any specific data items.

Results and Analysis
Pre-Implant Handling Characteristics

During the preparation of the pATM samples and the surgical procedure, the veterinary surgeon evaluated the handling and tactile properties of the pATM. The following attributes were evaluated by the surgeon:

1) Compressibility—Tactile compression of the graft material
2) Thickness—Tactile measurement of the graft depth
3) Pliability—Ability to stretch the graft for approximation and placement in the wound
4) Suturability—Ease of suture placement into the graft material

TABLE 9

The results from the surgeon's assessment of handling characteristics.
Surgeon's Assessment of pATM Handling Properties

| Animal No. | Compressibility | Thickness | Pliability | Suturability |
|---|---|---|---|---|
| 6147 | Soft | Thin | Yes | Easy |
| 6059 | Soft | Medium | Yes | Easy |
| 6113 | N/C[1] | Medium | N/C | Moderate |
| 5833 | Medium | N/C | Moderate | Difficult |
| 6145 | Medium | Thin | Moderate | N/C |
| 6175 | Medium* | Thick | Moderate* | Difficult |
| 6164 | Soft | Thin | Yes | Easy |
| 5953 | Soft | Thick | Moderate | Easy |
| 5929 | Soft | N/C | Yes | Easy |
| 5930 | N/C | Thin | N/C | N/C |
| 5938 | Firm | Medium | Moderate | N/C |
| 6136 | Firm | Thin | No | N/C |
| 5788 | Soft | Medium | Yes | Easy |
| 6128 | Soft | Medium | Yes* | Easy |
| 5865 | Medium | Medium | Moderate | Easy |
| 6176 | Firm | Medium | No | Moderate |
| 5965 | Firm | Thin | Yes | N/C |
| 5962 | Firm | Medium | Moderate | Moderate |
| 5685 | N/C | Medium | Yes | Easy |
| 5686 | Soft | Thin | Yes | Easy |
| 5687 | Soft | Medium | Yes | Easy |
| 6098 | Firm | Thin | N/C | Moderate |
| 6100 | Firm | Medium | No | Moderate |
| 6103 | N/C | Thin | No | N/C |

[1]NC = no comment from the surgeon regarding this attribute
*Not surgeons exact wording There were no remarkable observations with regards to the tactile properties of the material noted by the implant surgeon.

Post-Operative Observations

Animals were observed for appetite, outputs, and evidence of pain, as well as redness, swelling, and inflammation at the surgical site. All animals appeared to behave normally, without unusual redness, swelling, or inflammation beyond the normal expectations of abdominal surgery. There were no adverse events or unusual pathologic observations.

Surgeon's Gross Observations of Explants at Sacrifice

At the explant surgery, the veterinary surgeon assessed the implant site and made gross observations of the pATM material. Specifically, the following categories were monitored:

1) Graft Defects/Herniation—a visual and tactile examination for holes or tears in the explanted graft material.
2) Bulging/Wrinkling—areas above or below the plane of the normal level and smooth graft geometry.
3) Visceral Tissue Attachment—the presence of any visceral organ tissue (liver, spleen, intestines, etc.) attached to the graft material.
4) Inflammation—unusual redness or swelling of the abdominal wall repair site.

TABLE 10

The results from the surgeon's gross observations of the implantation site at the time of explant surgery.
Gross Observations of pATM at Sacrifice

| Duration | Animal No. | Defects / Herniation | Bulging/ Wrinkling | Visceral Tissue Attachment | Signs of Inflamation |
|---|---|---|---|---|---|
| 2-weeks | 6147 | None | None | None | None |
|  | 6059 | None | None | None | None |
|  | 6113 | None | Wrinkled | None | None |
|  | 5833 | None | Wrinkled | None | None |
|  | 6145 | None | Wrinkled | None | None |
|  | 6175 | None | Wrinkled | None | None |
| 1-month | 6164 | None | None | None | None |
|  | 5953 | None | Wrinkled | None | None |
|  | 5929 | None | None | None | None |
|  | 5930 | None | Wrinkled | None | None |
|  | 5938 | None | Wrinkled | None | None |
|  | 6136 | None | Wrinkled | None | None |
| 3-months | 5788 | None | None | None | None |
|  | 6128 | None | None | None | None |
|  | 5865 | None | None | None | None |
|  | 6176 | None | None | None | None |
|  | 5965 | None | None | None | None |
|  | 5962 | None | None | None | None |
| 6-months | 5685 | None | None | None | None |
|  | 5686 | None | None | None | None |
|  | 5687 | None | None | None | None |
|  | 6098 | None | None | None | None |
|  | 6100 | None | None | None | None |
|  | 6103 | None | None | None | None |

The surgeon's post-implantation graft assessment indicated no evidence of defects/herniations, visceral tissue attachments or signs of inflammation at any time point. The surgeon did observe some wrinkling of the grafts at the 2-week and 1-month time points, but no wrinkling was observed at the 3- or 6-month time points.

Gross Observations of Explants at LifeCell

Following the receipt of the explanted pATM samples at LIFECELL, gross and physical observations of the material were made as follows:

1) Graft Defects/Herniation
visual and tactile examination for holes or tears in the explanted graft material.

2) Bulging/Wrinkling areas above or below the plane of the normal level and smooth graft geometry.

3) Visceral Tissue Attachment the presence of any visceral organ tissue (liver, spleen, intestines, etc.) attached to the graft material.

4) Explant Size measurement of graft length and width.

5) Color

Color of the explanted graft.

6) Integration visual and tactile assessment of the extent of graft and native tissue incorporation at the surgical interface.

Biomechanical Healing Strength

Healing strength of the graft-native monkey tissue interface was measured by performing a tensile test to determine maximum load sustained by the explanted surgical site. The biomechanical samples were cut from the explants to contain graft material bridging the native monkey fascia-implant interface on both sides of the graft. Suture was removed from each interface and the entire sample was tested to failure. The resulting tensile strength was considered indicative of the healing repair across the implant/native tissue interface. Table 12 displays the results of the tensile testing to determine the healing repair strength.

TABLE 11

Results from gross observations of the explant samples.
Table 11: Gross Observations of Explanted pATM at LIFECELL

| Duration | Animal No. | Defects/ Herniation | Bulging/ Wrinkling | Visceral Tissue Attachment | Explant Dimensions | Integration | Color |
|---|---|---|---|---|---|---|---|
| 2-weeks | 6147 | None | None | None | 4.5 × 3.0 | Integrated | Flesh/White |
|  | 6059 | None | None | None | 4.5 × 2.8 | Integrated | Flesh |
|  | 6113 | None | Wrinkled | None | 4.5 × 3.5 | Integrated | Flesh |
|  | 5833 | None | Wrinkled | None | 5.0 × 2.5 | Integrated | Flesh |
|  | 6145 | None | Wrinkled | None | 5.0 × 2.4 | Integrated | N/C |
|  | 6175 | None | Wrinkled | None | 4.8 × 2.6 | Integrated | Flesh/White |
| 1-month | 6164 | None | None | None | 5.5 × 4.0 | Well integrated | White |
|  | 5953 | None | Wrinkled | None | 4.0 × 2.5 | Well integrated | White |
|  | 5929 | None | None | None | 4.5 × 3.5 | Well integrated | N/C |
|  | 5930 | None | Wrinkled | None | 4.5 × 3.5 | Well integrated | White |
|  | 5938 | None | Wrinkled | None | 4.0 × 3.5 | Well integrated | White |
|  | 6136 | None | Wrinkled | None | 4.0 × 3.0 | Well integrated | White |
| 3-months | 5788 | ND$^2$ | ND$^2$ | ND$^2$ | 5.9 × 3.3 | ND$^2$ | ND$^2$ |
|  | 6128 | ND$^2$ | ND$^2$ | ND$^2$ | 5.3 × 3.2 | ND$^2$ | ND$^2$ |
|  | 5865 | ND$^2$ | ND$^2$ | ND$^2$ | 7.3 × 2.9 | ND$^2$ | ND$^2$ |
|  | 6176 | ND$^2$ | ND$^2$ | ND$^2$ | 4.2 × 3.5 | ND$^2$ | ND$^2$ |
|  | 5965 | ND$^2$ | ND$^2$ | ND$^2$ | 3.6 × 3.8 | ND$^2$ | ND$^2$ |
|  | 5962 | ND$^2$ | ND$^2$ | ND$^2$ | 6.4 × 3.9 | ND$^2$ | ND$^2$ |
| 6-months | 5685 | None | None | None | 4.6 × 4.5 | Well integrated | Flesh |
|  | 5686 | None | None | None | 4.5 × 1.5 | Well integrated | Flesh/Red |
|  | 5687 | None | None | None | 5 × 4.4 | Well integrated | Flesh |
|  | 6098 | None | None | None | 7 × 2 | Well integrated | Flesh |
|  | 6100 | None | None | None | 5 × 1.1 | Well integrated | Flesh/White |
|  | 6103 | None | None | None | 4 × 4.5 | Well integrated | Flesh/White |

$^2$ND = not done. The physical assessment was not performed on these samples due to a deviation in shipping.

The post-implantation graft assessment by LIFECELL indicated no evidence of defects/herniations or visceral tissue attachments at any time point. The LIFECELL assessment did reveal some wrinkling of the grafts at the 2-week and 1-month time point but this outcome was not observed at 3- and 6-months. The LIFECELL assessment of the primate graft interface indicated evidence of tissue integration at 2-weeks that became well integrated by 1 month.

TABLE 12

Mechanical Healing Strength of the pATM

| Duration | Animal No. | Maximum Load (N/cm) | Mean ± std dev |
|---|---|---|---|
| 2-weeks | 6147 | 54.12 | 25.9 ± 17.0 |
|  | 6059 | 12.23 |  |
|  | 6113 | 26.88 |  |

TABLE 12-continued

Mechanical Healing Strength of the pATM

| Duration | Animal No. | Maximum Load (N/cm) | Mean ± std dev |
|---|---|---|---|
| | 5833 | 22.84 | |
| | 6145 | ND[1] | |
| | 6175 | 13.41 | |
| 1-month | 6164 | 44.54 | 36.6 ± 10.2 |
| | 5953 | 24.49 | |
| | 5929 | 48.24 | |
| | 5930 | 44.16 | |
| | 5938 | 30.93 | |
| | 6136 | 27.34 | |
| 3-months | 5788 | ND[2] | ND |
| | 6128 | ND[2] | |
| | 5865 | ND[2] | |
| | 6176 | ND[2] | |
| | 5965 | ND[2] | |
| | 5962 | ND[2] | |
| 6-months | 5685 | 64.44 | 28.7 ± 21.6 |
| | 5686 | 16.58 | |
| | 5687 | 18.15 | |
| | 6098 | 33.44 | |
| | 6100 | ND[3] | |
| | 6103 | 11.03 | |

[1]ND = not done. The mechanical strength was not performed due to insufficient sample material.
[2]ND = not done. The mechanical strength was not performed on these samples due to a deviation in shipping.
[3]ND = data not valid as sutures were not removed prior to testing The tensile test data yielded no statistically significant (t-test) difference in graft-native tissue junction breaking strengths between the 2-week, 1-month and 6-month samples. The healing strength values obtained in this protocol for the pATM samples are comparable to healing strength for primary repair previously established in this model using human ATM.

Histological Assessment of Biopsies

The histology slides obtained for each biopsy (center and interface pieces) were scored by a Board Certified pathologist. The samples were blinded to the reviewer and scored for the following characteristics.

A) Fibroblast Infiltration
 1) depth of infiltration of the cells into the graft
 2) percent of the biopsy fully repopulated with fibroblasts
 3) percent of biopsy remaining acellular
B) Re-Vascularization
 1) location of any vessel structures
 2) percent of biopsy fully re-vascularized
 3) size/type of vascular structure
C) Inflammation
 1) location of any inflammatory cells in the biopsy
 2) type of inflammatory cells present
 3) intensity of inflammatory response (significant, moderate, insignificant)
D) Remodeling
 1) percent of biopsy observed as new collagen (indicating remodeling)
 2) percent of collagen that appears organized
 3) alignment of collagen structure

TABLES 13A

| | | Histopathology assessment of biopsies | | | | | |
|---|---|---|---|---|---|---|---|
| | | Fibroblast Infiltration | | | Re-Vascularization | | |
| Duration | Animal No. | Depth | % fully repopulated | % acellular | Location | % vascular | Size |
| 0.5 Months | 6147 | center | 50 | <5 | Old | <5 | capillary |
| | 6059 | center | 50 | <5 | Old | <5 | capillary |
| | 6113 | center | 50 | <5 | Old | <5 | capillary |
| | 5833 | perimeter | <10 | 80 | Old | <5 | capillary |
| | 6145 | center | 30 | 30 | Old | <5 | capillary |
| | 6175 | perimeter | <10 | 90 | Old | <5 | capillary |
| 1 Month | 6164 | center | >90 | 0 | New | >90 | capillary |
| | 5953 | center | 50 | 0 | New | 50 | capillary |
| | 5929 | center | >90 | 0 | New | >90 | capillary |
| | 5930 | center | 80 | 20 | New | 80 | capillary |
| | 5938 | center | 70 | <10 | New | 70 | capillary |
| | 6136 | center | 30 | <10 | New | 30 | capillary |
| 3 Months | 5788 | center | 100 | 0 | New | 100 | capillary |
| | 6128 | center | 100 | 0 | New | 100 | capillary arteriole |
| | 5865 | center | 100 | 0 | New | >95 | capillary arteriole |
| | 6176 | center | 100 | 0 | New | 100 | capillary arteriole |
| | 5965 | center | 100 | 0 | New | 100 | capillary arteriole |
| | 5962 | center | 100 | 0 | New | 100 | capillary arteriole |
| 6 Months | 5685 | center | 100 | 0 | New | 100 | capillary arteriole |
| | 5686 | center | 100 | 0 | New | 100 | capillary arteriole |
| | 5687 | center | 100 | 0 | New | 100 | capillary arteriole |
| | 6098 | center | 100 | 0 | New | 100 | capillary arteriole |
| | 6100 | center | 100 | 0 | New | 100 | capillary arteriole |
| | 6103 | center | 100 | 0 | New | 100 | capillary arteriole |

TABLES 13B

| | | Inflammation | | | Remodeling | | |
|---|---|---|---|---|---|---|---|
| Duration | Animal No. | Location | Cell Type | Intensity | % new collagen | % organized collagen | organized collagen |
| 0.5 Month | 6147 | Interface | lymphocytes eosinophil | moderate | <5 | <5 | 0 |
| | 6059 | center | histiocytes PMN | significant | <5 | <5 | 0 |
| | 6113 | interface | lymphocytes eosinophil | moderate | <5 | <5 | 0 |
| | 5833 | interface | lymphocytes eosinophil | insignificant | <5 | <5 | 0 |
| | 6145 | interface | lymphocytes eosinophil | moderate | <5 | <5 | 0 |
| | 6175 | interface | lymphocytes eosinophil | insignificant | <5 | <5 | 0 |
| 1 Month | 6164 | center | lymphocytes | insignificant | >90 | >90 | aligned |
| | 5953 | center | lymphocytes | insignificant | 30 | 20 | aligned |
| | 5929 | center | lymphocytes | insignificant | >80 | >80 | aligned |
| | 5930 | interface | lymphocytes | moderate | 80 | 80 | aligned |
| | 5938 | center | lymphocytes | insignificant | 60 | 60 | aligned |
| | 6136 | interface | lymphocytes eosinophil | significant | 20 | 20 | non-aligned |
| 3 Month | 5788 | center | lymphocytes giant cells | focal significant | >90 | >90 | aligned |
| | 6128 | center | lymphocytes | insignificant | 100 | 100 | aligned |
| | 5865 | center | lymphocytes | insignificant | >95 | >95 | aligned |
| | 6176 | center | lymphocytes | insignificant | 100 | 100 | aligned |
| | 5965 | center | lymphocytes | moderate | >95 | >95 | aligned |
| | 5962 | center | lymphocytes | moderate | >90 | >90 | aligned |
| 6 Month | 5685 | center | lymphocytes | insignificant | 100 | 100 | aligned |
| | 5686 | center | lymphocytes | insignificant | 100 | 100 | aligned |
| | 5687 | center | lymphocytes | insignificant | 100 | 100 | aligned |
| | 6098 | center | lymphocytes | insignificant | 100 | 100 | aligned |
| | 6100 | center | lymphocytes | insignificant | 100 | 100 | aligned |
| | 6103 | center | lymphocytes | insignificant | 100 | 100 | aligned |

Histopathology assessment of biopsies

At the 2-week time point, all of the grafts displayed evidence of cell infiltration. Cells were observed at the centers of 4 grafts which were judged to be predominately repopulated with cells. The remaining grafts displayed cells only at the perimeter. At the 1-month time point all of the grafts displayed cell infiltration into the center of the implant, with the majority of the grafts completely repopulated with cells. Following both 3-months and 6-months of implantation, all of the grafts were homogenously repopulated with fibroblasts.

At the 2-week time point, none of the grafts displayed significant evidence of vascular structures. At the 1-month time point, all of the grafts displayed vascular structures, defined by their size as capillaries. Four of these grafts exhibited a level of greater than 70% full vascularity, while the remaining 2 grafts contained less than 50% full vascularity. By 3 months, all of the grafts displayed homogenous distribution of vascular structures observed to range from capillary to arteriole in size. This outcome was also observed for the 6-month implanted grafts.

At the 2-week time point, all of the grafts displayed immune cell infiltration predominantly at the periphery of the implant. The immune cells were identified as lymphocytes and eosinophils and the response judged to be moderate in intensity in most grafts. By 1 month of implantation, immune cells (lymphocytes) were observed to infiltrate into the center of the biopsy, but the overall cellular immune response was judged to be insignificant (low cell concentration) in 4 of the grafts. One graft at the 1-month time point displayed a more significant immune cell infiltration including lymphocytes and eosinophils, but the cells were only observed at the interface. Similar outcomes were observed for the 3-month implanted grafts, with lymphocytes observed at the center of the grafts and the overall cellular immune response ranging from insignificant to moderate. One graft yielded a focal, localized infiltration of giant cells. By 6 months, all of the cellular immune response was judged to be insignificant.

At the 2-week time point, none of the grafts displayed evidence of new collagen deposition or organization. At the 1-month time point, all of the grafts displayed some new collagen deposition. Three grafts yielded >80% new collagen that was organized in an aligned orientation. The three remaining grafts displayed less new collagen (20%-60%), but in two of these samples the deposited collagen was observed to be aligned. Following both 3-months and 6-months of implantation, all of the grafts displayed evidence of 100% new collagen deposition that was both organized and aligned.

In conclusion, porcine regenerative tissue matrix was judged to be acceptable with regards to implant handling characteristics. The material was, in general, tactilely soft and pliable and able to be successfully sutured into abdominal wall defects. None of the 24 animals displayed any unusual signs of inflammation or adverse events during the lifetime of the implant.

The explanted grafts were generally soft and none yielded evidence of defects, herniation or visceral attachments. Some explanted grafts displayed evidence of wrinkling at the early time points, though this effect was completely resolved at the 3-month time point. Visual and tactile inspection, as well as mechanical evaluation of the graft-native tissue interface, indicated complete integration of the graft into the surrounding host tissue.

The histological assessment of the explanted grafts demonstrated evidence of fibroblast infiltration as early as 2 weeks and uniform cellular repopulation by 3 months. Revascularization of the grafts was minimal at 2 weeks, but appeared robust following 1 month of implantation. By 3 months of implantation, the grafts were uniformly revascularized with the presence of both capillaries and arterioles. At the 2-week time point, the grafts yielded moderate immune cell infiltration at the periphery that consisted of lymphocytes and eosinophils. Following 1 month of implantation, immune cells were observed to be uniformly distributed within the grafts, but the overall cellular immune response was judged to be insignificant. At 6 months, immune cell response to each of the grafts was considered insignificant. The grafts displayed a time-dependent increase in new collagen deposition and orientation. No new collagen was observed following 2 weeks of implantation, but by 1 month, a significant amount of new, organized collagen was evident. By 3 months, the grafts yielded 100% new collagen that was organized and aligned.

Example 13. Performance of the pATM in Human Subjects

About 20 human patients were implanted with the pATM made as described above (see Example 9). Five of the implants were breast implants and the remainder ventral hernia repairs. At 2 months following implantation, all surgeons who performed the implantations and monitor the patients reported very positive clinical observations, e.g., minimal inflammation, minimal seroma formation, and minimal drainage. These findings indicate that there is no evidence of xeno-rejection or foreign body response.

The invention claimed is:

1. A method for producing a tissue matrix, the method comprising:
   selecting a mammalian tissue;
   contacting the tissue with a decellularization solution to remove substantially all cells from the tissue to produce an acellular tissue matrix;
   contacting the tissue matrix with a protective solution effective to stabilize the tissue matrix during and after exposure to irradiation, wherein the protective solution comprises:
   a biocompatible buffer;
   a salt;
   a surfactant;
   a transition-metal chelator;
   a tissue stabilizer; and
   a biocompatible co-solute;
   packaging the tissue matrix in a sealed pouch; and
   exposing the tissue matrix to an irradiation dose to sterilize the tissue matrix.

2. The method of claim 1, wherein the irradiation comprises E-beam irradiation.

3. The method of claim 1, wherein the irradiation comprises gamma irradiation.

4. The method of claim 1, wherein the tissue matrix is exposed to an irradiation dose ranging from about 6 kGy to about 60 kGy.

5. The method of claim 1, wherein the tissue matrix is exposed to irradiation such that the matrix absorbs 6 kGy to 30 kGy of the radiation.

6. The method of claim 1, wherein the tissue matrix is exposed to irradiation for a time ranging from about 2 hours and about 12 hours.

7. The method of claim 6, wherein the tissue matrix is exposed to an irradiation dose ranging from about 6 kGy to about 15 kGy.

8. The method of claim 1, wherein the tissue is porcine or equine tissue.

9. The method of claim 1, wherein the tissue is non-human tissue.

10. The method of claim 1, wherein the tissue is non-human primate tissue.

11. The method of claim 1, wherein the mammal is human tissue.

12. The method of claim 11, wherein the tissue matrix is further treated with one or more of a DNA nuclease and alpha-galactosidase.

13. The method of claim 1, wherein the tissue matrix is selected from the group consisting of skin, bone, cartilage, meniscus, dermis, myocardium, periosteum, artery, vein, stomach, small intestine, large intestine, diaphragm, tendon, ligament, neural tissue, striated muscle, smooth muscle, bladder, urethra, ureter, and gingiva.

14. The method of claim 1, wherein the biocompatible buffer comprises a citrate buffer.

15. The method of claim 1, wherein the biocompatible buffer comprises a combination of a citrate buffer and a phosphate buffer.

16. The method of claim 1, wherein the biocompatible buffer is selected from the group consisting of an acetate buffer, a citrate buffer, a phosphate buffer, and a combination of a citrate buffer and a phosphate buffer.

17. The method of claim 1, wherein the salt in the protective solution is at a concentration of up to about 150 mM in the solution.

18. The method of claim 1, wherein the salt comprises sodium chloride.

19. The method of claim 1, wherein the surfactant in the protective solution is in an amount of about 0.2% or less of the solution.

20. The method of claim 1, wherein the surfactant comprises polyoxyethylenesorbitan monolaurate or polyoxyethylenesorbitan monooleate.

21. The method of claim 1, wherein the transition-metal chelator in the protective solution is at a concentration of between about 1 mM to about 10 mM.

22. The method of claim 1, wherein the transition-metal chelator comprises ethylenediamine tetraacetic acid.

23. The method of claim 1, wherein the transition-metal chelator comprises ethylene glycol-bis (2-aminoethyl ether)-N,N,N',N'-tetraacetic acid.

24. The method of claim 1, wherein the tissue stabilizer is in the protective solution in an amount of up to about 10% (w/v) of the solution.

25. The method of claim 1, wherein the tissue stabilizer comprises glycerol.

26. The method of claim 1, wherein the tissue stabilizer is present at a concentration of about 10% of the protective solution.

27. The method of claim 1, wherein the tissue stabilizer is present at a concentration of about 500 mM or less in the protective solution.

28. The method of claim 1, wherein the tissue stabilizer is present at a concentration of about 200 mM or less in the protective solution.

29. The method of claim 1, wherein the biocompatible co-solute is in the protective solution in an amount of up to about 20% (w/v) of the solution.

30. The method of claim 1, wherein the biocompatible co-solute is a sugar or sugar alcohol.

31. The method of claim 30, wherein the sugar comprises trehalose.

32. The method of claim 30, wherein the sugar alcohol comprises mannitol.

33. The method of claim 1, wherein the protective solution has a pH of between about 5.2 to about 6.9 and the solution has a water activity of between about 0.930 to about 0.995.

34. The method of claim 1, wherein the protective solution has a pH ranging from about 5.4 to about 6.0.

\* \* \* \* \*